US010851365B2

(12) United States Patent
Luo et al.

(10) Patent No.: US 10,851,365 B2
(45) Date of Patent: Dec. 1, 2020

(54) OPTIMIZED MICROBIAL CELLS FOR PRODUCTION OF MELATONIN AND OTHER COMPOUNDS

(71) Applicant: DANMARKS TEKNISKE UNIVERSITET, Lyngby (DK)

(72) Inventors: Hao Luo, Lyngby (DK); Jochen Förster, Copenhagen (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 16/089,977

(22) PCT Filed: Mar. 30, 2017

(86) PCT No.: PCT/EP2017/057520
§ 371 (c)(1),
(2) Date: Sep. 28, 2018

(87) PCT Pub. No.: WO2017/167866
PCT Pub. Date: Oct. 5, 2017

(65) Prior Publication Data
US 2019/0119663 A1 Apr. 25, 2019

Related U.S. Application Data

(60) Provisional application No. 62/315,864, filed on Mar. 31, 2016.

(30) Foreign Application Priority Data

May 19, 2016 (EP) .................................... 16170405

(51) Int. Cl.
*C12N 9/78* (2006.01)
*C12N 1/20* (2006.01)
(Continued)

(52) U.S. Cl.
CPC ................. *C12N 9/78* (2013.01); *C12N 1/14* (2013.01); *C12N 1/16* (2013.01); *C12N 1/20* (2013.01);
(Continued)

(58) Field of Classification Search
None
See application file for complete search history.

(56) References Cited

U.S. PATENT DOCUMENTS 7,807,421 B2  10/2010  Yabuta et al.
2012/0246748 A1  9/2012  Guo et al.
(Continued)

FOREIGN PATENT DOCUMENTS

WO  WO 2013/127914  9/2013
WO  WO 2013/127915  9/2013
WO  WO 2015/032911  3/2015

OTHER PUBLICATIONS

PIR Accession No. S29895, published Dec. 5, 1998 (Year: 1998).*
(Continued)

*Primary Examiner* — Richard C Ekstrom
(74) *Attorney, Agent, or Firm* — McHale & Slavin, P.A.

(57) ABSTRACT

Described herein are recombinant microbial host cells comprising biosynthetic pathways and their use in producing oxidation products and downstream products, e.g., melatonin and related compounds, as well as enzyme variants, nucleic acids, vectors and methods useful for preparing and using such cells. In specific aspects, the present invention relates to monooxygenases, e.g., amino acid hydroxylases, with a modified cofactor-dependency, and to enzyme variants and microbial cells providing for an improved supply of cofactors.

21 Claims, 5 Drawing Sheets

Figure 1:
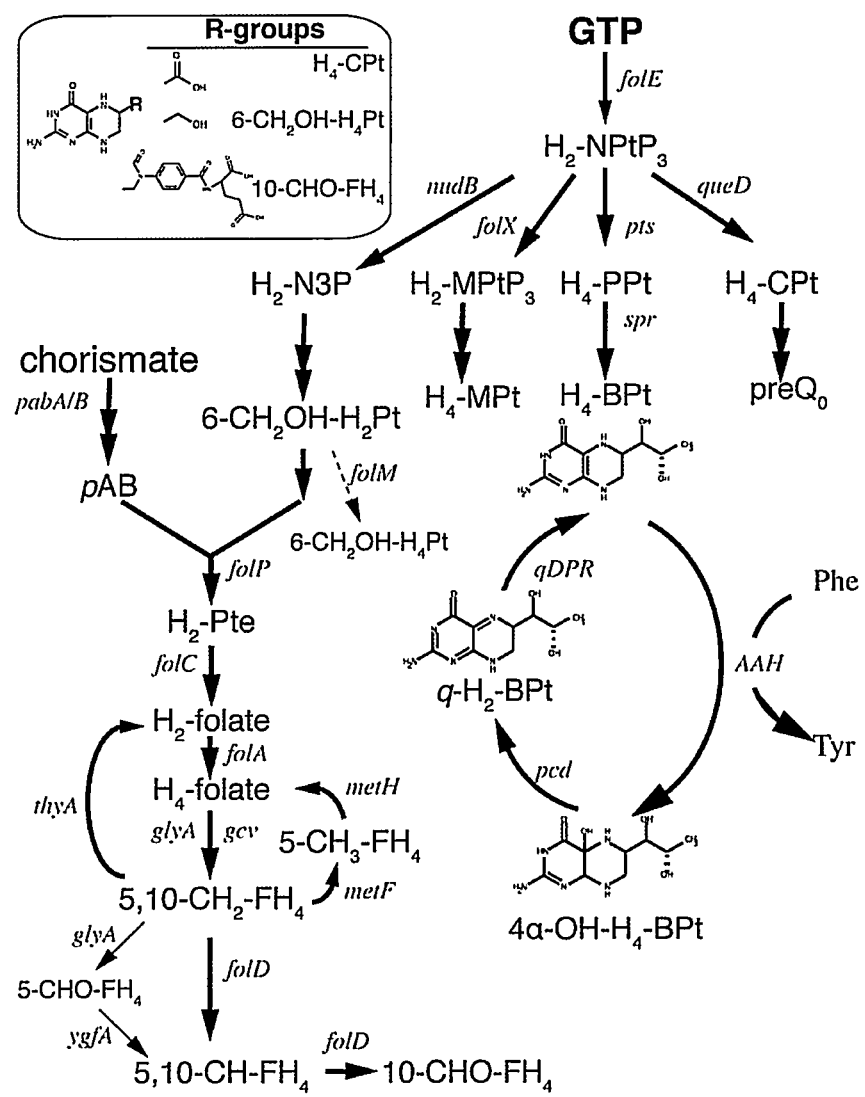

Specification includes a Sequence Listing.

(51) Int. Cl.
| | |
|---|---|
| *C12N 1/16* | (2006.01) |
| *C12N 1/14* | (2006.01) |
| *C12P 7/22* | (2006.01) |
| *C12N 9/02* | (2006.01) |
| *C12P 17/10* | (2006.01) |
| *C12P 13/22* | (2006.01) |
| *C12N 9/88* | (2006.01) |

(52) U.S. Cl.
CPC .............. *C12N 9/0071* (2013.01); *C12N 9/88* (2013.01); *C12P 7/22* (2013.01); *C12P 13/225* (2013.01); *C12P 13/227* (2013.01); *C12P 17/10* (2013.01); *C12Y 114/16001* (2013.01); *C12Y 114/16002* (2013.01); *C12Y 114/16004* (2013.01); *C12Y 305/04016* (2013.01); *C12Y 402/01096* (2013.01)

(56) References Cited

U.S. PATENT DOCUMENTS

| | | | |
|---|---|---|---|
| 2014/0134689 | A1 | 5/2014 | Lee et al. |
| 2019/0119663 | A1* | 4/2019 | Luo .................. C12Y 402/0109 |

OTHER PUBLICATIONS

Uni Prot Accession No. A0A0L0AQD0_9ENTR, published Nov. 11, 2015 (Year: 2015).*
Uni Prot Accession No. A0A085G995_9ENTR, published Oct. 29, 2014 (Year: 2014).*
International Search Report and Written Opinion of the International Searching Authority for PCT/EP2017/057520, dated May 17, 2017, pp. 1-16.
Susanne M. Germann et al., "Glucose-based Microbial Production of the Hormone Melatonin in Yeast *Saccharomyces cerevisiae*," retrieved from http://www.ncbi.nlm.nih.gov/pmc/articles/PMC5066760/pdf/BI0T-11-717.pdf, published online on Dec. 28, 2015, 10 pages.
Database Protein [online] Oct. 1, 2015 (Oct. 1, 2010), "GTP cyclohydrolase I [Shigella sonnei]", XP002770265, retrieved from NCBI Database accession No. WP_053008051.1.
Database Protein [online] Feb. 27, 2016 (Feb. 27, 2016), "GTP cyclohydrolase I FolE [*Escherichia coli*]", XP002770266, retrieved from NCBI Database accession No. WP_061336373.1.
Database Protein [online] Oct. 1, 2015 (Oct. 1, 2016), "GTP cyclohydrolase I [*Escherichia coli*]", XP002770267, retrieved from NCBI Database accession No. WP_032358670.1.
Database Protein [online] Mar. 22, 2016 (Mar. 22, 2016), "GTP cyclohydrolase I FolE [*Escherichia coli*]", XP002770268, retrieved from NCBI Database accession No. WP_001649026.
Database Protein [online] Jan. 15, 2016 (Jan. 15, 2016), "type I GTP cyclohydrolase I FolE [Erwinia teleogrylli]", XP002770269, retrieved from NCBI Database accession No. WP_058913807.1.
Database Protein [online] Mar. 22, 2016 (Mar. 22, 2016), "GTP cyclohydrolase I FolE (*Escherichia coli*)", XP002760019, retrieved from NCBI Database accession No. WP_001639660.
Database UniProt [online] May 9, 2003 (May 9, 2003), "RecName: Full=Tryptophan 5-hydroxylase 2; EC=1.14.16.4; AltName: Full=Neuronal tryptophan hydroxylase; AltName: Full=Tryptophan 5-monooxygenase 2;", XP002770270, retrieved from EBI accession No. UNIPROT:Q8IWU9 Database accession No. Q8IWU9.

Database Protein [online] Feb. 18, 2014 (Feb. 18, 2014), "Predicted: tryptophan 5-hydroxylase 2 isoform X1 [Elephantulus edwardii]", XP002770271, retrieved from NCBI Database accession No. XP_006882629.
Database UniProt [online] Oct. 1, 2002 (Oct. 1, 2002), "SubName: Full=Tryptophane hydroxylase {ECO:0000313|EMBL:AAK59708.1};", XP002760020, retrieved from EBI accession No. UNIPROT:Q8K3R1 Database accession No. Q8K3R1.
Yamamoto et al., "Genetic engineering of *Escherichia coli* for production of tetrahydrobiopterin", Metabolic Engineering, (2003), pp. 246-254, 5.
A. M. Ehrenworth et al., "Pterin-Dependent Mono-oxidation for the Microbial Synthesis of a Modified Monoterpene Indole Alkaloid", ACS Synthetic Biology, 2015, pp. 1295-1307, 4.
Lin et al., 'Engineering Bacterial Phenylalanine 4-Hydroxylase for Microbial Synthesis of Human Neurotransmitter Precursor 5-Hydroxytryptophan, ACS Synthetic Biology', 2014, pp. 497-505, 3.
Hara et al., "Enhanced synthesis of 5-hydroxy-L-tryptophan through tetrahydropterin regeneration", AMB Express 2013, pp. 1-7, 3:70.
Winge et al., "Activation and stabilization of human tryptophan hydroxylase 2 by phosphorylation and 14-3-3 binding", Biochem. J. (2008) pp. 195-204, 410.
Moran et al., "Expression and Characterization of the Catalytic Core of Tryptophan Hydroxylase", The Journal of Biological Chemistry, Issue of May 15, 1998, pp. 12259-12266, vol. 273, No. 20.
Lee et al., Overexpression of ethionine resistance gene for maximized production of S-adenosylmethionine in *Saccharomyces cerevisiae* sake kyokai No. 6, Korean J. Chem. Eng., 2010, pp. 587-589, 27(2).
Mckenzie et al., "Fast, easy and efficient: site-specific insertion of transgenes into Enterobacterial chromosomes using Tn7 without need for selection of the insertion event", BMC Microbiology 2006, pp. 1-7, 6:39.
Nar et al., "Active site topology and reaction mechanism of GTP cyclohydrolase I", Proc. Natl. Acad. Sci. USA, Dec. 1995, pp. 12120-12125,vol. 92.
Rebelo et al, "Biosynthesis of Pteridines. Reaction Mechanism of GTP Cyclohydrolase I", J. Mol. Biol. (2003) pp. 503-516,326.
Pribat et al., "FolX and FolM Are Essential for Tetrahydromonapterin Synthesis in*Escherichia coli* and Pseudomonas aeruginosa", Journal of Bacteriology, Jan. 2010, pp. 475-482, vol. 192, No. 2.
Pribat et al, "Nonflowering Plants Possess a Unique Folate-Dependent Phenylalanine Hydroxylase That Is Localized in Chloroplasts", The Plant Cell, Oct. 2010, pp. 3410-3422, vol. 22.
Baba et al., "Construction of *Escherichia coli* K-12 in-frame, single-gene knockout mutants: the Keio collection", Molecular Systems Biology, 2006, pp. 1-11, Article No. 2006.0008.
C.S. Cobbett, "Repression of the aroF promoter by the TyrR repressor in *Escherichia coii* K-12: roie of the 'upstream' operator site", Molecular Microbiology (1988) pp. 377-383, 2(3).
Datsenko et al., "One-step inactivation of chromosomal genes in *Escherichia coli* K-12 using PCR products", Proc. Natl. Acad. Sci., 2000, pp. 6640-6645, vol. 97, No. 12.
Satoh et al., "Engineeringof L-tyrosine oxidationin *Escherichia coli* and microbial production ofhydroxytyrosol", Metabolic Engineering, 2012, pp. 603-610, vol. 14.
Tchufistova et al., "A key role for the mRNA leader structure in translational control of ribosomal protein 51 synthesis in g-proteobacteria", Nucleic Acids Research, 2003, pp. 6996-7002, vol. 31, No. 23.

* cited by examiner

FIG. 3

```
ocTPH    ------------------------------------------------------MIEDNKE
hsTPH1   ------------------------------------------------------MIEDNKE
mmTPH    ----------------------------------------------------MIEDNKENKE
ggTPH    ------------------------------------------------------MIEDNKE
hsTPH2   MQPAMMMFSSKYWARRGFSLDSAVPEEHQLLGSSTLN------KPNSGKNDDK-GNKGSS   53
btTPH    MQPAMMMFSSKYWARRGLSLDSAVPEEHQLLTSLTLN------KTNSGKNDDKKGNKGSS
ssTPH    MQPAMMMFSSKYWARRGLSLDSAVPEEHQLLGSLTVSTFLKLNKSNSGKNDDKKGNKGSG
ecTPH    MQPAMMMFSSKYWARRGFSLDSAVPEEHQLLGNLTVN------KSNSGKNDDKKGNKGSS
scTPH    ------MISTESDLRRQLDEN--------------------VRSEADESTKEECPYINA ocTPH    NKDHSLERGRATLIFSLKNEVGGLIKALKIFQEKHVNLLHIESRK---------SKRRNS
hsTPH1   NKDHSLERGRASLIFSLKNEVGGLIKALKIFQEKHVNLLHIESRK---------SKRRNS
mmTPH    NKDHSSERGRVTLIFSLENEVGGLIKVLKIFQENHVSLLHIESRK---------SKQRNS
ggTPH    NKDHAPERGRTAIIFSLKNEVGGLVKALKLFQEKHVNLVHIESRK---------SKRRNS
hsTPH2   KREAATESGKTAVVFSLKNEVGGLVKALRLFQEKRVNMVHIESRK---------SRRRSS  104
btTPH    KNDTATESGKTAVVFSLKNEVGGLVKALKLFQEKHVNMIHIESRK---------SRRRSS
ssTPH    KSDTATESGKTAVVFSLKNEVGGLVKALKLFQEKHVNMVHIESRK---------SRRRSS
ecTPH    RSETAPDSGKTAVVFSLRNEVGGLVKALKLFQEKHVNMVHIESRK---------SRRRSS
scTPH    VQSHHQNVQEMSIIISLVKNMNDMKSIISIFTDRNINILHIESRLGRLNMKKHTEKSEFE
            .  :  . ::::** ::::..: . : :*  *...::::*****        .: . .

ocTPH    EFEIFVDCDTNREQLNDIFHLLKSHTNVLSVTPPDNFTMKEEG----------MESVPWF
hsTPH1   EFEIFVDCDINREQLNDIFHLLKSHTNVLSVNLPDNFTLKEDG----------METVPWF
mmTPH    EFEIFVDCDISREQLNDIFPLLKSHATVLSVDSPDQLTAKEDV----------METVPWF
ggTPH    EFEIFVDCDSNREQLNEIFQLLKSHVSIVSMNPTEHFNVQEDGD---------MENIPWY
hsTPH2   EVEIFVDCECGKTEFNELIQLLKFQTTIVTLNPPENIWTEEE----------ELEDVPWF  154
btTPH    EVEIFVDCECGKTEFNELIQSLKFQTTIVTLNPPENIWTEEEGKLTCVAKGKELEDVPWF
ssTPH    EVEIFVDCECGKTEFNELIQSLKFQTTIVTLNPPENIWTEEE----------ELEDVPWF
ecTPH    EVEIFVDCECGKTEFNELIQLLKFQTTIVTLNPPENIWTEEE----------ELEDVPWF
scTPH    PLELLVHVEVPCIEVERLLEELKSFSSYRIVQNPLMNLPEAKNP--------TLDDKVPWF
          .*::*. :      :.: ::  **   .   :    :.              : :**:

ocTPH    PKKISDLDHCANRVLMYGSELDADHPGFKDNVYRKRRKYFADLAMSYKYGDPIPKVEFTE
hsTPH1   PKKISDLDHCANRVLMYGSELDADHPGFKDNVYRKRRKYFADLAMNYKHGDPIPKVEFTE
mmTPH    PKKISDLDFCANRVLLYGSELDADHPGFKDNVYRRRRKYFAELAMNYKHGDPIPKIEFTE
ggTPH    PKKISDLDKCANRVLMYGSDLDADHPGFKDNVYRKRRKYFADLAMNYKHGDPIPEIEFTE
hsTPH2   PRKISELDKCSHRVLMYGSELDADHPGFKDNVYRQRRKYFVDVAMGYKYGQPIPRVEYTE  214
btTPH    PRKISELDRCSHRVLMYGSELDADHPGFKDNVYRQRRKYFVDVAMGYKYGQPIPRVEYTE
ssTPH    PRKISELDKCSHRVLMYGSELDADHPGFKDNVYRQRRKYFVDLAMGYKYGQPIPRVEYTE
ecTPH    PRKISELDKCSHRVLMYGSELDADHPGFKDNVYRQRRKYFVDVAMSYKYGQPIPRVEYTE
scTPH    PRHISDLDKVSNSVLMYGKELDADHPGFKDKEYRKRRMMFADIALNYKWGQQIPIVEYTE
         *::**:**  :: **:**.:**********:  **:**   *.::*:.** *: ** :*:**

ocTPH    EEIKTWGTVFRELNKLYPTHACREYLKNLPLLSKYCGYREDNIPQLEDISNFLKERTGFS
hsTPH1   EEIKTWGTVFQELNKLYPTHACREYLKNLPLLSKYCGYREDNIPQLEDVSNFLKERTGFS
mmTPH    EEIKTWGTIFRELNKLYPTHACREYLRNLPLLSKYCGYREDNIPQLEDVSNFLKERTGFS
ggTPH    EEIKTWGTVYRELNKLYPTHACREYLKNLPLLTKYCGYREDNIPQLEDVSRFLKERTGFT
hsTPH2   EETKTWGVVFRELSKLYPTHACREYLKNFPLLTKYCGYREDNVPQLEDVSMFLKERSGFT  274
btTPH    EETKTWGVVFRELSKLYPTHACREYLKNFPLLTKHCGYREDNVPQLEDVAAFLKERSGFT
ssTPH    EETKTWGIVFRELSKLYPTHACREYLKNFPLLTKYCGYREDNVPQLEDVSVFLKERSGFT
ecTPH    EETKTWGVVFRELSRLYPTHACQEYLKNFPLLTKYCGYREDNVPQLEDVSMFLKERSGFA
scTPH    IEKTTWGRIYRELTRLYKTSACHEFQKNLGLLQDKAGYNEFDLPQLQVVSDFLKARTGFC
          *  .***  ::::**.:** * **:*: :*: **  .  **.*  ::***:  ::  *** *:**
```

FIG. 3 (continued)

```
ocTPH      IRPVAGYLSPRDFLSGLAFRVFHCTQYVRHSSDPFYTPEPDTCHELLGHVPLLAEPSFAQ
hsTPH1     IRPVAGYLSPRDFLSGLAFRVFHCTQYVRHSSDPFYTPEPDTCHELLGHVPLLAEPSFAQ
mmTPH      IRPVAGYLSPRDFLSGLAFRVFHCTQYVRHSSDPLYTPEPDTCHELLGHVPLLAEPSFAQ
ggTPH      IRPVAGYLSPRDFLAGLAFRVFHCTQYVRHSSDPLYTPEPDTCHELLGHVPLLAEPSFAQ
hsTPH2     VRPVAGYLSPRDFLAGLAYRVFHCTQYIRHGSDPLYTPEPDTCHELLGHVPLLADPKFAQ  334
btTPH      VRPVAGYLSPRDFLAGLAYRVFHCTQYVRHGSDPLYTPEPDVTLSLLSHVPLIFDDQFPT
ssTPH      VRPVAGYLSPRDFLAGLAYRVFHCTQYVRHGSDPLYTPEPDTCHELLGHVPLLADPKFAQ
ecTPH      VRPVAGYLSPRDFLAGLAYRVFHCTQYVRHSSDPLYTPEPDTCHELLGHVPLLADPKFAQ
scTPH      LRPVAGYLSARDFLSGLAFRVFYCTQYIRHQADPFYTPEPDCCHELLGHVPMLADPKFAR
           :********.****:***:***:****:**  :**:******    .**.***::  : .*.

ocTPH      -FSQEIGLASLGASEEAVQKLATCYFFTVEFGLCKQDGQLRVFGAGLLSSISELKHVLSG
hsTPH1     -FSQEIGLASLGASEEAVQKLATCYFFTVEFGLCKQDGQLRVFGAGLLSSISELKHALSG
mmTPH      -FSQEIGLASLGASEETVQKLATCYFFTVEFGLCKQDGQLRVFGAGLLSSISELKHALSG
ggTPH      -FSQEIGLASLGASDEAVQKLATCYFFTVEFGLCKQEGQLRVYGAGLLSSISELKHSLSG
hsTPH2     -FSQEIGLASLGASDEDVQKLATCYFFTIEFGLCKQEGQLRAYGAGLLSSIGELKHALSD  393
btTPH      SFSNEVGRAVILASWGDKQENNQCYFFTIEFGLCKQEGQLRAYGAGLLSSIGELKHALSD
ssTPH      -FSQEIGLASLGASDEDVQKLATCYFFTIEFGLCKQEGQLRAYGAGLLSSIGELKHALSD
ecTPH      -FSQEIGLASLGASDEDVQKLATCYFFTIEFGLCKQEGQLRAYGAGLLSSIGELKHALSD
scTPH      -FSQEIGLASLGTSDEEIKKLATCYFFTIEFGLCRQDNQLKAYGAGLLSSVAELQHALSD
            **:*:*  *  :  :*      ::    *****:*****:*:.**:.:*******:.**:* **.

ocTPH      HAKVKPFDPKITYKQECLITTFQDVYFVSESFEDAKEKMREFTKTIKRPFGVKYNPYTRS
hsTPH1     HAKVKPFDPKITCKQECLITTFQDVYFVSESFEDAKEKMREFTKTIKRPFGVKYNPYTRS
mmTPH      HAKVKPFDPKIACKQECLITSFQDVYFVSESFEDAKEKMREFAKTVKRPFGLKYNPYTQS
ggTPH      SAKVKPFDPKVTCKQECLITTFQEVYFVSESFEEAKEKMREFAKTIKRPFGVKYNPYTQS
hsTPH2     KACVKAFDPKTTCLQECLITTFQEAYFVSESFEEAKEKMRDFAKSITRPFSVYFNPYTQS  453
btTPH      KACVKAFDPKTTCLQECLITTFQEAYFVSESFEEAKEKMRDFAKSITRPFSVYFNPYTQS
ssTPH      KACVKAFDPKTTCLQECLITTFQEAYFVSESFEEAKEKMREFAKSITRPFSVYFNPYTQS
ecTPH      KACVKAFDPKTTCLQECLITTFQEAYFVSESFEEAKEKMREFAKSITRPFSVHFNPYTQS
scTPH      KAVIKPFIPMKVINEECLVTTFQNGYFETSSFEDATRQMREFVRTIKRPFDVHYNPYTQS
           *  :*.*  *      .   :***:*::  :.***:*...:**:*.:::.*.:  :***:* ocTPH      IQILKDAKSITNAMNELRHDLDVVSDALGKVSRQLSV---------------
hsTPH1     IQILKDTKSITSAMNELQHDLDVVSDALAKVSRKPSI---------------
mmTPH      VQVLRDTKSITSAMNELRYDLDVISDALARVTRWPSV---------------
ggTPH      VQILKDTKSIASVVNELRHELDIVSDALSKMGKQLEV---------------
hsTPH2     IEILKDTRSIENVVQDLRSDLNTVCDALNKMNQYLGI---------------
btTPH      IEILKDTRSIENVVQDLRSDLNTVCDALNKMNQYLGI---------------
ssTPH      IEILKDTRSIENVVQDLRSDLNTVCDALNKMNQYLGI---------------
ecTPH      VEVLKDSRSIESVVQDLRSDLNTVCDALNKMNQYLGV---------------
scTPH      IEIIKTPKSVAKLVQDLQFELTAINESLLKMNKEIRSQQFTTNKIVTENRSS
           :::::  ..:*:  .  :::*:  :*    :  ::*  ::  :
```

FIG. 4

```
Ecoli   ------------------------------MPSLSKE--AALVHEALVARGLETPLRPP 27
human   MEKGPVRAPAEKPRGARCSNGFPE-RDPPRPGPSRPAE-KPPRPEAKSAQPADGWKGERP 58
yeast   MHNI------------QLVQEIERHETPLNIRPTSPYTLNPPVERDGFSWPSVGTRQRAE 48
                                       *:          .      .    .

Ecoli   VHEMDNETRKSLIAGHMTEIMQLLNLDLADDSLMETPHRIAKMYVDEIFSGLDYANFPKI 87
human   RSEEDNELNLPNLAAAYSSILSSLGENPQRQGLLKTPWRAASAMQF---FTKGYQETI-S 114
yeast   ETEEEEKERIQRISGAIKTILTELGEDVNREGLLDTPQRYAKAMLY---FTKGYQTNIMD 105
             *  ::: .    ::.  . *:    *. :   :.*:.** * *.       .*

Ecoli   TLI---ENKMKVDEMVTVRDITLTSTCEHHFVTIDGKATVAYIPKDSVIGLSKINRIVQF 144
human   DVLNDAIFDEDHDEMVIVKDIDMFSMCEHHLVPFVGKVHIGYLPNKQVLGLSKLARIVEI 174
yeast   DVIKNAVFEEDHDEMVIVRDIEIYSLCEHHLVPFFGKVHIGYIPNKKVIGLSKLARLAEM 165
         ::        . . **** *:** : * ****:*  : **. :.*:*:...*:****: *:..:

Ecoli   FAQRPQVQERLTQQILIALQTLLGTNNVAVSIDAVHYCVKARGIRDATSATTTTSLGGLF 204
human   YSRRLQVQERLTKQIAVAITEALRPAGVGVVVEATHMCMVMRGVQKMNSKTVTSTMLGVF 234
yeast   YARRLQVQERLTKQIAMALSDILKPLGVAVVMEASHMCMVSRGIQKTGSSTVTSCMLGGF 225
        :::* *******:** :*:       *    .*.*  ::* * *:  **::.   * *.*: : * *

Ecoli   KSSQNTRHEFLRAVRHHN-     222
human   REDPKTREEFLTLIRS---     250
yeast   RAH-KTREEFLTLLGRRSI    243
        :    :**.***    :
```

OPTIMIZED MICROBIAL CELLS FOR PRODUCTION OF MELATONIN AND OTHER COMPOUNDS

CROSS-REFERENCE TO RELATED APPLICATIONS

This U.S. non-provisional patent application is a national phase application of PCT/EP2017/057520, entitled "Optimized Microbial Cells for Production of Melatonin and Other Compounds," filed Mar. 30, 2017, which itself claims priority to European patent application number EP16170405.1 entitled "Optimized Microbial Cells for Production of Melatonin and Other Compounds," filed May 19, 2016, and to U.S. provisional application No. 62/315,865, entitled "Optimized Microbial Cells for Production of Melatonin and Other Compounds," filed Mar. 31, 2016, the contents of which are all fully incorporated herein by reference.

FIELD OF THE INVENTION

The present invention relates to recombinant microbial host cells comprising biosynthetic pathways and their use in producing oxidation products of aromatic amino acids, such as, e.g., 5HTP, as well as downstream products such as melatonin and related compounds. The present invention also relates to enzymes and enzyme variants and their use in such recombinant microbal cells, as well as methods and vectors useful for preparing and selecting such cells. More specifically, the present invention relates to microbial host cells repurposed for optimal monooxygenase, e.g., amino acid hydroxylase, function, and to methods of preparing and using such cells.

BACKGROUND OF THE INVENTION

Melatonin is a hormone secreted by the pineal gland in the brain which, inter alia, maintains the body's circadian rhythm, is involved regulating other hormones, and is a powerful anti-oxidant. Because of, e.g., its role in regulating circadian rhythm, melatonin has been available for many years as an over-the-counter dietary supplement in the U.S. This melatonin is, however, typically chemically synthesized, and there is a need for a simplified and more cost-effective procedure.

In animals, melatonin is biosynthesized from the native metabolite L-tryptophan via the intermediates 5-hydroxy-L-tryptophan (5HTP), serotonin and N-acetylserotonin. The first step is this pathway, the conversion of L-tryptophan to 5HTP, is catalyzed by L-tryptophan hydroxylase (TPH). TPH and many other mammalian aromatic amino acid hydroxylases require oxygen and tetrahydropterin (BH4) as cofactors.

WO 2013/127914 A1, WO 2013/127915 A1 and WO 2015/032911 A1 (Danmarks Tekniske Universitet) describe the production of 5HTP or melatonin in recombinant E. coli and S. cerevisiae cells expressing a TPH and enzymes of a biosynthetic pathway for producing the BH4 co-factor. BH4 does not occur naturally in E. coli or S. cerevisiae but can be biosynthesized from endogenous GTP via a pathway comprising a GTP cyclohydrolase I (GCH1), a 6-pyruvoyl-tetrahydropterin synthase (PTS or PTPS) and a sepiapterin reductase (SRP) (Yamamoto et al., 2003; Ehrenworth et al., 2015), and regenerated into BH4 via consecutive reactions by pterin-4α-carbolamine dehydratase (PCD) and dihydropterin reductase (DHPR) (e.g., WO 2015/032911 and Ehrenworth et al., 2015). Nar et al. (1995) and Rebelo et al. (2003) have reported on the structure of the E. coli GCH1; FolE. The amino acid sequence of FolE is reported in UniProtKB P0A6T5 (SEQ ID NO:16). An alternative FolE sequence is provided by NCBI Reference Sequence WP_001639660.

US 2014/134689 AA (University of California) describes methods of producing oxidation products such as L-DOPA, 5HTP, serotonin and/or melatonin from aromatic amino acids in a host cell which can, e.g., be capable of biosynthesizing BH4 or tetrahydromonapterin (MH4) from GTP. MH4 was reportedly capable of replacing THB as cofactor for tyrosine hydroxylase (TH).

MH4 is endogenous to, e.g., E. coli and P. aeruginosa cells, where it is hypothesized to be the cofactor for phenylalanine hydroxylase (PheH), its formation requiring FolX and FolM (Pribat et al., 2010a). Phenylalanine hydroxylases from non-flowering plants, however, uniquely preferred 10-formyltetrahydrofolate (10-THF) as cofactor over BH4 and were not capable of using MH4 (Pribat et al., 2010b).

Lin et al. (2014) describes that E. coli transformed with engineered bacterial phenylalanine 4-hydroxylases and a "regeneration" pathway based on a PCD and endogenous folM (dihydromonapterin reductase; DHMR) could convert tryptophan to 5HTP using endogenous MH4 as a co-factor. Hara and Kino (2013) produced 5HTP in a similar E. coli system, reportedly increasing the yield with the addition of BH4 cofactor.

Despite these and other advances in the art, there is still a need for recombinant microorganisms capable of efficient production of melatonin and related compounds. It is an object of the invention to provide such microorganisms.

SUMMARY OF THE INVENTION

It has been found by the present inventor that, surprisingly, oxidation products of amino acids, such as 5HTP, can be produced in a recombinant microbial cell comprising a heterologous monooxygenase, such as a TPH, and a heterologous PCD. Optionally, the microbial cell further comprises other enzymes for converting the oxidation product into a desired end-product. For example, the recombinant microbial cell may comprise heterologous enzymes converting 5HTP into serotonin and/or melatonin. In some embodiments, this is possible even in the absence of exogenous nucleic acid encoding a DHPR or a DHMR. While not being limited to theory, this suggests that native E. coli compounds may support the monooxygenase (TPH) activity.

So, in one aspect the present invention relates to a recombinant microbial cell comprising heterologous nucleic acid sequences encoding a monoxygenase, such as a TPH, and a PCD, wherein the microbial cell optionally does not comprise an exogenous nucleic acid encoding a DHPR or a DHMR, and to the use of such a recombinant cell for producing an oxidation product of an amino acid, e.g., an aromatic amino acid.

The present inventor has also identified variants of GCH1 which improve monooxygenase activity in recombinant microbial cells comprising a monooxygenase and a PCD, as well as variants of TPH with improved hydroxylation activity.

So, in other aspects, the present invention relates to such variant enzymes, as well as to nucleic acids and vectors encoding such variants, to recombinant microbial cells expressing such variants, and to the use of such enzymes and recombinant microbial cells for producing oxidation products, typically according to the preceding aspect.

To provide for production of other compounds of interests, the recombinant microbial cell can further comprise nucleic acids encoding other enzymes. For example, to produce compounds such as serotonin, N-acetyl-serotonin and melatonin, the recombinant microbial cell may comprise heterologous nucleic acid sequences encoding a 5HTP decarboxylase (ADDC), a serotonin acetyltransferase (AANAT) and/or an acetylserotonin O-methyltransferase (ASMT), as described further below.

In further aspects, the invention relates to methods of producing 5HTP, L-DOPA or tyrosine, as well as downstream products such as, e.g., serotonin, melatonin and hydroxytyrosol, using such recombinant microbial cells.

In addition, the present inventor has identified a nucleic acid sequence comprising a Trc promoter and a DNA coding sequence encoding an enzyme or other protein, wherein the 3'-end of the Trc promoter is operably, preferably directly, linked to the 5'-end of the DNA coding sequence, and wherein the 5'-end sequence of the DNA coding sequence is atgaaa.

So, in other aspects, the present invention relates to such nucleic acid sequences, their use in expressing enzymes or other proteins, to methods of improving expression of an enzyme or other protein in an *E. coli* host cell, and to variant enzymes or other proteins so produced.

These and other aspects and embodiments are described in more detail below.

LEGENDS TO THE FIGURES

FIG. 1: An overview of pterin and folic acids biosynthesis from GTP in *E. coli*. Black solid arrows indicate native *E. coli* biosynthesis pathways of folic acids, tetrahydromonapterin ($H_4$-MPt), and preQ$_0$ from a common precursor, dihydroneopterin triphosphate ($H_2$—NPtP$_3$). The heterologous tetrahydrobiopterin ($H_4$—BPt) biosynthesis and recycling pathways are also shown. Arrow in dashed line shows a putative reaction. Thin arrows represent formation of 5-formyl-tetrahydrofolate (5-CHO—FH$_4$) in a side reaction of GlyA and recycling via Ygfa. The insert shows selected pterin and folate compounds in *E. coli* which share a common head group with $H_4$—BPt. Genes are labeled in italics. Other abbreviations: aromatic amino acid hydroxylase (AAH), dihydroneopterin-3-phosphate ($H_2$—N$_3$P), dihydromonapterin triphosphate ($H_2$-MPtP$_3$), 6-pyruvoyl-tetrahydrobiopterin ($H_4$—PPt), 6-carboxy-tetrahydropterin ($H_4$—CPt), quinonoid dihydrobiopterin (q-$H_2$—BPt), 4α-OH—$H_4$—BPt (pterin-4α-carbinolamine), dihydropteroate ($H_2$—Pte), dihydrofolate ($H_2$-folate), tetrahydrofolate ($H_4$-folate), 5-methyl-tetrahydrofolate (5-CH$_3$—FH$_4$), 5,10-methenyltetrahydrofolate (5,10-CH$_2$—FH$_4$), 5,10-methylenetetrahydrofolate (5,10-CH—FH$_4$), 10-formyl-tetrahydrofolate (10-CHO—FH$_4$), and p-aminobenzoate (pAB).

Figure 2:
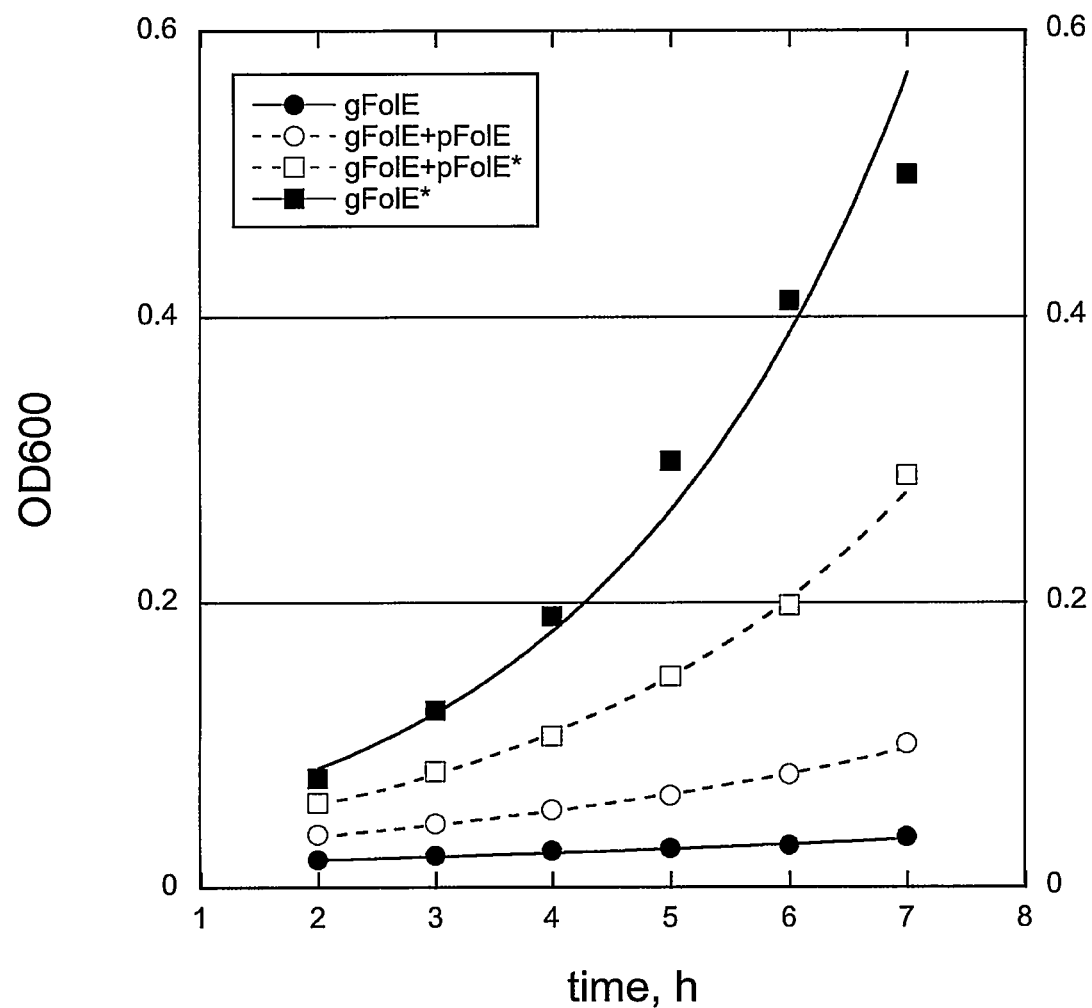

FIG. 2: FolE(T198I) mutation cannot be compensated by overexpression. TpH-dependent cell growth were evaluated under four conditions. 1) a single-copy native chromosomal FolE (gFolE), 2) a single-copy native chromosomal FolE and a native copy expressed from plasmid (gFolE+pFolE), 3) a single-copy native chromosomal FolE and a mutant copy expressed from plasmid (gFolE+pFolE*) and 4) a single-copy mutant chromosomal FolE (gFolE*) FIG. 3: ClustalW alignment of ocTPH (SEQ ID NO:1), hsTPH1 (SEQ ID NO:2), mmTPH (SEQ ID NO:6), ggTPH (SEQ ID NO:6), hsTPH2 (SEQ ID NO:3), btTPH (SEQ ID NO:), ssTPH (SEQ ID NO:5), ecTPH (SEQ ID NO:8) and scTPH (SEQ ID NO:5) indicating, in underlined text, the residues corresponding to residues E147, L148, N242 and P244 in *Homo sapiens* TPH2 (SEQ ID NO:3).

FIG. 4: Alignment of GCH1 from *E. coli* ("*E coli*," SEQ ID NO:16), *S. cerevisiae* ("yeast"; SEQ ID NO:17) and *Homo sapiens* ("human", SEQ ID NO:14), indicating the residues corresponding to residues D97-E112, K121-D130, N170-H180, S193-L200 and S207-N222 in *E. coli* GCH1 (SEQ ID NO:16).

DETAILED DISCLOSURE OF THE INVENTION

The present invention provides a recombinant microbial cell comprising nucleic acid sequences, optionally heterologous nucleic acid sequences, encoding a monooxygenase, a PCD and a GCH1. As shown by the results in Example 1, surprisingly, it is possible to use native bacterial THB-resembling species to support heterologous, optionally mammalian, TPH activity, with functional expression of a heterologous PCD gene being the only requirement. Additionally, by laboratory evolution, it was further possible to identify specific mutations in, e.g., GCH1 providing for a 10-fold increase in 5HTP production as compared to the parent *E. coli* cell.

In one aspect, the invention provides a variant of *E. coli* GTP cyclohydrolase I (FolE) having at least about 80% sequence identity to native *E. coli* GCH1 (SEQ ID NO:16) and comprising one or more mutations, wherein, in an *E. coli* cell comprising a pterin-4α-carbinolamine dehydratase (PCD) and at least one of a tryptophan hydroxylase (TPH), a tyrosine hydroxylase (TH) and a phenylalanine hydroxylase (PheH), the variant provides for an increased hydroxylation activity of at least one of the TPH, TH and PheH as compared to native *E. coli* GCH1, and the mutation is not T198P. In one embodiment, at least one of the one or more mutations is in an amino acid residue is in a segment selected from D97-E112, K121-D130, N170-H180, S193-L200 and S207-N222. For example, at least one of the one or more mutations can be in an amino acid residue selected from the group consisting of D97, M99, T101, V102, A125, K129, N170, V179, T196, T198, S199, L200, S207, H212, E213, F214, L215 and H221. Non-limiting examples according to this aspect are those wherein the variant (a) comprises a mutation selected from D97V, D97L, D97A, D97T, M99C, M99T, M99V, M99L, M99I, T101I, T101V, T101L, V102M, N170K, N170D, N170L, V179A, V179M, T196I, T196V, T196L, T198I, T198V, T198S, T198L, S199Y, S199F, L200P, L200C, L200S, L200A, S207R, S207K, S207M, H212R, H212K, E213K, E213R, F214A, F214G, F214S, L215P, L215Q, L215N, L215D, L215T, L215S, L215G, L215A, L215C, L215F, L215M, H221R and H221K, or a combination thereof;
(b) has at least about 90% sequence identity to native *E. coli* GCH1;
(c) provides for a hydroxylation activity of at least about 120%, such as at least 130%, as compared to native *E. coli* GCH1; or
(d) a combination of any two or more of (a) to (d).

Preferably, the GCH1 variant of any such aspect or embodiment comprises a mutation selected from T198I, T198S, F214S, V179A, M99I, L200P and L215P. The mutation may, for example, be T198I.

In another aspect, the invention provides a variant of a TPH, comprising a segment corresponding to residues E147 to T460 of *Homo sapiens* TPH (SEQ ID NO:3), an N-terminal methionine residue, and a mutation in at least one of the residues corresponding to residues E147, N242 and P244 in SEQ ID NO:3, optionally wherein the variant is a variant of a *Homo sapiens, Schistosoma mansoni, Gallus gallus, Sus scrofa, Mus musculus* or *Oryctolagus cuniculus* TPH, optionally wherein the segment in the variant has at least about 80% sequence identity to the segment in the native sequence. In separate and specific embodiments, the mutation in the residue corresponding to residue E147 is an amino acid substitution selected from 147K, 147R and 147H; the mutation in the residue corresponding to residue N242 is an amino acid substitution which is 242I; and/or the mutation in the residue corresponding to P244 is selected from 244C, 244D, 244L and 244Q, e.g., 244 C or 244D, such as 244D.

In another aspect, the invention provides a nucleic acid sequence encoding such variant *E. coli* GCH1, *Homo sapiens* TPH, or both, optionally in the form of one or more vectors which may further comprise one or more expression control sequences. The coding sequence of a variant *Homo sapiens* TPH may, for example, have the 5'-end atgaaa and be operably linked to a Trc promoter.

In another aspect, the invention provides a recombinant microbial cell comprising a variant *E. coli* GTP GCH1 as described herein or a nucleic acid sequence encoding such a variant. The recombinant microbial cell may further comprise nucleic acid sequences, optionally heterologous, encoding a monooxygenase and a PCD. In preferred embodiments, the recombinant microbial cell is one wherein
 (a) the PCD is selected from *Chromobacterium violecum, Homo sapiens, Pseudomonas aeruginosa* and *Rattus norvegicus*; or a functionally active variant, homolog or fragment thereof;
 (b) the monooxygenase is a TPH selected from a *Schistosoma mansoni, Homo sapiens, Gallus gallus, Bos taurus, Sus scrofa, Equus caballus, Mus musculus* and *Oryctolagus cuniculus* TPH; or a functionally active variant, homolog or fragment of any thereof;
 (c) the monooxygenase is a TH selected from *Rattus norvegicus, Homo sapiens, Mus musculus, Bos taurus, Gallus gallus* or a functionally active variant, homolog or fragment thereof;
 (d) the monooxygenase is a PheH selected from *Chromobacterium violaceum, Xanthomonas campestris* pv. *Viticola, Pseudomonas aeruginosa, Pseudomonas putida, Homo sapiens, Mus musculus, Streptomyces coeruleorubidus* or a functionally active variant, homolog or fragment thereof; or
 (e) a combination of (a) and (b), (a) and (c) or (a) and (d).

In some embodiments, each nucleic acid sequence is operably linked to an inducible, a regulated or a constitutive promoter, and/or at least one nucleic acid encoding an enzyme (e.g., the GCH1 variant), is chromosomally integrated.

In some embodiments, the recombinant microbial cell further comprises
 (a) a nucleic acid sequence encoding a 5HTP decarboxylase (ADDC);
 (b) nucleic acid sequences encoding an ADDC and a serotonin acetyltransferase (AANAT);
 (c) nucleic acid sequences encoding an ADDC, an AANAT, and an acetylserotonin O-methyltransferase (ASMT); and/or
 (d) nucleic acid sequences encoding a dopa decarboxylase, a tyramine oxidase and an alcohol dehydrogenase.

The invention also provides a method of producing one or more oxidation products of an aromatic amino acid, comprising culturing the recombinant microbial cell of any aspect or embodiment in a medium comprising a carbon source, and, optionally, isolating the oxidation product. The oxidation product may, for example, comprise at least one of 5HTP, L-DOPA, tyrosine, m-tyrosine, serotonin, melatonin and hydroxytyrosol.

In another aspect, the invention provides a method of selecting and, optionally, producing, a variant GCH1, the method comprising the steps of
 (a) preparing a population of variants of a parent GCH1;
 (b) preparing a population of microbial cells, each expressing a variant GCH1, a PCD, and at least one hydroxylase selected from a TPH, a TH, and a PheH;
 (c) analyzing the population of microbial cells for hydroxylation of a substrate for the hydroxylase as compared to a control, optionally wherein the control is a microbial cell expressing parent GCH1, the PCD and the at least one hydroxylase;
 (d) selecting at least one variant GCH1 which provides increased hydroxylation as compared to the control; and
 (e) optionally, producing the variant GCH1 by recombinant expression in a host cell.

In another aspect, the invention provides a nucleic acid sequence comprising a Trc promoter and a DNA coding sequence encoding a protein, wherein the 3'-end of the Trc promoter is directly linked to the 5'-end of the DNA coding sequence, and wherein the 5'-end sequence of the DNA coding sequence is atgaaa.

In a related aspect, the invention provides a method of producing a recombinant variant of a parent protein in an *E. coli* host cell, wherein the N-terminal amino acid sequence of the parent enzyme or other parent protein is MX (Met-Xaa), wherein X is not K (Lys), the method comprising the steps of:
 (a) preparing a vector comprising a Trc promoter directly linked to a DNA coding sequence encoding a variant of the parent protein which has an X2K amino acid substitution or an insertion of a K between the N-terminal M and X, wherein the 5'-end sequence of the DNA coding sequence is atgaaa;
 (b) transforming an *E. coli* host cell with the vector of (a);
 (c) expressing the recombinant variant of the parent protein in the host cell; and, optionally, harvesting the recombinant variant of the parent protein.

Definitions

Unless otherwise specified or contradicted by context, amino acid residue numbers in *Homo sapiens* TPH2 herein refer to their position in the sequence provided by NCBI accession No. NP_775489 and UniprotKB reference Q8IWU9 (SEQ ID NO:3).

Unless otherwise specified or contradicted by context, amino acid residue numbers in *E. coli* GCH1 (FolE) herein refer to their position in the sequence provided by UniprotKB reference P0A6T5 (SEQ ID NO:16).

As used herein, "exogenous" means that the referenced item, such as a molecule, activity or pathway, is added to or introduced into the host cell or microorganism. An exogenous nucleic acid sequence can, for example, be introduced either as chromosomal genetic material by integration into a host chromosome or as non-chromosomal genetic material such as a plasmid. Such an exogenous nucleic acid sequence can encode an enzyme or enzyme activity which is either heterologous to the host cell or organism in question or which is an endogenous enzyme or enzyme activity in the host cell or organism. Likewise, an exogenous molecule such as a substrate or cofactor can be added to or introduced into the host cell or microorganism, e.g., via adding the molecule to the media in or on which the host cell or microorganism resides.

In the present context the term "heterologous" means that the referenced item, such as a molecule, activity or pathway, does not normally appear in the host cell or microorganism species in question. Typically, a heterologous pathway comprises at least one nucleic acid sequence, enzyme or other component which is heterologous to the host cell.

As used herein, the terms "native" or "endogenous" mean that the referenced item is normally present in or native to the host cell or microbial species in question.

As used herein, "upregulating" an endogenous gene means increasing the transcription and/or translation of a gene present in the native host cell genome relative to a control, such as e.g. the unmodified host cell. Methods of upregulating genes are known in the art and include, e.g., introducing a non-native promoter increasing transcription, modifying the native promoter, deleting genes encoding repressor protein, introducing multiple copies of the gene of interest, etc. "Downregulating" an endogenous gene as used herein means to reduce, optionally eliminate, the transcription or translation of an endogenous gene relative to a control, such as, e.g., the unmodified host cell. Methods of down-regulating, disrupting and deleting genes are known to those of skill in the art, and include, e.g., site-directed mutagenesis, genomic modifications based on homologous recombination, RNA degradation based on CAS9, etc.

In the present context, "overexpressing" refers to introducing an exogenous nucleic acid sequence encoding an enzyme which is either heterologous or native to the microbial host cell, or is a functionally (i.e., catalytically) active fragment or variant thereof, and expressing the exogenous nucleic acid sequence to increase the enzyme activity in the microbial cell as compared to the microbial host cell without the introduced exogenous nucleic acid sequence, e.g., a native microbial host cell. This can be useful if, e.g., a microbial host cell does not normally contain the enzymatic activity referred to, where the native enzymatic activity is insufficient, or the native enzyme is subjected to unwanted regulation. In such cases, an exogenous nucleic acid sequence encoding an enzyme which is heterologous to the microbial host cell and which has the desired activity and regulation patterns can be introduced. Overexpression of a nucleic acid sequence can be achieved by placing the nucleic acid sequence under the control of a strong promoter. Non-limiting examples of strong promoters suitable for, e.g., *E. coli* cells are Ptrc, Plac, PlacUV5, PT7, and PTrp. Non-limiting examples of strong promoters suitable for, e.g., yeast cells are TEF1, PGK1, HXT7 and TDH3.

As used herein, a gene that is a "homolog" or "homologous" to another gene is generally an ortholog (i.e., a descended from the same ancestral sequence but separated when a species diverges into two separate species) or a paralog (i.e., separated by gene duplication within a genome). Typically, homologous genes encode proteins with a moderate to high sequence identity (e.g., at least about 30%, such as at least about 50%, such as at least about 60%, such as at least about 70%, such as at least about 80%, such as at least about 90%, such as at least about 95%, such as at least about 99%, over at least the catalytically active portion, optionally over the full length) and/or can at least partially substitute for the other protein in terms of function, when transferred from one species into another. Homologs of a particular gene can be identified using publicly available and specialized biological databases, e.g., by the eggNOG, InParanoid, OrthoDB, OrthoMCL, OMA, Roundup, TreeFam, LOFT, Ortholuge, EnsemblCompara GeneTrees and HomoloGene.

A "variant" of a protein comprises one or more mutations, such as amino acid substitutions, insertions and deletions as compared to the parent or reference enzyme. Typically, the variant has a high sequence identity to the parent or reference enzyme (e.g., at least about 70%, such as at least about 80%, such as at least about 90%, such as at least about 91%, 92%, 93%, 94%, 95%, 96%, 97% or 98%, such as at least about 99%, over at least a catalytically active portion, optionally over the full length of the mature form of the reference enzyme, excluding signal peptide sequences and the like). As used herein, a variant has less than 100% sequence identity over the full-length of the mature form of the parent or reference enzyme. A catalytically active portion of *Homo sapiens* TPH2 may, for example, correspond to residues E147 to T460 of *Homo sapiens* TPH2 (SEQ ID NO:3; NP_775489.2), wherein the term "corresponds to" a certain reference residue means that the residue aligns with the residue when using a standard dual or multiple sequence alignment program such as, e.g., ClustalW (available at, e.g., www.genome.jp) or ClustalOmega (available at, e.g., www.ebi.ac.uk), typically using the default settings.

A "fragment" of a protein comprises at least the part of the protein which is responsible for its function of interest, e.g., in the case of an enzyme, its catalytic part for the enzymatic activity of interest. Typically, a "fragment" comprises a segment corresponding to at least about 30%, such as at least about 50%, such as at least about 60%, such as at least about 70%, such as at least about 80%, such as at least about 90%, such as at least about 95%, of the full-length protein.

A "functionally active" or "catalytically active" variant or fragment comprises mutations or deletions, respectively, which do not substantially affect the function or catalytic activity of the variant or fragment as compared to the parent or reference protein and can substitute at least partially for the parent or reference protein in terms of the function of interest. Typically, unless used in the context of mutations in specific TPH or GHC1 (FolE) amino acid residues according to the invention, a variant or fragment has a function, as determined by a suitable activity assay, of 80-120%, such as 90%-110%, such as 95%-105%, of the parent or reference protein.

As used herein, "vector" refers to any genetic element capable of serving as a vehicle of genetic transfer, expression, or replication for a exogenous nucleic acid sequence in a host cell. For example, a vector may be an artificial chromosome or a plasmid, and may be capable of stable integration into a host cell genome, or it may exist as an independent genetic element (e.g., episome, plasmid). A vector may exist as a single nucleic acid sequence or as two or more separate nucleic acid sequences. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate host cell.

Construction of appropriate expression vectors and other recombinant or genetic modification techniques for practicing the invention are well known in the art (see, e.g., Green and Sambrook, Molecular Cloning, A Laboratory Manual, Cold Spring Harbor Laboratory Press (Cold Spring Harbor, N.Y.) (2012), and Ausubel et al., Short Protocols in Molecular Biology, Current Protocols John Wiley and Sons (New Jersey) (2002), and references cited herein). Appropriate microbial cells and vectors are available commercially through, for example, the American Type Culture Collection (ATCC), Rockville, Md.

The term "host cell" refers to any cell into which an exogenous nucleic acid sequence can be introduced and expressed, typically via an expression vector. The host cell may, for example, be a wild-type cell isolated from its natural environment, a mutant cell identified by screening, a cell of a commercially available strain, or a genetically engineered cell or mutant cell, comprising one or more other exogenous and/or heterologous nucleic acid sequences than those of the invention.

A "recombinant" cell or host cell as used herein refers to a host cell into which one or more exogenous nucleic acid sequences of the invention have been introduced, typically via transformation of a host cell with a vector.

The term "substrate" or "precursor", as used herein in relation to a specific enzyme, refers to a molecule upon which the enzyme acts to form a product. When used in relation to an exogenous biometabolic pathway, the term "substrate" or "precursor" refers to the molecule(s) upon which the first enzyme of the referenced pathway acts, such as, e.g., GTP in the pathway shown in FIG. 1. When referring to an enzyme-catalyzed reaction in a microbial cell, an "endogenous" substrate or precursor is a molecule which is native to or biosynthesized by the microbial cell, whereas an "exogenous" substrate or precursor is a molecule which is added to the microbial cell, via a medium or the like. For example, in the biometabolic pathway shown in FIG. 1, GTP is normally present in microbial host cells, and is therefore an endogenous substrate.

Unless otherwise stated, the term "sequence identity" for amino acid sequences as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences. Hence, the amino acid sequence GSTDYTQNWA will have a sequence identity of 80% with the sequence GSTGYTQAWA ($n_{dif}=2$ and $n_{ref}=10$). The sequence identity can be determined by conventional methods, e.g., Smith and Waterman, (1981), Adv. Appl. Math. 2:482, by the 'search for similarity' method of Pearson & Lipman, (1988), Proc. Natl. Acad. Sci. USA 85:2444, using the CLUSTAL W algorithm of Thompson et al., (1994), Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., (1990), Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used. Preferably, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later, e.g., as provided at World-Wide Web-address ebi.ac.uk/Tools/psalemboss_needle/. The parameters used are typically a gap open penalty of 10, a gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment–Total Number of Gaps in Alignment). In some embodiments, sequence identity values as used herein do not take into account specifically identified mutations of the embodiment it refers to, e.g., specifically identified amino acid substitutions.

Enzymes referred to herein can be classified on the basis of the handbook Enzyme Nomenclature from NC-IUBMB, 1992), see also the ENZYME site at the internet: http://www.expasy.ch/enzyme/. This is a repository of information relative to the nomenclature of enzymes, and is primarily based on the recommendations of the Nomenclature Committee of the International Union of Biochemistry and Molecular Biology (IUB-MB). It describes each type of characterized enzyme for which an EC (Enzyme Commission) number has been provided (Bairoch A., The ENZYME database, 2000, Nucleic Acids Res 28:304-305). The IUBMB Enzyme nomenclature is based on the substrate specificity and occasionally on their molecular mechanism.

Specific Embodiments of the Invention

As indicated in the Summary, in some aspects, the present invention relates to variants of TPH having improved tryptophan hydroxylase activity over the native parent enzyme, to variants of GCH1 (FolE) providing for improved amino acid hydroxylase activity in a microbial cell, and to variant nucleic acid sequences providing for improved, typically increased, expression of enzymes or other proteins. The present invention also relates to recombinant microbial cells comprising a heterologous monooxygenase, a heterologous PCD and, optionally, a heterologous and/or variant GCH1.

Monooxygenases

As used herein, suitable monooxygenases include, but are not limited to, phenylalanine hydroxylase (EC 1.14.16.1), phenylalanine 3-hydroxylase (EC 1.14.16.7), tyrosine 3-hydroxylase (EC 1.14.16.2), anthranilate 3-monooxygenase (EC 1.14.16.3), mandelate 4-monooxygenase (EC 1.14.16.6) and alkylglycerol monooxygenase (EC 1.14.16.5). Preferably, the monooxygenase is (a) capable of catalyzing the addition of a hydroxyl-group to an aromatic ring, preferably the aromatic ring of an aromatic amino acid such as, e.g., tryptophan, tyrosine, phenylalanine, histidine, thyroxine, 5HTP and/or L-DOPA, preferably aromatic amino acids in L-form; (b) capable of utilizing one or more of MH4, THB, tetrahydrofolate, 5-methyl-tetrahydrofolate, 5-formyl-tetrahydrofolate, 10-formyl-tetrahydrofolate, 6-carboxy-tetrahydropterin, and 6-hydroxymethyl-tetrahydropterin as cofactor for the referenced reaction. Particularly preferred are amino acid hydroxylases, with aromatic amino acid hydroxylases such as TPHs, THs and PheHs being most preferred. In a particular embodiment, the aromatic amino acid hydroxylase is not a PheH from a non-flowering plant.

Suitable TPHs, THs and PheHs include those listed in Table 1.

1. L-Tryptophan Hydroxylase (TPH)

Sources of nucleic acid sequences encoding a TPH include any species where the encoded gene product is capable of catalyzing the referenced reaction, including humans, mammals such as, e.g., mouse, cow, horse, chicken and pig, as well as other animals such as, e.g., the parasite *Schistosoma mansoni*. In humans and, it is believed, in other mammals, there are two distinct TPH alleles, referred to herein as TPH1 and TPH2, respectively. As used herein, a TPH is an enzyme capable of catalyzing the hydroxylation of L-tryptophan to 5HTP.

Examples of nucleic acids encoding TPH for use in aspects and embodiments of the present invention include, but are not limited to, those encoding the TPHs listed in Table 1, as well as functionally active variants, homologs and fragments thereof. The amino acid sequence of a TPH from *Mesocricetus auratus* (Golden hamster) is provided in NCBI Reference Sequence NP 001297486.1.

Functional fragments and variants of TPH enzymes are known in the art. For example, to increase heterologous expression in *E. coli* and the enzyme stability, the TPH sequence can be truncated to remove portions not needed for its catalytic activity which preserving the catalytic core of the enzyme. Specific examples of functional fragments of TPH include Met102 to Ser416 of *Oryctolagus cuniculus* TPH (Moran et al., J Biol Chem 1998; 273(20): 12259-66) and residues Asp45-Arg471 or Glu147-Thr460 (i.e., E147 to T460) of *Homo sapiens* TPH2, optionally comprising an added N-terminal methionine residue (see SEQ ID NOS:12 and 13, respectively). Other TPH sequences can be similarly truncated to create functionally active fragments or variants comprising the catalytic core. For example, SEQ ID NO:11 represents a fragment of *Homo sapiens* TPH2 comprising an added heterologous 20-amino acid polypeptide at its C-terminal. The *Homo sapiens* TPH2 sequence reported as NCBI accession No. NP_775489 (SEQ ID NO:10) has a 6-amino acid insert in the N-terminal portion.

Notably, *Schistosoma mansoni* TPH (SEQ ID NO:9) has advantageous properties with respect to, e.g., solubility, thus enabling no or less truncation of the enzyme sequence. In addition, as reported in Example 3, *Schistosoma mansoni* TPH has advantageous catalytic activity in an optimized recombinant cell according to the invention. Accordingly, in one embodiment, the TPH is *Schistosoma mansoni* TPH, or a functionally active fragment and/or variant thereof.

In one embodiment of any aspect of the invention, the TPH is a mammalian TPH, such as, e.g., *Homo sapiens* TPH2, or a fragment and/or variant thereof. In a preferred embodiment, the TPH comprises or consists essentially of a fragment of a TPH which corresponds to (i.e., aligns with) residues E147 to T460 or L148 to T460 of *Homo sapiens* TPH2 (SEQ ID NO:3), typically with an N-terminal methionine (M) residue; or a catalytically active variant thereof. This particular hsTPH fragment is set forth as SEQ ID NO:13.

In one embodiment, the TPH or TPH fragment is a variant comprising one or more mutations, such as insertions, deletions or amino acid substitutions, in at least one residue as compared to the reference (native parent) sequence. Preferably, a TPH variant has a mutation in a residue corresponding to a residue selected from E147 (if present), Asp242 (N, asparagine) and Pro244 (P, proline) in *Homo sapiens* TPH2.

The mutation in residue corresponding to E147 is preferably an amino acid substitution to a Lys (K; lysine), Arg (R; arginine) or His (H; histidine), most preferably an 147K mutation. Even more preferably, the nucleic acid sequence encoding the TPH has the 5'-end sequence atgaaa, encoding MK. In a specific embodiment, the nucleic acid sequence is operatively linked to a Trc promoter, optionally comprising the nucleic acid sequence of SEQ ID NO:53. Without being limited to theory, the mutation encoding for the N-terminal Met-Lys residues provides for an increased activity and/or expression level of the TPH.

The mutation in the residue corresponding to residue N242 in *Homo sapiens* TPH2 (SEQ ID NO:3) is preferably an amino acid substitution to Ile (I; isoleucine), i.e., 242I, whereas the mutation in residue P244 is preferably an amino acid substitution to a Cys (C, cysteine), Asp (D, aspartic acid), Leu (L, leucine) or Glu (Q, glutamine), i.e., 244C, 244D, 244L or 244Q, preferably 244D or 244C, such as 244D. The variant may also comprise a combination of two or more amino acid substitutions, such as, e.g., 242I/244D or 242I/244C, optionally in combination with 147K.

In a particularly preferred embodiment, the TPH variant comprises or consists of the amino acid sequence of SEQ ID NO:13 with E2K, N97I and P99C mutations introduced.

In another aspect, the invention provides SEQ ID NO: 13 having E2K, N97I and P99C mutations.

Typically, the TPH variant has tryptophan hydroxylation activity and a sequence identity of at least 30%, such as at least 50%, such as at least 60%, such as at least 70%, such as at least 80%, such as at least 90%, such as at least 91%, 92%, 93%, 94%, 95%, 96%, 97% or 98%, such as at least 99%, over at least the catalytically active portion, optionally over the full length, of the native TPH amino acid sequence in its mature form, excluding signal peptide sequences and the like. Preferably, a TPH variant comprising one or more mutations according to the invention provides for a tryptophan hydroxylation activity at least similar, typically higher than of the reference TPH, typically the native or parent TPH. For example, the TPH variant may provide for a tryptophan hydroxylation activity which is at least about at least about 100%, such as at least about 110%, such as at least about 130%, such as at least about 150%, such as at least about 200%, such as at least 250% of that of the native or parent TPH. Since TPH may also have phenylalanine hydroxylation activity, a TPH variant comprising one or more mutations according to the invention may also or alternatively provide for a phenylalanine hydroxylation activity at least similar to, or higher than, that of the reference TPH, typically the native or parent TPH. For example, the TPH variant may provide for a phenylalanine hydroxylation activity which is at least about 90%, such as at least about 100%, such as at least about 110%, such as at least about 130%, such as at least about 150%, such as at least about 200%, such as at least 250%, of that of the native or parent TPH, e.g., *Homo sapiens* TPH2.

Assays for measuring TPH activity in vitro are well-known in the art (see, e.g., Winge et al., Biochem J, 2008; 410:195-204 and Moran et al., 1998). Suitable assays are also provided by the present Examples, e.g., the assays in Examples 2-4, reflecting the ability of the TPH to catalyze the conversion of L-tryptophan to 5HTP, and Examples 6 and 7, reflecting the ability of the TPH to catalyze the conversion of L-phenylalanine to L-tyrosine.

In the recombinant host cell, the TPH is typically sufficiently expressed so that an increased level of 5HTP production from L-tryptophan can be detected as compared to the microbial host cell prior to transformation with the TPH, optionally in the presence of added THB cofactor and/or tryptophan substrate. Typically, in the context of the present invention, THB cofactor is not added. Alternatively, the expression level of the specific TPH enzyme can be evaluated by proteomic analysis, according to methods known in the art. In a preferred embodiment, the nucleic acid sequence encoding the TPH is operably linked to a strong promoter such as the Trc promoter, providing for high expression levels of the TPH.

2. L-Tyrosine Hydroxylase (TH)

Sources of nucleic acid sequences encoding a TH include any species where the encoded gene product is capable of catalyzing the referenced reaction, including humans, mammals such as, e.g., mouse, cow, horse, chicken and pig, as well as other animals. As used herein, a TH is an enzyme capable of catalyzing the hydroxylation of L-tyrosine to L-DOPA.

Examples of nucleic acids encoding a TH for use in aspects and embodiments of the present invention include, but are not limited to, those encoding the THs listed in Table 1, as well as catalytically active variants, homologs and fragments thereof. Exemplary variants and fragments of a TH include those resulting in the N-terminal sequence MK, e.g., by making an X2K amino acid substitution in a native TH having the N-terminal sequence MX (Met-Xaa), wherein X is not K (Lys), or an insertion of a K between the N-terminal M and X amino acid residues, In one embodiment, the TH is *Rattus norwegicus* TH, or a functionally active variant, homolog or fragment thereof.

Assays for measuring TH activity in vitro are well-known in the art. A suitable assay is also provided in the present Example 5, reflecting the ability of the TH to catalyze the conversion of L-tyrosine to L-3,4-dihydroxyphenylalaine (L-DOPA).

In the recombinant host cell, the TH is typically sufficiently expressed so that an increased level of L-DOPA production from L-tyrosine can be detected as compared to the microbial host cell prior to transformation with the TH, optionally in the presence of added THB cofactor and/or tyrosine substrate. Typically, in the context of the present invention, THB cofactor is not added. Alternatively, the expression level of the specific TH enzyme can be evaluated by proteomic analysis, according to methods known in the art. In a preferred embodiment, the nucleic acid sequence encoding the TH is operably linked to a strong promoter such as the Trc promoter, providing for high expression levels of the TH.

3. L-Phenylalanine Hydroxylase (PheH)

Sources of nucleic acid sequences encoding a PheH include any species where the encoded gene product is capable of catalyzing the referenced reaction, including humans, mammals such as, e.g., mouse, cow, horse, chicken and pig, as well as other animals. As used herein, a PheH is an enzyme capable of catalyzing the hydroxylation of L-phenylalanine to tyrosine.

Examples of nucleic acids encoding a PheH for use in aspects and embodiments of the present invention include, but are not limited to, those encoding the PheHs listed in Table 1, as well as functionally active variants, homologs and fragments thereof. Exemplary variants and fragments of a PheH include those resulting in the N-terminal sequence MK, e.g., by making an X2K amino acid substitution in a native PheH having the N-terminal sequence MX, wherein X is not K, or an insertion of a K between the N-terminal M and X amino acid residues, In one embodiment, the PheH is *C. violaceum* PheH, or a functionally active variant, homolog or fragment thereof.

In a specific embodiment, the PheH is a phenylalanine 3-hydroxylase, catalyzing the conversion of phenylalanine to m-tyrosine.

Assays for measuring PheH activity in vitro are well-known in the art. A suitable assay is also provided in the present Example 1, reflecting the ability of the PheH to catalyze the conversion of L-phenylalanine to L-tyrosine, as well as Examples 6 and 7.

In the recombinant host cell, the PheH is typically sufficiently expressed so that an increased level of L-tyrosine (or a variant thereof, such as, e.g., L-m-tyrosine) production from L-phenylalanine can be detected as compared to the microbial host cell prior to transformation with the PheH, optionally in the presence of added THB cofactor and/or phenylalanine substrate. Typically, in the context of the present invention, THB cofactor is not added. Alternatively, the expression level of the specific PheH enzyme can be evaluated by proteomic analysis, according to methods known in the art. In a preferred embodiment, the nucleic acid sequence encoding the PheH is operably linked to a strong promoter such as the Trc promoter, providing for high expression levels of the PheH.

Pterin-4α-Carbolamine Dehydratase (PCD)

The PCD is typically classified as EC 4.2.1.96, and converts HTHB to DHB in the presence of water, as shown in FIG. 1. Exemplary nucleic acids encoding PCD enzymes for use in aspects and embodiments of the present invention include, but are not limited to, those encoding the PCDs shown in Table 1, as well as functionally active variants, homologs and fragments thereof. In other embodiments, the exogenous nucleic acid encoding a PCD can encode a PCD which is endogenous to the microbial host cell, e.g., in the case of host cells from *Chromobacterium violaceum, Bacillus cereus, Lactobacillus ruminis Pseudomonas aeruginosa* or *Rhodobacteraceae* bacterium. In some embodiments, the microbial host cell endogenously comprises a sufficient amount of a native PCD. In such cases, transformation of the host cell with an exogenous nucleic acid encoding a PCD is optional.

Exemplary variants and fragments of a PCD include those resulting in the N-terminal sequence MK, e.g., by making an X2K amino acid substitution in a native PCD having the N-terminal sequence MX, wherein X is not K, or an insertion of a K between the N-terminal M and X amino acid residues, In one embodiment, the PCD is *C. violaceum* PheH, or a functionally active variant, homolog or fragment thereof. In a preferred embodiment of any aspect of the invention, the PCD comprises or consists essentially of *Chromobacterium violaceum* PCD (SEQ ID NO:21) or a functionally active variant, homolog or fragment thereof.

Assays for measuring PCD activity in vitro are well-known in the art (see, e.g., Köster et al., Biol. Chem. 1998; 379: 1427-1432). In the recombinant host cell, a sufficient expression of the PCD can typically be detected using an indirect assay, for example, measuring phenylalanine to tyrosine conversion of a PheH or TPH in a tyrosine auxotroph (see, e.g., Examples 1, 6 and 7). The expression level of the specific PCD enzyme can be evaluated according to methods known in the art, e.g., by proteomic analysis. In a preferred embodiment, the nucleic acid sequence encoding the PCD is operably linked to a strong promoter, providing for high expression levels of the PCD.

GTP Cyclohydrolase I (GCH1)

Sources of nucleic acid sequences encoding a GCH1 include any species where the encoded gene product is capable of catalyzing the referenced reaction. Examples of nucleic acids encoding a GCH1 for use in aspects and embodiments of the present invention include, but are not limited to, those encoding the GCH1 s listed in Table 1, as well as functionally active variants, homologs and fragments thereof. As used herein, a GCH1 is an enzyme capable of catalyzing the conversion of GTP to 7,8-dihydroneopterin triphosphate.

In one embodiment, the recombinant microbial cell comprises a GCH1 having the same or similar catalytic activity as *E. coli* GCH1 (FolE; SEQ ID NO:16) or another GCH1 listed in Table 1, or a catalytically active fragment and/or variant thereof. Advantageously, the GCH1 is FolE or a variant of FolE. FolE is a homodecameric protein and is composed of a pentamer of five dimers, and is the first enzyme in several biosynthetic pathways for production of tetrahydrofolates, tetrahydromonapterin and others which may act as monooxygenase (e.g., TPH, TH and PheH) cofactors in *E. coli* (see FIG. 1).

Surprisingly, as described in Examples 1 and 4-7, it was found that mutations in a number of residues of *E. coli* GCH1 were capable of increasing the supply of a cofactor for TPH, PheH and TH in *E. coli* cells. Accordingly, in one aspect of the invention, there is provided a variant of *E. coli* FolE (SEQ ID NO: 16) comprising one or more mutations, wherein, in an *E. coli* cell comprising a pterin-4α-carbinolamine dehydratase (PCD) and at least one of a tryptophan hydroxylase (TPH), a tyrosine hydroxylase (TH) and a phenylalanine hydroxylase (PheH), the variant provides for an increased hydroxylation activity of at least one of the TPH, TH and PheH as compared to native *E. coli* GCH1. In one embodiment, the mutation is not T198P. In another embodiment, the amino acid sequence of the variant is characterized by a moderate or high sequence identity to the native FolE sequence, as described below.

In one embodiment, at least one of the one or more mutations is in an amino acid residue in a segment selected from D97-E112, K121-D130, N170-H180, S193-L200 and S207-N222. For example, amino acid residues for such mutations include, but are not limited to, D97, M99, T101, V102, A125, K129, N170, V179, T196, T198, S199, L200, S207, H212, E213, F214, L215, H221, or a combination thereof. Preferred, non-limiting amino acid residues for such mutations include, but are not limited to, D97, M99, N170, V179, T198, L200, S207, H212, E213, F214, L215, and H221. Most preferably, the amino acid residue is at least one amino acid residue selected from M99, V179, T198, L200, F214, and L215. Preferably, the mutation in T198 is not T198P.

In one embodiment, exemplary amino acid substitutions in these segments include, but are not limited to, D97V, D97L, D97A, D97T, M99C, M99T, M99V, M99L, M99I, T101I, T101V, T101L, V102M, N170K, N170D, N170L, V179A, V179M, T196I, T196V, T196L, T198I, T198V, T198S, T198L, S199Y, S199F, L200P, L200C, L200S, L200A, S207R, S207K, S207M, H212R, H212K, E213K, E213R, F214A, F214G, F214S, L215P, L215Q, L215N, L215D, L215T, L215S, L215G, L215A, L215C, L215F, L215M, H221R, H221K, and combinations thereof. Preferred, non-limiting, mutations in these amino acid residues include D97V, M99I, N170K, N170D, V179A, V179M, T198I, T198S, L200P, S207R, H212R, E213K, F214S, L215Q, L215P and H221R, and combinations of any two or more thereof. In separate and specific embodiments, the variant comprises a mutation selected from M99I, V179A, T198I, T198S, L200P, F214S, and L215P.

In another embodiment, exemplary amino acid residues for such mutations include, without limitation: S3, S5, H12, A14, V28, H29, A41, G42, E46, N52, D57, M61, E62, I67, A68, I75, D97, M99, V102, T108, T117, A125, K129, I1133, Q157, N170, V179, K184, G187, T198, S199, L200, S207, H212, E213, F214, L215, H221, N222, and combinations thereof. Examples of amino acid substitutions in these residues include, without limitation, S3L, S5C, H12R, A14V, V28L, V28A, H29Y, A41G, G42D, E46D, N52K, D57V, M61I, E62K, I67V, A68S, I75V, D97V, M99I, V102M, T108N, T171, A125D, K129N, I133F, Q157L, N170K, N170D, V179A, V179M, K184R, G187S, T198I, T198S, S199Y, L200P, S207R, H212R, E213K, F214S, L215P, L215Q, H221R, N222I, and combinations thereof.

Specific, non-limiting combinations of mutations include:
(a) I67V, T117I, A125D and H221R
(b) E62K, N170K and L215P
(c) V102M and L215P
(d) Q157L and H212R
(e) V28L, L215P and N222I
(f) T108N, I133F and E213K
(g) S5C, D57V and L215Q
(h) H29Y, I75V and V179M
(i) A14V, E46D, M61I and D97V
(j) V28A, G42D and E213K
(k) N52K, A68S and S207R
(l) A41G, K129N and I133F
(m) S3L, K184R and S199Y; and
(n) H12R, N170D and G187S.

Nar et al. (1995) and Rebelo et al. (2003) have reported on the structure of FolE. The T198 residue is located in the $4^{th}$ β-strand that is located in close proximity to an Ca-helix defined by Ser207 to Asn222, apparently involved in oligomerization of the FolE complex. Thus, T198 can play a role in FolE oligomerization. Specifically, the mutation could affect the hydrophobic interaction with Leu215 and subsequently the positioning of the Ser207-Asn222 helix and overall polymerization of the FolE complex. Moreover, the alignment in FIG. 4 indicates that several of these segments conserved in the *Homo sapiens* (SEQ ID NO:14) and *S. cerevisiae* (SEQ ID NO:17) homologs of FolE.

So, in another specific embodiment, there is provided a functionally active variant, homolog or fragment of *E. coli* GCH1 (FolE; SEQ ID NO:16) comprising a mutation in the residue corresponding to D97, e.g., a D97V, D97L, D97A or D97T substitution. In one embodiment, the GCH1 is *E. coli* GCH1 wherein, preferably, the mutation is D97V. In one embodiment, the homolog is *Homo sapiens* GCH1 (SEQ ID NO:14) wherein, preferably, the mutation is D127V. In one embodiment, the homolog is *S. cerevisiae* GCH1 (SEQ ID NO:17) wherein, preferably, the mutation is D118V.

In another specific embodiment, there is provided a functionally active variant, homolog or fragment of *E. coli* GCH1 (FolE; SEQ ID NO:16) comprising a mutation in the residue corresponding to M99, e.g., a M99C, M99T, M99V, M99L or M99I substitution. In one embodiment, the GCH1 is *E. coli* GCH1 wherein, preferably, the mutation is M99I. In one embodiment, the homolog is *Homo sapiens* GCH1 wherein, preferably, the mutation is M129I. In one embodiment, the homolog is *S. cerevisiae* GCH1 wherein, preferably, the mutation is M120V.

In another specific embodiment, there is provided a functionally active variant, homolog or fragment of *E. coli* GCH1 (FolE) comprising a mutation in the residue corresponding to N170, e.g., a N170K, N170D or N170L substitution. In one embodiment, the GCH1 is *E. coli* GCH1, wherein, preferably, the mutation is N170K or N170D. In one embodiment, the homolog is *Homo sapiens* GCH1 wherein, preferably, the mutation is A200K or A200D. In one embodiment, the homolog is *S. cerevisiae* GCH1, and the mutation is L191K or L191D.

In another specific embodiment, there is provided a functionally active variant, homolog or fragment of *E. coli* GCH1 (FolE; SEQ ID NO:16) comprising a mutation in the residue corresponding to V179, e.g., a V179A or V179M substitution. In one embodiment, the GCH1 is *E. coli* GCH1 wherein, preferably, the mutation is V179A. In one embodiment, the homolog is *Homo sapiens* GCH1 wherein, preferably, the mutation is T209A. In one embodiment, the homolog is *S. cerevisiae* GCH1, and the mutation is S200A.

In a specific embodiment, there is provided a functionally active variant, homolog or fragment of *E. coli* GCH1 (FolE; SEQ ID NO:16) comprising a mutation in the residue corresponding to T198, e.g., a T198S, T198I, T198V or T198L substitution. In a specific embodiment, the T198 substitution is not T198P. In one embodiment, the GCH1 is *E. coli* GCH1 wherein, preferably, the mutation is T198S or T198I. In one embodiment, the homolog is *Homo sapiens* GCH1 wherein, preferably, the mutation is S228I. In one embodiment, the homolog is *S. cerevisiae* GCH1 wherein, preferably, the mutation is S219I.

In another specific embodiment, there is provided a functionally active variant, homolog or fragment of *E. coli* GCH1 (FolE; SEQ ID NO:16) comprising a mutation in the residue corresponding to L200, e.g., a L200P, L200C, L200S or L200A substitution. In one embodiment, the GCH1 is *E. coli* GCH1 wherein, preferably, the mutation is L200P. In one embodiment, the homolog is *Homo sapiens* GCH1 wherein, preferably, the mutation is M230P. In one embodiment, the homolog is *S. cerevisiae* GCH1 wherein, preferably, the mutation is M221P.

In another specific embodiment, there is provided a functionally active variant, homolog or fragment of *E. coli* GCH1 (FolE; SEQ ID NO: 16) comprising a mutation in the residue corresponding to S207, e.g., a S207R, S207K, or S207M substitution. In one embodiment, the GCH1 is *E. coli* GCH1 wherein, preferably, the mutation is S207R. In one embodiment, the homolog is *Homo sapiens* GCH1 wherein, preferably, the mutation is D237R. In one embodiment, the homolog is *S. cerevisiae* GCH1, and the mutation is H228R.

In another specific embodiment, there is provided a functionally active variant, homolog or fragment of *E. coli* GCH1 (FolE; SEQ ID NO:16) comprising a mutation in the residue corresponding to H212, e.g., a H212R or H212K substitution. In one embodiment, the GCH1 is *E. coli* GCH1 wherein, preferably, the mutation is H212R. In one embodiment, the homolog is *Homo sapiens* GCH1 wherein, preferably, the mutation is E242R. In one embodiment, the homolog is *S. cerevisiae* GCH1, and the mutation is E232R.

In another specific embodiment, there is provided a functionally active variant, homolog or fragment of *E. coli* GCH1 (FolE; SEQ ID NO:16) comprising a mutation in the residue corresponding to E213, e.g., a E213K or E213R substitution. In one embodiment, the GCH1 is *E. coli* GCH1 wherein, preferably, the mutation is E213K. In one embodiment, the homolog is *Homo sapiens* GCH1 wherein, preferably, the mutation is E243K. In one embodiment, the homolog is *S. cerevisiae* GCH1 wherein, preferably, the mutation is E233K.

In another specific embodiment, there is provided a functionally active variant, homolog or fragment of *E. coli* GCH1 (FolE; SEQ ID NO:16) comprising a mutation in the residue corresponding to F214, e.g., a F214A, F214G or F214S substitution. In one embodiment, the GCH1 is *E. coli* GCH1 wherein, preferably, the mutation is F214S. In one embodiment, the homolog is *Homo sapiens* GCH1 wherein, preferably, the mutation is F244S. In one embodiment, the homolog is *S. cerevisiae* GCH1 wherein, preferably, the mutation is F234S.

In another specific embodiment, there is provided a functionally active variant, homolog or fragment of *E. coli* GCH1 (FolE; SEQ ID NO:16) comprising a mutation in the residue corresponding to L215, e.g., a L215P, L215Q, L215N, L215D, L215T, L215S, L215G, L215A, L215C, L215F or L215M substitution. In one embodiment, the GCH1 is *E. coli* GCH1 wherein, preferably, the mutation is L215P or L215Q. In one embodiment, the homolog is *Homo sapiens* GCH1 wherein, preferably, the mutation is L245P or L245Q. In one embodiment, the homolog is *S. cerevisiae* GCH1 wherein, preferably, the mutation is L235P or L235Q.

In another specific embodiment, there is provided a functionally active variant, homolog or fragment of *E. coli* GCH1 (FolE; SEQ ID NO:16) comprising a mutation in the residue corresponding to H221, e.g., a H221R or H221K substitution. Preferably, the mutation in FolE is H221R. In one embodiment, the GCH1 is *S. cerevisiae* GCH1, and the mutation is H241K.

In a specific embodiment, a GCH1 variant of any preceding embodiment comprises the native, mature GCH1 sequence except for the listed mutation(s).

In one embodiment, any *E. coli* GCH1 (FolE) variant or fragment retain the native residues corresponding to C111, C182, H113 and H114 of the enzyme since, as reported by Rebelo (2003), replacement of these residues made the enzyme catalytically inactive.

In another aspect, the invention provides FolE (SEQ ID NO: 16) having a mutation selected from D97V, M99I, N170K, N170D, V179A, V179M, T198I, T198S, L200P, S207R, H212R, E213K, F214S, L215Q, L215P and H221R, or a combination of any two or more thereof.

In another aspect, the invention provides *Homo sapiens* GCH1 (SEQ ID NO:14) having a mutation selected from D127V, M129I, A200K, A200D, T209A, S228I, M230P, D237R, E242R, E243K, F244S, L245P and L245Q, or a combination selected from any two or more thereof.

In another aspect, the invention provides *S. cerevisiae* GCH1 (SEQ ID NO:17) having a mutation selected from D118V, M120V, L191K, L191D, S200A, S219I, M221P, H228R, E232R, E233K, F234S, L235P, L235Q and H241K, or a combination selected from any two or more thereof.

Typically, the functionally active GCH1 (FolE; SEQ ID NO: 16) variant has a sequence identity of at least 30%, such as at least 50%, such as at least 60%, such as at least 70%, such as at least 80%, such as at least 90%, such as at least 91%, 92%, 93%, 94%, 95%, 96%, 97% or 98%, such as at least 99%, over at least the catalytically active portion, optionally over the full length, of the reference or native GCH1 amino acid sequence in its mature form, excluding signal peptide sequences and the like. In some embodiments, the sequence identity value for a GCH1 variant does not take into account any specifically identified mutation in the embodiment in question. In one embodiment, the reference or native GHC1 sequence is SEQ ID NO:16 (FolE). In one embodiment, the reference or native sequence is SEQ ID NO:14 (*Homo sapiens* GCH1). In one embodiment, the reference or native sequence is SEQ ID NO:17 (*S. cerevisiae* GCH1).

The GCH1 variants of the invention may provide for one, two or all of a tryptophan, tyrosine and phenylalanine hydroxylation activity which is at least similar to, typically higher than that of the reference GCH1, e.g., the native or parent GCH1. This can be investigated in a microbial cell comprising the GCH1 variant, the hydroxylase and a PCD.

In one embodiment, a GCH1 variant comprising mutations in one or more specific amino acid residues or one or more specific amino acid substitutions according to the invention provides for a tryptophan hydroxylation activity at least similar to, typically higher than that of the reference GCH1, typically the native or parent GCH1, in a microbial cell comprising a TPH. For example, such a GCH1 variant may, in an *E. coli* cell comprising a TPH and a PCD provide for a tryptophan hydroxylase activity, converting L-tryptophan to 5HTP, which is at least about 100%, such as at least about 110%, such as at least about 130%, such as at least about 150%, such as at least about 200%, such as at least about 250%, such as at least about 300% of that of the native or parent GCH1. Suitable assays are provided in the Examples, e.g., Example 4. For example, the TPH may be Homo sapiens TPH2 (SEQ ID NO:3) or a functionally active variant, homolog or fragment thereof, such as a TPH variant comprising or consisting of the amino acid sequence of SEQ ID NO:13 with E2K, N97I and P99C mutations introduced; the PCD may, for example, be C. violaceum PCD (SEQ ID NO:21) or a functionally active variant, homolog or fragment thereof; and the assay conducted in the presence of about 100 mg/L L-tryptophan.

In one embodiment, a GCH1 variant comprising mutations in one or more specific amino acid residues or one or more specific amino acid substitutions according to the invention provides for a tyrosine hydroxylation activity at least similar to, typically higher than that of the reference GCH1, typically the native or parent GCH1, in a microbial cell comprising a TH. For example, such a GCH1 variant may, in an E. coli cell comprising a TH and a PCD provide for a tyrosine hydroxylase activity, converting L-tyrosine to L-DOPA, which is at least about 100%, such as at least about 110%, such as at least about 130%, such as at least about 150%, such as at least about 200%, such as at least about 250%, such as at least about 300% of that of the native or parent GCH1. Suitable assays are provided in the Examples, e.g., Example 5. For example, the TPH may be Rattus norvegicus TH (SEQ IDS NO:52) or a functionally active variant, homolog or fragment thereof; the PCD may, for example, be C. violaceum PCD (SEQ ID NO:21) or a functionally active variant, homolog or fragment thereof, and the assay conducted in the presence of about 100 mg/L L-tyrosine.

In one embodiment, a GCH1 variant comprising mutations in one or more specific amino acid residues or one or more specific amino acid substitutions according to the invention provides for a phenylalanine hydroxylation activity at least similar to, typically higher than that of the reference GCH1, typically the native or parent GCH1, in a microbial cell comprising a PheH. For example, such a GCH1 variant may, in an E. coli cell comprising a PheH (which may also be a TPH having phenylalanine hydroxylation activity), and a PCD provide for a phenylalanine hydroxylase activity, converting L-phenylalanine to tyrosine, which is at least about 100%, such as at least about 110%, such as at least about 130%, such as at least about 150%, such as at least about 200%, such as at least about 250%, such as at least about 300% of that of the native or parent GCH1. Suitable assays are provided in the Examples, e.g., Examples 1, 6 and 7. For example, the PheH may be C. violaceum PheH (SEQ ID NO:58) or a functionally active variant, homolog or fragment thereof; the PCD may, for example, be C. violaceum PCD (SEQ ID NO:21) or a functionally active variant, homolog or fragment thereof, and the assay conducted in the presence of about 100 mg/L L-phenylalanine. Alternatively, the PheH may be a TPH also having PheH activity, such as Homo sapiens TPH2 (SEQ ID NO:3) or a functionally active variant, homolog or fragment thereof, such as a TPH variant comprising or consisting of the amino acid sequence of SEQ ID NO:13 with E2K, N97I and P99C mutations introduced.

In another aspect, the invention provides a method of selecting and, optionally, producing, a variant GCH1, the method comprising the steps of (a) preparing a population of variants of a parent GCH1;
(b) preparing a population of microbial cells, each expressing a variant GCH1, a PCD, and at least one hydroxylase selected from a TPH, a TH, and a PheH;
(c) analyzing the population of microbial cells for hydroxylation of a substrate for the hydroxylase as compared to a control, optionally wherein the control is a microbial cell expressing parent GCH1, the PCD and the at least one hydroxylase;
(d) selecting at least one variant GCH1 which provides increased hydroxylation as compared to the control; and
(e) optionally, producing the variant GCH1 by recombinant expression in a host cell.

Optionally, the method may comprise features of other embodiments herein which describe activity testing of variant E. coli GCH1. Suitable sources of parent GCH1 include, for example, those listed in Table 1, for example Homo sapiens or S. cerevisiae GCH1. The invention also provides a variant GCH1 obtained or obtainable from the method.

A mutated GCH1 according to any aspect or embodiment herein can, for example, be expressed from an exogenously introduced nucleic acid sequence. In one embodiment, the mutated GCH1 is expressed from a nucleic acid sequence integrated into the chromosome. Alternatively, the native gene can be mutated in situ, i.e., in the chromosome of the microbial cell, after which the mutated GCH1 is expressed from the mutated gene. In some embodiments, the microbial cell expresses a lower level of native GCH1 than the (native) parent cell, e.g., by downregulating, deleting or otherwise inactivating the native GCH1 gene (e.g., folE).

In an alternative embodiment, the recombinant microbial cell comprises an overexpressed GCH1 selected from the GCH1 enzymes listed in Table 1, optionally with a mutation corresponding to D97V, M99I, N170K, N170D, V179A, V179M, T198I, T198S, L200P, S207R, H212R, E213K, F214S, L215Q, L215P or H221R, or a combination thereof.

In a preferred embodiment, the nucleic acid sequence encoding the GCH1 is operably linked to a strong promoter, providing for high expression levels of the GCH1. Even more preferably, the nucleic acid sequence encoding the GCH1 has the 5'-end sequence atgaaa, encoding MK. In a specific embodiment, the nucleic acid sequence is operatively linked to a Trc promoter, optionally comprising the nucleic acid sequence of SEQ ID NO:53. Without being limited to theory, the mutation encoding for the N-terminal Met-Lys residues provides for an increased activity and/or expression level of the GCH1.

In the recombinant host cell, the GCH1 is typically sufficiently expressed so that an increased level of 5HTP production from L-tryptophan can be detected in the assay according to Example 2, Example 3 or Example 4, i.e., in an E. coli host cell comprising a Homo sapiens TPH2 fragment or variant as described herein or a Schistosoma mansoni TPH, and a C. violaceum PCD, as compared to the microbial host cell prior to transformation with a heterologous GCH1 or prior to the introduction of a GCH1, optionally in the presence of added tryptophan substrate. Alternatively, the expression level of the specific GCH1 enzyme can be evaluated by proteomic analysis, according to methods known in the art.

Downstream Enzymes

In some embodiments, particularly when the monooxygenase is a TH, the recombinant microbial cell can further comprise nucleic acid sequences, e.g., heterologous, encoding a dopa decarboxylase, a tyramine oxidase and an alcohol dehydrogenase for production of hydroxytyrosol; e.g., as described by Satoh et al. (2012).

In some embodiments, particularly when the monooxygenase is a TPH and serotonin, N-acetyl-serotonin or melatonin is a desired end-product, the recombinant microbial cell can further comprise heterologous nucleic acid sequences encoding a 5HTP decarboxylase (ADDC), a serotonin acetyltransferase (AANAT) and/or an acetylserotonin O-methyltransferase (ASMT):

1. 5HTP Decarboxylase:

The last step in the serotonin biosynthesis via a 5HTP intermediate, the conversion of 5HTP to serotonin, is in animal cells catalyzed by a 5HTP decarboxylase, which is an aromatic L-amino acid decarboxylase (AADC) typically classified as EC 4.1.1.28. Suitable 5HTP decarboxylases include any tryptophan decarboxylase (TDC) capable of catalyzing the referenced reaction. TDC participates in the plant serotonin biosynthesis pathway, where tryptophan decarboxylase (TDC) catalyzes the conversion of tryptophan to tryptamine, which is then converted into serotonin in a reaction catalyzed by tryptamine 5-hydroxylase (T5H). TDC likewise belongs to the aromatic amino acid decarboxylases categorized in EC 4.1.1.28, and can be able to convert 5HTP to serotonin and carbon dioxide (see, e.g., Park et al., Biosci. Biotechnol. Biocem. 2008; 72(9):2456-2458.2008, and Gibson et al., J. Exp. Bot. 1972; 23(3):775-786), and thus function as a 5HTP decarboxylase. Exemplary nucleic acids encoding ADDC enzymes for use in aspects and embodiments of the present invention include, but are not limited to, those encoding the 5HTP decarboxylases listed in Table 1, as well as functionally active variants, homologs and fragments thereof. In some embodiments, particularly where it is desired to also promote serotonin formation from a tryptamine substrate in the same recombinant cell, an enzyme capable of catalyzing both the conversion of tryptophan to tryptamine and the conversion of 5HTP to serotonin can be used. For example, rice TDC and tomato TDC can function also as a 5HTP decarboxylase, an activity which can be promoted by the presence of pyridoxal phosphate (e.g., at a concentration of about 0.1 mM) (Park et al., 2008).

Suitable assays for testing serotonin production by a 5HTP decarboxylase in a recombinant microbial host cell are provided in, or can be adapted from, e.g., Park et al. (2008) and Park et al., Appl Microbiol Biotechnol 2011; 89(5):1387-1394. For example, these assays can be adapted to test serotonin production by a 5HTP decarboxylase (e.g., a TDC), either from 5HTP or, in case the microbial cell comprises an L-tryptophan hydroxylase, from L-tryptophan (or simply a carbon source). In one exemplary embodiment, the recombinant microbial cell produces at least 5%, such as at least 10%, such as at least 20%, such as at least 50%, such as at least 100% or more serotonin than the recombinant cell without transformation with 5HTP decarboxylase enzyme, i.e., a background value.

2. Serotonin Acetyltransferase (AANAT):

In one aspect, the recombinant microbial cell further comprises an exogenous nucleic acid sequence encoding a serotonin acetyltransferase, also known as serotonin —N-acetyltransferase, arylalkylamine N-acetyltransferase and AANAT, and typically classified as EC 2.3.1.87. AANAT catalyzes the conversion of acetyl-CoA and serotonin to CoA and N-Acetyl-serotonin. Exemplary nucleic acids encoding AANAT enzymes for use in aspects and embodiments of the present invention include, but are not limited to, those encoding the AANATs shown in Table 1, as well as functionally active variants, homologs or fragments thereof.

Suitable assays for testing N-acetylserotonin production by an AANAT in a recombinant microbial host cell are described in, e.g., Thomas et al., Analytical Biochemistry 1990; 184:228-34.

3. Acetylserotonin O-Methyltransferase (ASMT):

In one aspect, the recombinant cell further comprises an exogenous nucleic acid encoding an acetylserotonin O-methyltransferase or ASMT, typically classified as EC 2.1.1.4. ASMT catalyzes the last reaction in the production of melatonin from L-tryptophan, the conversion of N-acetylserotonin and S-adenosyl-L-methionine (SAM) to Melatonin and S-adenosyl-L-homocysteine (SAH). SAH can then be recycled back to SAM via the S-adenosyl-L-methionine cycle in microbial cells where the S-adenosyl-L-methionine cycle is native (or exogenously added) and constitutively expressed, such as, e.g., in E. coli. Exemplary nucleic acids encoding ASMT enzymes for use in aspects and embodiments of the present invention include, but are not limited to, those encoding ASMTs shown in Table 1, as well as functionally active variants, homologs or fragments thereof. Suitable assays for testing melatonin production by an ASMT in a recombinant microbial host cell have been described in, e.g., Kang et al. J. Pineal Res. 2011:50; 304-309, which is hereby incorporated by reference in its entirety.

Nucleic Acids and Vectors

In other aspects, there is provided nucleic acid sequences and vectors comprising such nucleic acid sequences. For example, a nucleic acid sequence encoding an enzyme or other protein activity listed in Table 1 or a fragment or variant thereof as described in any aspect or embodiment herein may encode an amino acid sequence that is homologous (i.e., native) or heterologous to the recombinant host cell in question, e.g., a variant or fragment of an endogenous amino acid sequence.

Also provided are one or more vectors comprising nucleic acid sequences according to the above aspects and embodiments, e.g., encoding one or more of, such as one, two, three, four, five, six or all of, a monooxygenase (e.g., TPH/TH/PheH), PCD, GCH1, 5HTP decarboxylase, AANAT and ASMT, optionally wherein the GCH1 is mutant FolE as described herein and/or the TPH is Schistosoma mansoni or variant Homo sapiens TPH2 as described herein.

In a particular aspect, the invention provides a nucleic acid sequence comprising a Trc promoter and a DNA coding sequence encoding an enzyme or other protein, wherein the 3'-end of the Trc promoter is operably, preferably directly, linked to the 5'-end of the DNA coding sequence, and wherein the 5'-end sequence of the DNA coding sequence is atgaaa.

In one embodiment, there is provided a vector comprising such a nucleic acid sequence.

In one embodiment, there is provided a method for expressing an enzyme or other protein, comprising transforming an E. coli host cell with the vector of the preceding embodiment, expressing the enzyme or other protein; and, optionally, harvesting the enzyme or other protein.

Preferably, in any of the preceding embodiments, the Trc promoter is directly linked to the DNA coding sequence. Most preferably, the nucleic acid sequence comprises SEQ ID NO:53, i.e., the DNA sequence of a Trc promoter directly linked to atgaaa. The N-terminal amino acids of the enzyme or other protein encoded by the DNA coding sequence are MK (Met-Lys). Accordingly, the enzyme or other protein encoded by the DNA coding sequence may be a native enzyme or protein whose N-terminal amino acid sequence is MK. Alternatively, the enzyme or other protein may be a variant or fragment of a native enzyme or protein, wherein the N-terminal amino acid sequence is modified to MK, e.g., introducing an X2K amino acid substitution, where "X" represents the amino acid adjacent to the N-terminal methionine residue. In one embodiment, the enzyme encoded is one that is listed in Table 1 or a functionally active fragment or variant thereof, wherein the N-terminal amino acids are MK.

In one embodiment, there is provided a method of producing a recombinant variant of a parent enzyme or other parent protein in an *E. coli* host cell, wherein the N-terminal amino acid sequence of the parent enzyme or other parent protein is MX, wherein X is not lysine, the method comprising the steps of:

(a) preparing a vector comprising a Trc promoter operably, preferably directly, linked to a DNA coding sequence encoding a variant of the parent enzyme or other variant protein which has an X2K amino acid substitution or an insertion of a K between the N-terminal M and X, wherein the 5'-end sequence of the DNA coding sequence is atgaaa;

(b) transforming an *E. coli* host cell with the vector of (a);

(c) expressing the recombinant variant of the parent enzyme or other parent protein in the *E. coli* host cell; and, (d) optionally, harvesting the recombinant variant of the parent enzyme or other parent protein.

In one embodiment, the only different between the parent and variant enzyme or protein is the X2K amino acid substitution or the insertion of a K between the N-terminal M and X. This method may provide an increased expression level of the variant enzyme/protein as compared to the parent enzyme/protein in *E. coli* cells under conditions that are otherwise the same or similar.

The specific design of the vector according to any aspect or embodiment depends on, e.g., whether host cell already endogenously produces sufficient amounts of one or more of the enzymes. For example, in an *E. coli* host cell, it may not be necessary to introduce the nucleic acid sequence encoding a mutated FolE sequence exogenously, in case the native gene can be mutated in situ to introduce the mutation (see Example 1). Additionally, for transformation of a particular host cell, two or more vectors with different combinations of the enzymes used in the present invention can be applied. The vector can be a plasmid, phage vector, viral vector, episome, an artificial chromosome or other polynucleotide construct, and may, for example, include one or more selectable marker genes and appropriate expression control sequences.

Generally, regulatory control sequences are operably linked to the encoding nucleic acid sequences, and include constitutive, regulatory and inducible promoters, transcription enhancers, transcription terminators, and the like which are well known in the art. The encoding nucleic acid sequences can be operationally linked to one common expression control sequence or linked to different expression control sequences, such as one inducible promoter and one constitutive promoter.

The procedures used to ligate the various regulatory control and marker elements with the encoding nucleic acid sequences to construct the vectors of the present invention are well known to one skilled in the art (see, e.g., Sambrook et al., 2012, supra). In addition, methods have recently been developed for assembling of multiple overlapping DNA molecules (Gibson et al., 2008) (Gibson et al., 2009) (Li & Elledge, 2007), allowing, e.g., for the assembly multiple overlapping DNA fragments by the concerted action of an exonuclease, a DNA polymerase and a DNA ligase.

The promoter sequence is typically one that is recognized by the intended host cell. For an *E. coli* host cell, suitable promoters include, but are not limited to, the lac promoter, the T7 promoter, pBAD, the tet promoter, the Lac promoter, the Trc promoter, the Trp promoter, the recA promoter, the λ (lamda) promoter, and the PL promoter. Preferred promoters include the Trc promoter. For *Streptomyces* host cells, suitable promoters include that of *Streptomyces coelicolor agarase* (dagA). For a *Bacillus* host cell, suitable promoters include the sacB, amyL, amyM, amyQ, penP, xylA and xylB. Other promoters for bacterial cells include prokaryotic beta-lactamase (Villa-Kamaroff et al., 1978, Proceedings of the National Academy of Sciences USA 75: 3727-3731), and the tac promoter (DeBoer et al., 1983, Proceedings of the National Academy of Sciences USA 80: 21-25). For an *S. cerevisiae* host cell, useful promoters include the TEF1, HXT7, TDH3, ENO-1, GAL1, ADH1, ADH2, GAP, TPI, CUP1, PHO5 and PGK, such as PGK1 promoters. Other useful promoters for yeast host cells are described by Romanos et al., 1992, Yeast 8: 423-488. Still other useful promoters for various host cells are described in "Useful proteins from recombinant bacteria" in Scientific American, 1980, 242: 74-94; and in Sambrook et al., 2012, supra.

In one embodiment, one or more or all of the exogenous nucleic acids is each under the control of a strong promoter, e.g., each separately selected from T7, lac, trac and PL in an *E. coli* host cell, and each separately selected from PGK1, TEF1, HXT7 and TDH3 in an *S. cerevisiae* host cell.

A transcription terminator sequence is a sequence recognized by a host cell to terminate transcription, and is typically operably linked to the 3' terminus of an encoding nucleic acid sequence. Suitable terminator sequences for *E. coli* host cells include the T7 terminator region. Suitable terminator sequences for yeast host cells such as *S. cerevisiae* include CYC1, PGK, GAL, ADH, AOX1 and GAPDH. Other useful terminators for yeast host cells are described by Romanos et al., 1992, supra.

A leader sequence is a non-translated region of an mRNA which is important for translation by the host cell. The leader sequence is typically operably linked to the 5' terminus of a coding nucleic acid sequence. Suitable leaders for yeast host cells include *S. cerevisiae* ENO-1, PGK, alpha-factor, ADH2/GAP, TEF, and Kozak sequence.

A polyadenylation sequence is a sequence operably linked to the 3' terminus of a coding nucleic acid sequence which, when transcribed, is recognized by the host cell as a signal to add polyadenosine residues to transcribed mRNA. Useful polyadenylation sequences for yeast host cells are described by Guo and Sherman, 1995, Mol Cell Biol 15: 5983-5990.

A signal peptide sequence encodes an amino acid sequence linked to the amino terminus of an encoded amino acid sequence, and directs the encoded amino acid sequence into the cell's secretory pathway. In some cases, the 5' end of the coding nucleic acid sequence may inherently contain a signal peptide coding region naturally linked in translation reading frame, while a foreign signal peptide coding region may be required in other cases. Useful signal peptides for yeast host cells can be obtained from the genes for *S. cerevisiae* alpha-factor and invertase. Other useful signal peptide coding regions are described by Romanos et al., 1992, supra. An exemplary signal peptide for an *E. coli* host cell can be obtained from alkaline phosphatase. For a *Bacillus* host cell, suitable signal peptide sequences can be obtained from alpha-amylase and subtilisin. Further signal peptides are described by Simonen and Palva, 1993, Microbiological Reviews 57: 109-137.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tec, and tip operator systems. For example, one or more promoter sequences can be under the control of an IPTG inducer, initiating expression of the gene once IPTG is added. In yeast, the ADH2 system or GAL1 system may be used. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the respective encoding nucleic acid sequence would be operably linked with the regulatory sequence.

The choice of the vector will typically depend on the compatibility of the vector with the host cell into which the vector is to be introduced. The vectors may be linear or closed circular plasmids. The vector may also be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. The selectable marker genes can, for example, provide resistance to antibiotics or toxins, complement auxotrophic deficiencies, or supply critical nutrients not in the culture media, and/or provide for control of chromosomal integration. Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

The vectors of the present invention may also contain one or more elements that permit integration of the vector into the host cell genome or autonomous replication of the vector in the cell independent of the genome. For integration into the host cell genome, the vector may rely on an encoding nucleic acid sequence or other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. The integrational elements may, for example, non-encoding or encoding nucleotide sequences. The vector may be integrated into the genome of the host cell by non-homologous recombination. For example, for integration into an *E. coli* chromosome, the vector may contain elements directing integration of the nucleic acid sequences using the Tn7 site-specific integration method according to McKenzie G and Nancy LC (2006).

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo. Examples of bacterial origins of replication are the origins of replication of plasmids pBR322, pUC19, pACYC177, and pACYC184 permitting replication in *E. coli*, and pUB110, pE194, pTA1060, and pAMβi permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of the nucleic acid sequence encoding the enzyme or protein of interest may be inserted into the host cell to increase production of the gene product. An increase in the copy number of the encoding nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the sequence, can be selected for by cultivating the cells in the presence of the appropriate selectable agent.

Recombinant Cells

The present invention relates to recombinant microbial cells comprising a monooxygenase and a PCD. Optionally, one or both enzymes are heterologous to the microbial cell. It has now been discovered that the production of 5HTP, L-DOPA, tyrosine (e.g., m-tyrosine) and other compounds that are the products of monooxygenase-catalyzed reactions in such recombinant microbial cells can be optimized by modifications such as omitting certain enzymes and/or introducing certain mutations in certain endogenous or exogenous nucleic acid sequences. These modifications include mutations in the monooxygenase (e.g., a TPH) or in a GTP cyclohydrolase 1 (GCH1) as described in previous embodiments, and/or mutations in YnbB, mutations, downregulation or deletion of tnaA, and combinations of any two or more such modifications.

The aforementioned mutations can advantageously be combined in the recombinant host cell, particularly when the host cell is of the *Escherichia* genus, such as an *E. coli* cell. Any monooxygenase, e.g., an amino acid hydroxylase, can be used. In some embodiments, however, the monooxygenase is a TPH, a TH or a PheH. So, in one embodiment, the recombinant microbial cell comprises a PCD and one or more of (a) a nucleic acid sequence encoding *E. coli* GTP cyclohydrolase 1 (folE) or a functionally active variant, homolog or fragment thereof, comprising a mutation as described herein, e.g., in T198, F214, V179, M99 and/or L200; and (b) a nucleic acid sequence encoding a mammalian (such as a *Homo sapiens*) TPH or *Schistosoma mansoni* TPH or a functionally active variant, homolog or fragment thereof. In preferred embodiments, the mutation in FolE is selected from T198I, T198S, F214S, V179A, M99I and L200P and/or the TPH comprises or consists of the residues corresponding to residues E147 to T460 of *Homo sapiens* TPH2, an N-terminal methionine residue, and a mutation corresponding to E147K, N242I or P244D/P244C or a combination thereof such as N242I and P244D.

In one embodiment, the recombinant microbial cell, particularly when the cell is an *E. coli* cell, also or alternatively comprises an YnbB or a functionally active variant, homolog or fragment thereof, comprising a mutation in the residue corresponding to V197. Preferably, the mutation in V197 is V197A. The *E. coli* YnbB sequence is provided in SEQ ID NO:52.

In one embodiment, particularly when the monooxygenase is a TPH, the recombinant microbial cell of the invention comprises a deletion or downregulation of an endogenous gene encoding an enzyme providing for degradation of tryptophan, e.g., a tryptophanase (EC 4.1.99.1).

In one embodiment, the microbial cell is genetically modified, typically mutated, to downregulate or delete tryptophanase activity. Tryptophanase or tryptophan indole-lyase (EC 4.1.99.1), encoded by the tnaA gene in *E. coli*, catalyzes the hydrolytic cleavage of L-tryptophan to indole, pyruvate and $NH4^+$. Active tryptophanase consists of four identical subunits, and enables utilization of L-tryptophan as sole source of nitrogen or carbon for growth together with a tryptophan transporter encoded by tnaC gene. Tryptophanase is a major contributor towards the cellular L-cysteine desulfhydrase (CD) activity. In vitro, tryptophanase also catalyzes α, β elimination, β replacement, and α hydrogen exchange reactions with a variety of L-amino acids. Tryptophan degradation mechanisms are known to also exist in other microorganisms. For instance, in *S. cerevisiae*, there are two different pathways for the degradation of tryptophan (The Erlich pathway and the kynurenine pathway, respectively), involving in their first step the aromatic amino acid aminotransferase ARO8, ARO9, ARO10, and/or BNA2 genes.

Accordingly, reducing tryptophan degradation can be achieved by, e.g., a site-directed mutation in or deletion of a gene encoding a tryptophanase, such as the tnaA gene (in *E. coli* or other organisms such as *Enterobacter aerogenes*) (Uniprot P0A853), or the kynA gene (in *Bacillus* species) (Uniprot Q736W5), or one or more of the ARO8 (Uniprot P53090), ARO9 (Uniprot P38840), ARO10 (Uniprot Q06408) and BNA2 (Uniprot P47125) genes (in *S. cerevisiae*). In one embodiment, the ARO9 gene is downregulated, optionally deleted. Alternatively, tryptophanase activity can be reduced reducing the expression of the gene by introducing a mutation in, e.g., a native promoter element, or by adding an inhibitor of the tryptophanase.

In addition, as discovered by the present inventor, for the purpose of achieving 5HTP production in a microbial cell, it is not necessary that the cell comprises exogenous nucleic acid sequences providing for the expression of dihydropteridine reductase (DHPR) and/or dihydromonapterin reductase (DHMR). It is further not necessary for the cell to comprise exogenous nucleic acid sequences providing for the expression of 6-pyruvoyl-tetrahydropterin synthase (PTPS or PTS) and/or sepiapterin reductase (SPR). Without being limited to theory, this provides for increased metabolic resources being available for the expression of TPH and PCD, the production of 5HTP production, or both, thus improving the yield of 5HTP.

DHPR is typically classified as EC 1.5.1.34, and can convert quinonoid dihydrobiopterin (q-$H_2$—BPt or DHB) to tetrahydrobiopterin ($H_4$—BPt or THB) in the presence of cofactor NADH. DHMR is typically classified as EC 1.5.1.50 and can convert 7,8-dihydromonapterin to 5,6,7,8-tetrahydromonapterin. The endogenous *E. coli* DHMR gene is designated folM. So, in one embodiment, the recombinant microbial cell of any one of the preceding aspects or embodiments does not comprise one or both of a heterologous or overexpressed endogenous DHPR and DHMR. In a specific embodiment, the microbial cell does not comprise an exogenous nucleic acid sequence, such as a heterologous or overexpressed endogenous nucleic acid sequence, encoding a DHPR or a DHMR. In one embodiment, the microbial cell does not comprise a nucleic acid encoding a DHPR or a DHMR. In an additional or alternative embodiment, the microbial cell does not comprise a nucleic acid sequence encoding *E. coli* oxygen-insensitive nitroreductase (NfsB).

PTS is typically classified as EC 4.2.3.12, and can convert 7,8-dihydroneopterin 3'-triphosphate (($H_2$—$N_3$P or DHP) to 6-pyruvoyltetrahydropterin ($H_4$-PPt or 6PTH). SPR is typically classified as EC 1.1.1.153, and can convert 6PTH to THB in the presence of its cofactor NADPH.

So, in one embodiment, the recombinant microbial cell of any preceding aspect or embodiment does not comprise one or both of a heterologous or overexpressed endogenous PTPS and SPR. In a specific embodiment, the microbial cell does not comprise an exogenous nucleic acid sequence, such as a heterologous or overexpressed endogenous nucleic acid sequence, encoding a PTS or an SPR. In another specific embodiment, the microbial cell does not comprise a nucleic acid sequence encoding a PTS or an SPR.

In yet another embodiment, the recombinant microbial cell of any preceding aspect or embodiment does not comprise any heterologous or overexpressed endogenous DHPR, DHMR, PTPS or SPR. In a specific embodiment, the microbial cell does not comprise exogenous nucleic acid sequences, such as heterologous or overexpressed endogenous nucleic acid sequences, encoding a DHPR, a DHMR, PTS or SPR. In another specific embodiment, the microbial cell does not comprise nucleic acid sequences encoding a DHPR, a DHMR, a PTS or an SPR.

TABLE 1

Examples of enzymes and amino acid sequences

| Name (EC #) | Species | SEQ ID # (GenBank or UniProtKB #) |
| --- | --- | --- |
| L-tryptophan hydroxylase (EC 1.14.16.4) (TPH) | *Oryctolagus cuniculus* TPH1 ("ocTPH") | 1 (P17290-1, v2) |
| | *Homo sapiens* TPH1 ("hsTPH1") | 2 (NP_004170.1) |
| | *Homo sapiens* TPH2 ("hsTPH2") | 3 (NP_775489.2, Q8IWU9) |
| | *Bos taurus* ("bsTPH") | 4 |
| | *Sus scrofa* ("scTPH") | 5 |
| | *Gallus gallus* ("ggTPH") | 6 (NP_990287.1) |
| | *Mus musculus* ("mmTPH") | 7 (NP_033440.1) |
| | *Equus caballus* ("ecTPH") | 8 (NP_001075252.1) |
| | *Schistosoma mansoni* ("scTPH") | 9 (AAD01923.1) |
| | *Homo sapiens* TPH2, insert (+6) | 10 |

TABLE 1-continued

Examples of enzymes and amino acid sequences

| Name (EC #) | Species | SEQ ID # (GenBank or UniProtKB #) |
| --- | --- | --- |
| | Homo sapiens TPH2, truncated ((45-471) + 20) | 11 |
| | Homo sapiens TPH2, truncated (45-471) | 12 |
| | Homo sapiens TPH2, truncated (147-460 + N-terminal methionine) | 13 |
| GTP cyclohydrolase I (EC 3.5.4.16) (GCH1) | Homo sapiens | 14 (P30793) |
| | Mus musculus | 15 (Q3U7P6) |
| | E. coli (FolE) | 16 (P0A6T5) |
| | S. cerevisiae | 17 (P51601) |
| | Bacillus subtilis | 18 (G4EUF8) |
| | Streptomyces avermitilis | 19 (Q82EE8) |
| | Salmonella typhii | 20 (T2PZ12) |
| pterin-4-alpha-carbinolamine dehydratase (EC 4.2.1.96) (PCD) | Chromobacterium violaceum | 21 (Q7NVH7) |
| | Pseudomonas aeruginosa | 22 (P43335) |
| | Bacillus cereus var. anthracis | 23 (D8GWB2) |
| | Lactobacillus ruminis ATCC 25644 | 25 (E7FT68) |
| | Rhodobacteraceae bacterium HTCC2083 | 26 (B6B2H7) |
| | Homo sapiens | 27 (P61457) |
| 5HTP decarboxylase (EC 4.1.1.28) (ADDC) | Acidobacterium capsulatum | 28 (WP_015898075.1) |
| | Rattus norvegicus | 29 (XP_006251536.1) |
| | Sus scrofa | 30 (NP_999019.1) |
| | Homo sapiens | 31 (P20711-1, v2) |
| | Capsicum annuum | 32 (NP_001312016.1) |
| | Drosophila caribiana | 33 (AAM80956.1) |
| | Maricaulis maris (strain MCS10) | 34 (ABI65701.1) |
| | Oryza sativa subsp. Japonica | 35 (XP_015648768.1) |
| | Pseudomonas putida S16 | 36 (WP_013972057.1) |
| | Catharanthus roseus | 37 (P17770-1, v1) |
| serotonin acetyltransferase (EC 2.3.1.87 or 2.3.1.5) (AANAT) | Chlamydomonas reinhardtii | 38 (BAH10512.1) |
| | Bos Taurus | 39 (DAA18183.1) |
| | Bos Taurus A55P | 40 |
| | Gallus gallus | 41 (NP_990489.1) |
| | Homo sapiens | 42 (NP_001079.1) |
| | Mus musculus | 43 (XP_011246971.1) |
| | Oryctolagus cuniculus | 44 (XP 008249128.1) |
| | Ovis aries | 45 (NP_001009461.1) |
| acetylserotonin O-methyltransferase (EC 2.1.1.4) (ASMT) | Oryza sativa | 46 (XP 015610997.1) |
| | Homo sapiens | 47 (P46597-1, v1) |
| | Bos Taurus | 48 (P10950-1, v2) |
| | Rattus norvegicus | 49 (NP_653360.2) |
| | Gallus gallus | 50 (NP_990674.1) |
| | Macaca mulatta | 51 (NP_001028112.1) |
| | Ocimum basilicum | Q9XGV9-1, v1 |
| | Takifugu rubripes | (XP_011609423.1) |
| | Elephantulus edwardii | (XP_006902482.1) |
| | Chromobacterium violaceum | (WP_011135808.1) |
| | Desulfotomaculum kuznetsovii DSM 6115 | (YP_004515712.1) |
| | Xenopus (Silurana) tropicalis | (NP_001011409.1) |
| | Pseudomonas fluorescens | (WP_019095725.1) |
| | Candidatus Solibacter usitatus | (WP_011682595.1) |
| | Fenneropenaeus chinensis | (AAZ66373.1) |
| | Arabidopsis thaliana | (NP_200227.1) |
| Tyrosine hydroxylase (TH) (EC 1.14.16.2) | Rattus norvegicus | 52 (NP_036872.1) |
| | Homo sapiens | 54 (P07101) |
| | Mus musculus | 55 (P24529) |
| | Bos taurus | 56 (P17289) |
| | Gallus gallus | 57 (Q9PU40) |
| Phenylalanine hydroxylase (PheH) (EC 1.14.16.1, EC 1.14.16.7) | Chromobacterium violaceum | 58 (P30967) |
| | Xanthomonas campestris pv. Viticola | 59 (A0A077SF23) |
| | Pseudomonas aeruginosa | 60 (P43334) |
| | Pseudomonas putida | 61 (Q6EMJ5) |
| | Homo sapiens | 62 (P00439) |
| | Mus musculus | 63 (P16331) |
| | Streptomyces coeruleorubidus | 64 (F5BFC8) |

Variants or homologs of any one or more of the enzymes and other proteins listed in Table 1, having the referenced activity and a sequence identity of at least 30%, such as at least 50%, such as at least 60%, such as at least 70%, such as at least 80%, such as at least 90%, such as at least 91%, 92%, 93%, 94%, 95%, 96%, 97% or 98%, such as at least 99%, over at least the catalytically active portion, optionally over the full length, of the reference amino acid sequence in its mature form, excluding signal peptide sequences and the like, are also contemplated. The variant or homolog may comprise, for example, 2, 3, 4, 5 or more, such as 10 or more, amino acid substitutions, insertions or deletions as compared to the reference amino acid sequence in its mature form. In particular conservative substitutions are considered. These are typically within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In: The Proteins, Academic Press, New York. The most commonly occurring exchanges are Ala to Ser, Val to lie, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to lie, Leu to Val, Ala to Glu, and Asp to Gly. Homologs, such as orthologs or paralogs, having the desired activity can be identified in the same or a related animal or microbial species using the reference sequences provided and appropriate activity testing. Specific enzyme variants are exemplified herein.

In a particularly preferred embodiment, the variant of an amino acid sequence in Table 1 has an X2K amino acid substitution, where "X" represents the amino acid adjacent to the N-terminal methionine residue.

The recombinant host cell is typically prepared by introducing, typically via transformation, one or more vectors as described herein, using standard methods known in the art (see, e.g., Sambrook et al., 2012, supra). The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thome, 1987, Journal of Bacteriology 169: 5771-5278).

As described above, the vector, once introduced, may be maintained as a chromosomal integrant or as a self-replicating extra-chromosomal vector.

Preferably, for transformation of an *E. coli* or other bacterial host cell, the vectors are designed as follows: A lac promoter is used to control the expressions of a gene or an artificial operon containing up to three genes connected with a linker sequence, in order to express the genes at a suitable level so that the introduction of heterologous genes/pathways do not overdraw substrates or energy in the host cell. In one particular embodiment, the recombinant microbial cell, preferably a bacterial cell, is transformed according to a strategy outlined in the Examples.

Preferably, for transformation of a yeast host cell such as *S. cerevisiae*, the heterologous genes are integrated onto chromosome using a homologous recombination based method (Mikkelsen et al., 2012). As compared with gene expression based on plasmids, the chromosomal integrated genes can be expressed with higher fidelity and resulted in better protein translation, in particular for multiple gene co-expression systems.

The transformation can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product, including those referred to above and relating to measurement of 5HTP production. Expression levels can further be optimized to obtain sufficient expression using methods well known in the art and as disclosed herein.

Tryptophan, tyrosine and phenylalanine production takes place in all known microorganisms by a single metabolic pathway (Somerville, R. L., Herrmann, R. M., 1983, Amino acids, Biosynthesis and Genetic Regulation, Addison-Wesley Publishing Company, U.S.A.: 301-322 and 351-378; Aida et al., 1986, Bio-technology of amino acid production, progress in industrial microbiology, Vol. 24, Elsevier Science Publishers, Amsterdam: 188-206). The recombinant microbial cell of the invention can thus be prepared from any microbial host cell, using recombinant techniques well known in the art (see, e.g., Sambrook et al., 2012, supra, and Ausubel et al. (1991), supra. Preferably, the host cell is tryptophan, tyrosine and/or phenylalanine autotrophic (i.e., capable of endogenous biosynthesis of the substrate of the oxidation reaction of interest), grows on synthetic medium with suitable carbon sources, and expresses a suitable RNA polymerase (such as, e.g., T7 polymerase).

GTP cyclohydrolase I (such as, e.g. FolE)-catalyzed pterin biosynthesis takes place in many organisms including both prokaryotes and eukaryotes. The recombinant cell of the invention can thus be prepared from any hosts, using recombinant techniques well known in the art (see, e.g., Sambrook et al., 2012, supra, and Ausubel et al. (1991), supra. Preferably, the host cell is capable of one, more or all of tetrahydrofolate, tetrahydrobiopterin, preQ$_0$, drosopterin, aurodrosopterin or tetrahydromonapterin biosynthesis (see FIG. 1). So, for example, in one embodiment, the microbial host cell is an *E. coli* cell comprising the endogenous enzymes folE, folX, P-ase, and folM, optionally upregulated or expressed from one or more vectors.

For embodiments where the monooxygenase is a TPH and the desired end-product is serotonin, N-acetylserotonin or melatonin, the recombinant host cell is typically capable of biosynthesizing and/or regenerating the cofactors used by the enzymes in the melatonin biosynthesis pathway. In particular, the recombinant host cell is preferably capable of biosynthesizing, regenerating, or bio-synthesizing and regenerating, one or more cofactors for TPH, AANAT and ASMT. Most types of host cells (e.g., mammalian host cells, yeast host cells such as *S. cerevisiae*, bacteria such as *E. coli*, etc.) are capable of producing and regenerating acetyl-CoA and SAM; the cofactors for AANAT and ASMT, respectively. AcCoA serves as a metabolic cofactor in the AANAT reaction, but is also part of other, endogenous pathways in, e.g., microbial cells.

SAM is a principal methyl donor in various intracellular transmethylation reactions. It is synthesized in the cell through SAM synthetase from methionine and ATP, and natively generated through the SAM cycle, which consists of a methyl transferase, an S-adenosyl-L-homocysteine hydrolase, a folate transferase, and an S-adenosyl-methionine synthetase (Lee et al., Korean J. Chem. Eng. 2010, 27, 587-589). Accordingly, in the ASMT-catalyzed, last reaction in the production of melatonin from L-tryptophan, N-acetylserotonin and SAM are converted to melatonin and SAH. SAH can then be recycled back to SAM via the SAM-cycle in microbial cells where the S-adenosyl-L-methionine cycle is native (or exogenously added) and constitutively expressed, such as, e.g., in *E. coli*. The enzymes of such native pathways can also, in needed, be upregulated or expressed from an exogenously introduced vector, using well-known recombinant techniques known in text books referenced elsewhere herein. Non-limiting and exemplary nucleic acids encoding enzymes of the SAM cycle for use in aspects and embodiments of the present invention include those shown in Table 1 of WO 2015/032911 A1, which is hereby specifically incorporated by reference, including the actual amino acid sequences referred to in the table as SEQ ID numbers.

The microbial host cell for use in the present invention is typically unicellular and can be, for example, a bacterial cell, a yeast host cell, a filamentous fungal cell, or an algeal cell. Examples of suitable host cell genera include, but are not limited to, *Acinetobacter, Agrobacterium, Alcaligenes, Anabaena, Aspergillus, Bacillus, Bifidobacterium, Brevibacterium, Candida, Chlorobium, Chromatium, Corynebacteria, Cytophaga, Deinococcus, Enterococcus, Erwinia, Erythrobacter, Escherichia, Flavobacterium, Hansenula, Klebsiella, Lactobacillus, Methanobacterium, Methylobacter, Methylococcus, Methylocystis, Methylomicrobium, Methylomonas, Methylosinus, Mycobacterium, Myxococcus, Pantoea, Phaffia, Pichia, Pseudomonas, Rhodobacter, Rhodococcus, Saccharomyces, Salmonella, Sphingomonas, Streptococcus, Streptomyces, Synechococcus, Synechocystis, Thiobacillus, Trichoderma, Yarrowia* and *Zymomonas*.

In one embodiment, the host cell is bacterial cell, e.g., an *Escherichia* cell such as an *Escherichia coli* cell; a *Bacillus* cell such as a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, or a *Bacillus thuringiensis* cell; or a *Streptomyces* cell such as a *Streptomyces lividans* or *Streptomyces murinus* cell. In a particular embodiment, the host cell is an *E. coli* cell. In another particular embodiment, the host cell is of an *E. coli* strain selected from the group consisting of K12.DH1 (Proc. Natl. Acad. Sci. USA, volume 60, 160 (1968)), JM101, JM103 (Nucleic Acids Research (1981), 9, 309), JA221 (J. Mol. Biol. (1978), 120, 517), HB101 (J. Mol. Biol. (1969), 41, 459) and C600 (Genetics, (1954), 39, 440).

In one embodiment, the host cell is a fungal cell, such as, e.g., a yeast cell. Exemplary yeast cells include *Candida, Hansenula, Kluyveromyces, Pichia, Saccharomyces, Schizosaccharomyces* and *Yarrowia* cells. In a particular embodiment, the host cell is an *S. cerevisiae* cell. In another particular embodiment, the host cell is of an *S. cerevisie* strain selected from the group consisting of *S. cerevisiae* KA31, AH22, AH22R-, NA87-11A, DKD-5D and 20B-12, *S. pombe* NCYC1913 and NCYC2036 and *Pichia pastoris* KM71. The recombinant microbial cell of any one of the aspects or embodiments herein is typically a bacterial cell, a yeast cell, a filamentous fungal cell, or an algal cell. In one embodiment, the recombinant microbial cell is a cell of the *Escherichia* genus, such as an *Escherichia coli* cell. In one embodiment, the recombinant microbial is derived from a *Saccharomyces*, a *Schizosaccharomyces*, a *Corynebacterium*, a *Bacillus* or a *Streptomyces* cell.

Production of Oxidation Products and Downstream Products:

The invention also provides a method of producing various oxidation products, e.g., of aromatic amino acids, as well as various other products where such an oxidation product is an intermediate in a biosynthetic pathway. Examples of products include, but are not limited to, 5HTP, L-DOPA, tyrosine (e.g., m-tyrosine), hydroxytyrosol, melatonin, serotonin and/or N-acetyl-serotonin, comprising culturing the recombinant microbial cell of any preceding aspect or embodiment in a medium comprising a carbon source. The desired compound can then optionally be isolated or retrieved from the medium, and optionally further purified. Importantly, using a recombinant microbial cell according to the invention, the method can be carried out without adding monooxygenase substrates such as L-tryptophan, L-tyrosine or L-phenylalanine, or monooxygenase cofactor such as THB, or both, to the medium.

Also provided is a method of preparing a composition comprising one or more compounds selected from 5HTP, L-DOPA, tyrosine, hydroxytyrosol, melatonin, serotonin and/or N-acetyl-serotonin, comprising culturing the recombinant microbial cell of any preceding aspect or embodiment, isolating and purifying the compound(s), and adding any excipients to obtain the composition.

Suitable carbon sources include carbohydrates such as monosaccharides, oligosaccharides and polysaccharides. As used herein, "monosaccharide" denotes a single unit of the general chemical formula $C_x(H_2O)_y$, without glycosidic connection to other such units, and includes glucose, fructose, xylose, arabinose, galactose and mannose. "Oligosaccharides" are compounds in which monosaccharide units are joined by glycosidic linkages, and include sucrose and lactose. According to the number of units, oligosaccharides are called disaccharides, trisaccharides, tetrasaccharides, pentasaccharides etc. The borderline with polysaccharides cannot be drawn strictly; however the term "oligosaccharide" is commonly used to refer to a defined structure as opposed to a polymer of unspecified length or a homologous mixture. "Polysaccharides" is the name given to a macromolecule consisting of a large number of monosaccharide residues joined to each other by glycosidic linkages, and includes starch, lignocellulose, cellulose, hemicellulose, glycogen, xylan, glucuronoxylan, arabinoxylan, arabinogalactan, glucomannan, xyloglucan, and galactomannan. Other suitable carbon sources include acetate, glycerol, pyruvate and gluconate. In one embodiment, the carbon source is selected from the group consisting of glucose, fructose, sucrose, xylose, mannose, galactose, rhamnose, arabinose, fatty acids, glycerine, glycerol, acetate, pyruvate, gluconate, starch, glycogen, amylopectin, amylose, cellulose, cellulose acetate, cellulose nitrate, hemicellulose, xylan, glucuronoxylan, arabinoxylan, glucomannan, xyloglucan, lignin, and lignocellulose. In one embodiment, the carbon source comprises one or more of lignocellulose and glycerol. In one embodiment, the carbon source is a simple carbon source such as glucose, xylose, fructose, arabinose, galactose, mannose, glycerol, acetate, or a mixture of any thereof.

The culture conditions are adapted to the recombinant microbial host cell, and can be optimized to maximize production or melatonin or another desired compound by varying culture conditions and media components as is well-known in the art.

For a recombinant *Escherichia coli* cell, exemplary media include LB medium and M9 medium (Miller, Journal of Experiments in Molecular Genetics, 431-433, Cold Spring Harbor Laboratory, New York, 1972), optionally supplemented with one or more amino acids. When an inducible promoter is used, the inductor can also be added to the medium. Examples include the lac promoter, which can be activated by adding isopropyl-beta-thiogalacto-pyranoside (IPTG) and the GAL/BAD promoter, in which case galactose/arabinose can be added. The culturing can be carried out a temperature of about 10 to 40° C. for about 3 to 72 hours, if desired, with aeration or stirring.

For a recombinant *Bacillus* cell, culturing can be carried out in a known medium at about 30 to 40° C. for about 6 to 40 hours, if desired with aeration and stirring. With regard to the medium, known ones may be used. For example, pre-culture can be carried out in an LB medium and then the main culture using an NU medium.

For a recombinant yeast cell, Burkholder minimum medium (Bostian, K. L., et al. Proc. Natl. Acad. Sci. USA, volume 77, 4505 (1980)), SD medium containing 0.5% of Casamino acid (Bitter, G. A., et al., Proc. Natl. Acad. Sci. USA, volume 81, 5330 (1984), and Delft medium (Verduyn et al., Yeast 1992, 8, 501-517) can be used. The pH is preferably adjusted to about 5-8. For example, a synthetic medium may contain, per litre: (NH4)2SO4, 5 g; KH2PO4, 3 g; MgSO4.7H2O, 0.5 g; EDTA, 15 mg; ZnSO4.7H2O, 4.5 mg; CoCl2.6H2O, 0.3 mg; MnCl2.4H20, 1 mg; CuSO4 5H2O, 0.3 mg; CaCl2.2H2O, 4.5 mg; FeSO4.7H2O, 3 mg; NaMoO4.2H2O, 0.4 mg; H3BO3, 1 mg-KI, 0.1 mg; and 0.025 ml silicone antifoam (BDH). Filter-sterilized vitamins can be added after heat sterilization (120° C.), to final concentrations per litre of: biotin, 0.05 mg; calcium pantothenate, 1 mg; nicotinic acid, 1 mg; inositol, 25 mg; thiamine HCl, 1 mg; pyridoxine HCl, 1 mg; and para-aminobenzoic acid, 0.2 mg. The medium can then be adjusted to pH6 with KOH. Culturing is preferably carried out at about 20 to about 40° C., for about 24 to 84 hours, if desired with aeration or stirring.

In one embodiment, no L-tryptophan is added to the medium. In another embodiment, no L-tryptophan or THB is added to the medium, so that the production of melatonin or its precursors or related compounds rely on endogenously biosynthesized substrates.

Using the method for producing 5HTP, L-DOPA, tyrosine, m-tyrosine, hydroxytyrosol, melatonin, serotonin or N-acetyl-serotonin according to the invention, a yield of at least about 0.5%, such as at least about 1%, such as at least 5%, such as at least 10%, such as at least 20%, at least 30%, at least 40%, at least 50%, at least 60%, at least 70%, at least 80% or at least 90% of the theoretically possible yield can be obtained from a suitable carbon source, such as glucose.

Isolation of 5HTP, L-DOPA, tyrosine, m-tyrosine, hydroxytyrosol, melatonin, N-acetylserotonin or serotonin from the cell culture can be achieved, e.g., by separating the compound from the cells using a membrane, using, for example, centrifugation or filtration methods. The product-containing supernatant is then collected. Further purification of the desired compound can then be carried out using known methods, such as, e.g., salting out and solvent precipitation; molecular-weight-based separation methods such as dialysis, ultrafiltration, and gel filtration; charge-based separation methods such as ion-exchange chromatography; and methods based on differences in hydrophobicity, such as reversed-phase HPLC; and the like. In one embodiment, ion-exchange chromatography is used for purification of serotonin. An exemplary method for serotonin purification using cation-exchange chromatography is described in Chilcote (1974) (Clin Chem 20(4):421-423). In one embodiment, reverse-phase chromatography is used for separation and/or purification of serotonin, N-acetylserotonin, or melatonin. An exemplary method for purification of these indolamines using reversed-phase chromatography is described in Harumi et al., (1996) (J Chromatogr B 675:152-156).

Once a sufficiently pure preparation has been achieved, suitable excipients, stabilizers can optionally be added and the resulting preparation incorporated in a composition for use in preparing a product such as, e.g., a dietary supplement, a pharmaceutical, a cosmeceutical, or a nutraceutical. For a dietary supplement comprising melatonin, each serving can contain, e.g., from about 0.01 mg to about 100 mg melatonin, such as from about 0.1 mg to about 10 mg, or about 1-5 mg, such as 2-3 mg. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

Example 1

Media and Growth Conditions

All strains were maintained at 37° C. in LB (Lennox) Broth (Sigma-Aldrich), 2×YT or M9 minimum media containing 1×M9 minimal salts (BD Difco™), 2 mM MgSO$_4$, 100 µM CaCl$_2$, 500-fold diluted trace minerals (10 g/l FeCl$_3$.6H$_2$O, 2 g/l ZnSO$_4$.7H$_2$O, 0.4 g/l CuCl$_2$-2H$_2$O, 1 g/l MnSO$_4$—H$_2$O, 0.6 g/l CoCl$_2$-6H$_2$O, and 1.6 mM EDTA, pH 8.0), lx ATCC® Vitamin Supplement (ATCC MD-VS™), and 0.2% glucose (w/v). Unless stated otherwise, required supplementations were carried out as following: L-phenylalanine at 50 mg/l, L-tyrosine at 30 mg/l, folates at 10 mg/l, chloramphenicol at 25 mg/l, kanamycin at 25 mg/l, and spectinomycin at 50 mg/l.

Plasmids

The pPheH plasmid carries a codon-optimized pheH from C. violaceum. The pTHBsc plasmid carries the pcd, qDPR, pts and spr genes. The pcd and qDPR genes are from C. violaceum while the pts and spr genes are from Rattus norvegicus. The pHM1 plasmid was derived from pTHBscEv, an evolved pTHBsc plasmid isolated after PheH-dependent laboratory evolution, containing the human TpH2 gene and a sacB gene, which causes plasmid instability upon exposure to sucrose. All synthetic genes were optimized for E. coli expression.

Metabolite Analysis by LC-MS

LC-MS data was collected on OrbiTrap Fusion High Resolution Mass Spectrometer system coupled with an Ultimate 3000 UHPLC pump (Thermo, San Jose Ca). Samples were held in the autosampler at a temperature of 10.0° C. during the analysis. 1 µL Injections of the sample were made onto a Thermo HyperSil Gold PFP HPLC column, with a 3 um particle size, 2.1 mm i.d. and 150 mm long. The column was held at a temperature of 35.0° C. The solvent system used was Solvent A "Water with 0.1% formic acid" and Solvent B "Acetonitrile with 0.1% formic". The Flow Rate was 1.000 ml/min with an Initial Solvent composition of % A=95, % B=5 held until 0.50 min, the solvent composition was then changed following a Linear Gradient until it reached % A=70.0 and % B=30.0 at 1.50 min. The solvent composition was then changed following a Linear Gradient until it reached % A=5.0 and % B=95.0 at 2.00 min This was held until 2.50 min when the solvent was returned to the initial conditions and the column was re-equilibrated until 3.00 min. The first 0.25 min of the run was diverted to waste using the divert valve, following which the column eluent flowed directly into the Heated ESI probe of the MS which was held at 325° C. and a voltage of 3500 V. Data was collected in positive ion mode over the mass range 50 to 1000 m/z at a resolution of 15.000. The other MS settings were as follows, Sheath Gas Flow Rate of 60 units, Cone Gas Flow Rate of 20 units Cone Temp was 275° C.

H$_4$-BPt Optimization by Phenylalanine-Hydroxylase Dependent Laboratory Evolution Patent applications PCT/EP2013/054019 and PCT/EP2014/068967 described a method for the production of 5-hydroxytryptophan and melatonin by heterologous expression of human tryptophan hydroxylase (TpH) in *E. coli*. In addition to the desired biosynthetic genes, tetrahydrobiopterine ($H_4$—BPt) synthesis and recycling pathways consisting of four genes have to be introduced to accommodate TpH cofactor usage. Preliminary studies indicated that the rate-limiting step was human TpH turnover, possibly due to limitations in cofactor supply.

To overcome this challenge, a phenylalanine-hydroxylase dependent growth-coupled selection was designed. The key to this design was: 1) to construct an *E. coli* tyrosine auxotroph; 2) to introduce an $H_4$—BPt-dependent phenylalanine hydroxylase (PheH) that converts phenylalanine to tyrosine. The chosen PheH was from *Chromobacterium violaceum* (SEQ ID NO:58) and the chosen background strain was HL1308. The *E. coli* HL1308 strain was constructed from JW2300 of the Keio collection (Baba et al, 2006) with tyrA, recA and galE deletions further introduced according to Datsenko and Wanner (2000) or by P1 transduction. The HL1305 strain is genotypically similar to HL1308 except the tyrA deletion. Deletion of tyrA, donated by ΔtyrA, resulted in a tyrosine auxotroph while ΔfolX was necessary to inactivate de novo biosynthesis of tetrahydromonapterin known to be an electron donor of PheH from *Pseudomonas aeruginosa* (Pribat et al, 2010). The recA and galE genes were removed respectively to minimize DNA recombination during laboratory evolution and to acquire a high DNA uptake efficiency. Constitutive expression and regulations of the heterologous genes were enabled via a hybrid sequence of the native TyrR-repressible aroF promoter sequence (Cobbett, 1988) and the translation leader sequence of the rpsA gene (Tchufistova et al, 2003).

Preliminary results confirmed HL1308 strain was unable to grow without tyrosine supplementation. On the other hand, its tyrosine auxotrophy was reverted upon transformation of the pTHBsc and pPheH plasmids. The transformed strain grew at an approximately half the rate of the control strain (HL1305) with phenylalanine supplementation; however, there was no observable growth in the absence of phenylalanine.

Subsequently, the transformed strain was subjected to 280 generations of manual passage using shake flasks. The procedure was to inoculate 25 ml fresh phenylalanine supplemented M9 in a 250 ml flask to an initial density which was expected to reach an $OD_{600}$ of 0.2-0.4 after 24 hour of incubation in an orbital 31 IDS shaker (Labnet) at 37° C. and 250 rpm. This serial transfer was repeated for 16 days. The initial phenylalanine concentration was 50 mg/l and was lowered to 5 mg/l starting from day 7. Colonies were isolated at Day 6 and Day 16 and their growth rates were determined.

Adapted isolates from the high phenylalanine conditions displayed a wide range of growth response from barely growth to a growth rate comparable to HL1305 in the presence of 50 mg/I of phenylalanine. This result was in contrast to the ones recovered from the low phenylalanine environment whereas all strains exhibited significant improvement in growth with a median rate of $0.5 \pm 0.03$ $h^{-1}$ and all were able to propagate in M9 without phenylalanine supplementation. The wider distribution in the growth rates of high-phenylalanine adapted isolates led us to hypothesize that certain strains in the population were evolved to become a tyrosine secretor when an excess amount phenylalanine was present. We examined the hypothesis by feeding 0.5 g/l of phenylalanine to the best-grown strain, THB402F3C9, and confirmed ~0.1 g/l of tyrosine was secreted after overnight growth.

Plasmids originated from adapted isolates were sequenced. It appeared the pTHBsc plasmid from all isolates lacked the $H_4$—BPt biosynthesis and recycling genes except pcd thus all were $H_4$—BPt null strains. In addition, there were neither mutations presented in the pheH and pcd genes nor on the non-translational regions of the plasmids. Combining both evidences, it was reasoned *E. coli* cells must have repurposed its own metabolism to fulfil PheH cofactor requirement during adaptation and pterine-4α-carbinolamine dehydratase encoded by pcd was the only additional requirement.

A series of deletion mutants were made to elucidate possible native PheH cofactor in *E. coli*. Since folic acids and 6-carboxy-tetrahydropterin ($H_4$—CPt) share the same metabolic precursor as of $H_4$—BPt, it was reasoned one of them or intermediates were activated as the electron donor of PheH. To test this idea, their respective biosynthesis genes, queD and nudB, were deleted from the HL1308 ΔtyrR strain (HL1310). The ΔqueD strain (HL1312) exhibited no obvious growth defect upon transformation of pTHBscEv and pPheH (Table 2). On the other hand, the ΔnudB strain (HL1314) exhibited severely impaired PheH-dependent growth while restoration of the tyrosine auxotrophy in HL1314 led to a strain (HL1314R) whose growth rate was comparable to control (Table 2).

Physiological characterizations indicated folic acids and their intermediates must have contributed to the turnover of PheH in the evolved strains. The 6-hydroxymethyl-dihydropterin (6-$CH_2OH$—$H_2Pt$) is a metabolic intermediate of folic acids biosynthesis. Enzymatic characterizations have shown FolM reduces 6-$CH_2OH$—$H_2Pt$ to 6-hydroxymethyl-tetrahydropterin (6-$CH_2OH$—$H_4Pt$) in vitro (Pribat et al, 2010) (FIG. 1). Due to its structural resemblance to $H_4$—BPt (FIG. 1 insert), a ΔfolM strain was made but growth measurements showed mutant behaved similar to HL1310 eliminating 6-$CH_2OH$—$H_4Pt$ as a functional complement (Table 2). This result was supported by the making of HL1330, a ΔpabA strain that is capable to synthesize all intermediates of the folic acids biosynthesis pathway from dihydroneopterin triphosphate ($H_2$—$NPtP_3$) to dihydropteroate ($H_2$—Pte) except folic acids (FIG. 1). Growth results showed folates supplementation could rescue JW3323 (BW25113 ΔpabA) (Baba et al, 2006) in M9 but not PheH-dependent growth of HL1330. These results have led us to conclude the tetrahydrofolic acids were the acting donor of PheH in the evolved strain.

TABLE 2

Growth measurements of various mutants [T]

| Strains | Genotype | growth rate, $h^{-1}$ | inoculation $OD_{600}$ | $OD_{600}$ after 8 h | comments |
|---|---|---|---|---|---|
| HL1305 | BW25113 ΔfolX ΔrecA ΔgalE | 0.59 | 0.035 | 0.593 | control strain |
| HL1308[1] | BW25113 ΔfolX ΔtyrA ΔrecA ΔgalE | 0.244 | 0.025 | 0.178 | |

TABLE 2-continued

Growth measurements of various mutants [T]

| Strains | Genotype | growth rate, h$^{-1}$ | inoculation OD$_{600}$ | OD$_{600}$ after 8 h | comments |
|---|---|---|---|---|---|
| HL1310[1] | HL1308 ΔtyrR | 0.33 | 0.023 | 0.382 | |
| HL1312[1] | HL1310 ΔqueD | 0.27 | 0.024 | 0.155 | |
| HL1314[1] | HL1310 ΔnudB | no growth | 0.02 | 0.051 | |
| HL1314R | HL1314 tyrA+ | 0.58 | 0.02 | 0.6 | |
| HL1326[1] | HL1310 ΔfolM | 0.3 | 0.027 | 0.289 | |
| JW3323[LI] | BW25113 ΔpabA | 0.4 | 0.036 | 0.488 | Keio collection |
| HL1330[1, LI] | HL1310 ΔpabA | no growth | 0.022 | 0.035 | |
| THB402F3C9 | HL1308 ΔrpsA[2] rpoB:E546K rpoC:I1357S | 0.58 | 0.027 | 0.61 | evolved strain |

[T] Growth measurements were performed in M9 minimum media with 50 mg/l phenylalanine.
[LI] Folic acids at 10 mg/l were added.
[1] Cells were transformed with pTHBscEv and pPheH.
[2] The rpsA gene is inactivated by a frameshift deletion at the 9th nucleotide after the ATG start codon.

Tryptophan-Hydroxylase Dependent Laboratory Evolution

Based on the phenylalanine-hydroxylase study, we hypothesized that it was possible to use native *E. coli* compounds (e.g. folate species) to support AAH activity with functional expression of the pcd gene being the only requirement. Since it was known that TpH is capable of phenylalanine turnover to form tyrosine in vitro, thus it is plausible to adjust TpH by evolution using the same principle.

In the subsequent evolution, TpH replaced the PheH in the previous evolution. This was done by inserting a Ptrc (Trc promoter)-regulated human TpH gene (encoding SEQ ID NO: 13) onto pTHBscEv along with a counter-selectable sacB gene. The resulting plasmid, pHM1, was introduced to a tyrosine auxotroph HM30 strain, which was derived from JW2581 of the KEIO collection but with the kanamycine-resistant marker at the tyrA locus removed. The final transformed strain was referred as HM35. The HM35 cells were then growth-adapted for high growth rate in the presence of phenylalanine.

At the end of experiment, 94 isolates were picked and were grown in M9 medium supplemented with 200 mg/l of tryptophan and 76 mg/l of tyrosine. The amount of 5HTP formed in the exo-metabolom was measured, it was observed some isolates were able to accumulate more than 10 mg/l of 5HTP and this was ~10-fold more than their parent strain (HM35).

A total of 7 high 5HTP-producers were subjected to total DNA sequence analysis. Three mutations were found common in all strains: FolE (T198I), YnbB (V197A) and TpH (E2K, in SEQ ID NO:13). Both FolE (T198I) and YnbB (V197A) mutations were genomic changes while the TpH (E2K) mutation occurred on the pHM plasmid. Further analyses indicated that the YnbB (V197A) mutation might not be any functional importance since it was also found in the parent HM35 strain. However, without being limited to theory, the T198I change in FolE may have resulted in increased supply of a TpH cofactor as FolE encoding for GTP cyclohydrolase I is the first enzyme leading to tetra-hydrofolates, tetrahydromonapterin and others which may act as TpH cofactors in *E. coli*. This is a particularly interesting result, since preliminary studies have indicated that the catalytic effectiveness of FolE cannot be easily increased by gene overexpression. Furthermore, a proteomic study revealed that the E2K mutation resulted in ~20 fold increase in TpH abundance in contrast to the wild-type form.

Example 2

Directed TpH Engineering

It was found that *Homo sapiens* TpH2, i.e., the fragment set forth as SEQ ID NO:13; hsTpH2, was sensitive to p-chlorophenylalanine. However, mutations at residues N97 and/or P99 were found to confer resistance to p-chlorophenylalanine and to exhibit improved 5HTP biosynthesis after growing cells in the presence of 100 mg/l of tryptophan overnight at 37° C. A further, saturated mutagenesis, study found that isoleucine (I) was a beneficial amino acid change at residue N97, while cysteine (C), aspartic acid (D), leucine (L) and glutamine (Q) were shown to be beneficial at residue P99. In particular, the combined changes N97I/P99D in hsTpH2 showed a >15% increase in 5HTP production in the presence of 100 mg/l tryptophan and the combined changes N97I/P99C in hsTpH2 showed a >25% increase in 5HTP biosynthesis, over the parent TPH2 sequence (SEQ ID NO:13) after acquiring the E2K mutation.

Example 3

Effectiveness of Newly Evolved TpH Background Strain Using *Schistosoma mansoni* TpH One of the 7 evolved high 5HTP-producers was selected to further evaluate if the mutations identified were only specifically beneficial to hsTpH2 or could be widely applicable to others. The chosen evolved strain was first cured to lose the evolution plasmid (e.g. the hsTpH gene) and this was immediately followed by re-introducing the *E. coli* tyrA gene. Upon restoration of the strain's tyrosine auxotrophy, the resulting strain was transformed with pHM2, which is identical to pHM used in the earlier evolution study except that the hsTpH gene was replaced with a *Schistosoma mansoni* TpH gene (SEQ ID NO:9). The 5HTP production of the resulting strain was compared to a wild-type strain carrying pHM2 in the presence of 100 mg/l tryptophan. Results showed the wild-type transformants could only produce ~0.05 mg/l 5HTP while the newly evolved background strain transformants accumulated >20 mg/l. These production results demonstrated that the mutations acquired in the evolved background strain were not only beneficial to hsTpH but also to other TpHs; possibly applicable also to other aromatic amino acid hydroxylases (e.g. tyrosine hydroxylase).

Example 4

Effect of FolE Mutation

This Example shows that the FolE(T198I) mutation is a beneficial mutation towards TpH functionality.

It was assumed the FolE mutation was the main contributor on improving TpH turnover. To challenge this assumption, the FolE(T198I) mutation was introduced into the wild-type BW25113 strain by site-directed mutagenesis using CRISPR. All strains were transformed with a plasmid carrying the human TPH and C. violaceum PCD genes. The transformed cells were grown in M9 medium containing 100 mg/l tryptophan overnight and extracellular metabolites were subjected to analytical measurements. The results are summarized in Table 3.

TABLE 3

Importance of FolE(T198I) on in vivo hsTpH[1] turnover in the presence of 100 mg/l of tryptophan

| Genotype | 5HTP (mg/l) | Indole (mg/l) | 5-hydroxyindole (mg/l) |
| --- | --- | --- | --- |
| wild-type | n.d. | 85 ± 5 | n.d. |
| ΔTnaA | 40 ± 2 | n.d. | n.d. |
| FolE(T198I) | n.d. | n.d. | n.d. |
| ΔTnaA FolE(T198I) | 129 ± 30 | n.d. | n.d. |

[1]hsTpH carries E2K, N97I and P99C mutations in SEQ ID NO: 13
n.d.: not detected As shown in Table 3, wild-type hsTpH expressing cells did not produce 5HTP under tryptophan feeding conditions. However, 5HTP production could be observed with TnaA deletion, which prevented tryptophan and 5HTP degradation. Further 3-folder enhancement on 5HTP production was achieved with FolE(T198I) on ΔTnaA background. Accordingly, the FolE change is a beneficial mutation towards TpH functionality.

Example 5

Tyrosine Hydroxylase Activity

This Example shows that the FolE(T198I) mutation is a beneficial mutation also for supporting tyrosine hydroxylase functionality.

Since both tyrosine hydroxylase and tryptophan hydroxylase belong to the same class of enzyme (i.e., utilizing the same cofactor for oxidation), it was also expected FolE (T198I) would benefit tyrosine hydroxylase activity in terms of converting L-tyrosine to L-3,4-dihydroxyphenylalanine (L-DOPA). Both wild type E. coli and FolE(198I) cells were transformed with a plasmid carrying either the wild-type or truncated rat TH gene expressed from a trc promoter. Additionally, the proline residue of the $2^{nd}$ amino acid of the truncated gene was replaced with lysine. The transformed cells were grew in M9 containing 100 mg/l tyrosine overnight and extracellular metabolites were subjected to analytical measurements. As summarized in Table 4, it was shown that the presence of FolE mutation enhanced L-DOPA formation by about 3-fold when compared to the ones lacking the mutation. Furthermore, it was also shown that removal of the N-terminal mammalian signalling amino acids and substituting the $2^{nd}$ amino acid from proline to lysine additionally enhanced L-DOPA formation about 4-fold. It was therefore a total of c.a. 10-fold improvement achieved by combining all the modifications. Without being limited to theory, it is believed that the FolE mutation could benefit other enzymes of the same class, including phenylalanine hydroxylase (EC 1.14.16.1), phenylalanine 3-hydroxylase (EC 1.14.16.7), tyrosine 3-hydroxylase (EC 1.14.16.2), anthranilate 3-monooxygenase (EC 1.14.16.3), mandelate 4-monooxygenase (EC 1.14.16.6) and Alkylglycerol monooxygenase (EC 1.14.16.5).

TABLE 4

Importance of FolE(T198I) on in vivo tyrosine hydroxylase turnover in the presence of 100 mg/l of tyrosine

| Tyrosine hydroxylase[1] | FolE(T198I) | L-3,4-dihydroxyphenylalanine (LDOPA) (mg/g dry cell weight) |
| --- | --- | --- |
| wild-type[2] | No | 2.88 ± 0.1 |
| wild-type[2] | Yes | 7.25 ± 0.69 |
| P2K Δ(3-157) | No | 10.62 ± 0.71 |
| P2K Δ(3-157) | Yes | 30.3 ± 1.43 |

[1]tyrosine hydroxylase from Rattus norvegicus
[2]NCBI accession number: NP_036872.1

Example 6

Comparing FolE Overexpression with FolE Mutation

This Example shows that overexpression of the wild-type folE gene did not achieve an FolE(T198I) effect.

Gene overexpression has often been used to enhance in vivo enzymatic turnover. As determined in Example 1, TPH-dependent cell growth basing on phenylalanine to tyrosine conversion was an effective way to reflect TPH turnover and its associated networked genes, including its cofactor supply. Therefore, a TPH-dependent growth experiment was set up to compare the effectiveness of the FolE mutation and gene overexpression. Overexpression of the folE gene was achieved by introducing a folE bearing plasmid with its native E. coli promoter intact. The TPH-dependent HM30 cells were transformed with two plasmids: a TPH/PCD bearing plasmid and the concerning folE bearing plasmid. The transformed strains were grown in M9 in the presence of 100 mg/l phenylalanine at 37° C. along with control strains carrying either wild-type chromosomal FolE or FolE(T198I) in additional to TPH/PCD expression from a plasmid. Cell growth was measured at regular intervals.

The results are summarized in FIG. 2. As shown, strains carrying a chromosomal FolE mutation (gFolE*) exhibited rapid TPH-dependent growth during the time course of this experiment. This was in contrast to the native chromosomal variant (gFolE), which barely grew. Although it was interesting to see cells with overexpression of wild-type FolE (gFolE+pFolE) exhibited elevated cell growth yet its growth was not as rapid as the single copy chromosomal mutant. Furthermore, it was observed that cells carrying a hybrid of native and mutated FolE genes (gFolE+pFolE*) showed improved growth; however, its growth was not as good as homogeneous chromosomal mutant (gFolE*). The reason was believed to be that since the T198 residue was located in a peptide segment affecting FolE oligomerization, a hybrid pool of the FolE proteins would ultimately affect the polymerization of the FolE complex and hence its overall activity.

Example 7

Screen of FolE Library

This Example shows that the conformation of the FolE oligomerization helix (Ser207-Arg219) affects GTP cyclohydrolase I activity.

Structural analysis showed that the T198 residue is located in the 4$^{th}$ β-strand that goes in a close proximity to a α-helix defined by Ser207 to Asn222, which can be involved in oligomerization of the FolE complex. Accordingly, T198 may play a role in the FolE oligomerization. Specifically, its mutation would affect the hydrophobic interaction with Leu215 and subsequently the positioning of Ser207-Arg219 helix and overall polymerization of the FolE complex. It can therefore be predicted that additional beneficial FolE mutations can be located in the segments corresponding to residues D97-E112, residues K121-D130, residues N170-H180, residues S193-L200 and residues S207-N222.

A folE gene random library was constructed and was screened by growth according to Example 6. None-redundant growth-improved mutants and their corresponding mutations are summarized in Table 5.

TABLE 5

Summary of beneficial FolE mutations identified by random mutagenesis

| Mutants | FolE mutations | Mutant growth rate, h$^{-1}$ | Improvement over wt |
|---|---|---|---|
| HMP1058[1] | Wild type | 0.19 | (1) |
| HMP1059[2] | T198I | 0.25 | 1.32 |
| P1-01 | I67V, T117I, A125D, H221R | 0.32 | 1.68 |
| P1-02 | V179A | 0.32 | 1.68 |
| P1-03 | M99I | 0.36 | 1.89 |
| P1-04 | E62K, N170K, L215P | 0.41 | 2.16 |
| P1-05 | V102M, L215P | 0.35 | 1.84 |
| P1-06 | T198S | 0.32 | 1.68 |
| P1-07 | Q157L, H212R | 0.36 | 1.89 |
| P1-08 | V28L, L215P, N222I | 0.4 | 2.11 |
| P1-10 | F214S | 0.32 | 1.68 |
| P1-11 | T108N, I133F, E213K | 0.35 | 1.84 |
| P1-12 | Q157L, H212R | 0.37 | 1.95 |
| P2-01 | S5C, D57V, L215Q | 0.36 | 1.89 |
| P2-02 | H29Y, I75V, V179M | 0.32 | 1.68 |
| P2-03 | A14V, E46D, M61I, D97V | 0.36 | 1.89 |
| P2-04 | V28A, G42D, E213K | 0.4 | 2.11 |
| P2-05 | N52K, A68S, S207R | 0.36 | 1.89 |
| P2-06 | L200P | 0.36 | 1.89 |
| P2-07 | A41G, K129N, I133F | 0.3 | 1.58 |
| P2-09 | S3L, K184R, S199Y | 0.32 | 1.68 |
| P2-11 | H12R, N170D, G187S | 0.39 | 2.05 |

[1]In Example 6 illustrated as a mutant of gFolE + pFolE
[2]In Example 6 illustrated as a mutant of gFolE + pFolE*
.: cell growth was measured in M9 with 100 mg/l of phenylalanine at 37° C. overnight.

As shown in Table 5, mutants carrying E213K and L215P or L215Q showed the most significant growth improvement following by D97V and M99I of the D97-E112 segment, N170K and N170D of the N170-H180 segment, and L200P, S207R and H212R of the S207-N222 segment.

Other mutations included V102M of the D97-E112 segment, A125D and K129N of the K121-D130 segment, V179A and V179M of the N170-H180 segment, T198S and S199Y of S193-L200 segment, and F214S, H221R of the S207-N222 segment. Overall, these results strongly suggest that mutations altering FolE oligomerization can significantly alter the overall turnover rate of GTP cyclohydrolase I (FolE).

LIST OF REFERENCES

Lin et al., ACS synthetic biology 2014; 3:497-505
Ehrenworth et al., ACS Synth Biol. 2015 Dec. 18; 4(12): 1295-307.
Yamamoto et al., Metab Eng 2003; 5:246-25
Hara and Kino, AMB Express 2013; 3:70
McKenzie G and Nancy LC (2006) BMC Microbiol 6:39
Nar et al., PNAS USA 1995; 92:12120-5
Rebelo et al., J. Mol. Biol. 2003; 326:503-516
Pribat et al., J Bacteriol 2010a; 192(2):475-82
Pribat et al., Plant Cell 2010b; 22(10):3410-22
Baba et al., Mol Syst Biol 2006:2: 1-11
Cobbett et al., Mol Microbiol 1988; 2: 377-383
Datsenko and Wanner Proc Natl Acad Sci USA 2000; 97: 6640-6645
Pribat et al., J Bacteriol 2010:192: 475-482
Satoh et al., Metabolic engineering 2012; 14:603-610
Tchufistova et al., Nucleic Acids Res 2003:31: 6996-7002
WO 2013/127914 A1, WO 2013/127915 A1 and WO 2015/032911 A1 (Danmarks Tekniske Universitet)
US 2014/134689 AA (University of California)
U.S. Pat. No. 7,807,421 (Asubio Pharma Co., Ltd)

The invention claimed is:

1. A variant of *E. coli* GTP cyclohydrolase I (GCH1) having at least 94% sequence identity to native *E. coli* GCH1 having the sequence of SEQ ID NO:16 and comprising one or more mutations, wherein, in an *E. coli* cell comprising a pterin-4α-carbinolamine dehydratase (PCD) and at least one of a tryptophan hydroxylase (TPH), a tyrosine hydroxylase (TH) and a phenylalanine hydroxylase (PheH), the variant provides for an increased hydroxylation activity of at least one of the TPH, TH and PheH as compared to native *E. coli* GCH1, wherein at least one of the one or more mutations is in an amino acid residue selected from the group consisting of D97, M99, T101, V102, A125, K129, N170, V179, T196, T198, S199, L200, S207, H212, E213, F214, L215 and H221, and wherein the mutation in N170 is N170K, N170D or N170L; the mutation in T198 is T198I, T198V or T198L; the mutation in V179 is V179A; the mutation in H212 is H212R or H212K; and the mutation in H221 is H221R or H221K.

2. The variant of claim 1, wherein the variant comprises a mutation selected from D97V, D97L, D97A, D97T, M99C, M99T, M99V, M99L, M99I, T101I, T101V, T101L, V102M, N170K, N170D, N170L, V179A, T196I, T196V, T196L, T198I, T198V, T198L, S199Y, S199F, L200P, L200C, L200S, L200A, S207R, S207K, S207M, H212R, H212K, E213K, E213R, F214A, F214G, F214S, L215P, L215Q, L215N, L215D, L215T, L215S, L215G, L215A, L215C, L215F, L215M, H221R and H221K, or a combination thereof.

3. The variant of claim 1, comprising a mutation selected from T198I, F214S, V179A, M99I, L200P and L215P.

4. A nucleic acid sequence encoding the variant of *E. coli* GCH1 of claim 1.

5. A recombinant microbial cell comprising the variant of claim 1.

6. The recombinant microbial cell of claim 5, further comprising nucleic acid sequences encoding a PCD and a monooxygenase.

7. The recombinant microbial cell of claim 6, wherein
   (a) The recombinant microbial cell of claim 6, wherein
      (a) the PCD is derived from *Chromobacterium violecum, Homo sapiens, Pseudomonas aeruginosa* and *Rattus norvegicus*; or a functionally active variant thereof;
      (b) the monooxygenase is a TPH derived from a *Schistosoma mansoni, Homo sapiens, Gallus gallus, Bos taurus, Sus scrofa, Equus caballus, Mus musculus* and *Oryctolagus cuniculus* TPH; or a functionally active variant thereof;
      (c) the monooxygenase is a TH derived from *Rattus norwegicus, Homo sapiens, Mus musculus, Bos taurus, Gallus gallus* or a functionally active variant thereof;
      (d) the monooxygenase is a PheH derived from *Chromobacterium violaceum, Xanthomonas campestris* pv. *Viticola, Pseudomonas aeruginosa, Pseudomonas putida, Homo sapiens, Mus musculus, Streptomyces coeruleorubidus* or a functionally active variant thereof; or
      (e) a combination of (a) and (b), (a) and (c) or (a) and (d).

8. The recombinant microbial cell of claim 6, wherein each nucleic acid sequence is operably linked to an inducible, a regulated or a constitutive promoter, and/or wherein at least the nucleic acid sequence encoding the variant of *E. coli* GCH1 is chromosomally integrated.

9. The recombinant microbial cell of claim 6, which is derived from a bacterial cell, a yeast cell, a filamentous fungal cell, or an algal cell.

10. The recombinant microbial cell of claim 9, which is derived from an *Escherichia*, a *Saccharomyces*, a *Schizosaccharomyces*, a *Corynebacterium*, a *Bacillus* or a *Streptomyces* cell.

11. The recombinant microbial cell of claim 6, further comprising
    (a) a nucleic acid sequence encoding a 5HTP decarboxylase (ADDC);
    (b) nucleic acid sequences encoding an ADDC and a serotonin acetyltransferase (AANAT);
    (c) nucleic acid sequences encoding an ADDC, an AANAT, and an acetylserotonin O-methyltransferase (ASMT); or
    (d) nucleic acid sequences encoding a dopa decarboxylase, a tyramine oxidase and an alcohol dehydrogenase.

12. A method of producing one or more oxidation products of an aromatic amino acid, comprising culturing the recombinant microbial cell of claim 6 in a medium comprising a carbon source, and, optionally, isolating the oxidation product.

13. The method of claim 12, wherein the oxidation product comprises at least one of 5HTP, L-DOPA, tyrosine, m-tyrosine, hydroxytyrosol, serotonin and melatonin.

14. A variant of claim 1, *E. coli* GTP cyclohydrolase I (GCH1) having at least 94% sequence identity to native *E. coli* GCH1 having the sequence of SEQ ID NO:16 and comprising an amino acid substitution selected from T198I, V179A, M99I, F214S and L200P, or a combination of amino acid substitutions selected from (a) to (n):
    (a) I67V, T117I, A125D, H221R;
    (b) E62K, N170K, L215P;
    (c) V102M, L215P;
    (d) Q157L, H212R;
    (e) V28L, L215P, N222I;
    (f) T108N, I133F, E213K;
    (g) S5C, D57V, L215Q;
    (h) H29Y, I75V, V179M;
    (i) A14V, E46D, M61I, D97V;
    (j) V28A, G42D, E213K;
    (k) N52K, A68S, S207R;
    (l) A41G, K129N, I133F;
    (m) S3L, K184R, S199Y; and
    (n) H12R, N170D, G187S.

15. A variant of *E. coli* GTP cyclohydrolase I (GCH1) having at least 98% sequence identity to native *E. coli* GCH1 having the sequence of SEQ ID NO:16,
    wherein the variant comprises a mutation in amino acid residue T198, and
    wherein, in an *E. coli* cell comprising a PCD and at least one of a TPH, a TH and a PheH, the variant provides for an increased hydroxylation activity of at least one of the TPH, TH and PheH as compared to native *E. coli* GCH1.

16. The variant of claim 15, wherein the mutation is selected from T198I, T198S, T198V and T198L.

17. The variant of claim 1, wherein the variant has at least about 98% sequence identity to native *E. coli* GCH1 having the sequence of SEQ ID NO:16.

18. The variant of claim 1, wherein the variant provides for a hydroxylation activity of at least about 120% as compared to native *E. coli* GCH1 having the sequence of SEQ ID NO:16.

19. The variant of claim 2, wherein the variant has at least about 98% sequence identity to native *E. coli* GCH1 having the sequence of SEQ ID NO:16.

20. A variant of *E. coli* GCH1 consisting of SEQ ID NO:16 except for a T198I mutation.

21. The recombinant microbial cell of claim 10, wherein said *Escherichia* cell is an *E. coli* cell.

\* \* \* \* \*

```
SEQUENCE LISTING

<160> NUMBER OF SEQ ID NOS: 64

<210> SEQ ID NO 1
<211> LENGTH: 444
<212> TYPE: PRT
<213> ORGANISM: Oryctolagus cuniculus

<400> SEQUENCE: 1

Met Ile Glu Asp Asn Lys Glu Asn Lys Asp His Ser Leu Glu Arg Gly
1               5                   10                  15

Arg Ala Thr Leu Ile Phe Ser Leu Lys Asn Glu Val Gly Gly Leu Ile
            20                  25                  30

Lys Ala Leu Lys Ile Phe Gln Glu Lys His Val Asn Leu Leu His Ile
```

```
                35                  40                  45
Glu Ser Arg Lys Ser Lys Arg Arg Asn Ser Glu Phe Glu Ile Phe Val
 50                  55                  60

Asp Cys Asp Thr Asn Arg Glu Gln Leu Asn Asp Ile Phe His Leu Leu
 65                  70                  75                  80

Lys Ser His Thr Asn Val Leu Ser Val Thr Pro Pro Asp Asn Phe Thr
                 85                  90                  95

Met Lys Glu Glu Gly Met Glu Ser Val Pro Trp Phe Pro Lys Lys Ile
            100                 105                 110

Ser Asp Leu Asp His Cys Ala Asn Arg Val Leu Met Tyr Gly Ser Glu
            115                 120                 125

Leu Asp Ala Asp His Pro Gly Phe Lys Asp Asn Val Tyr Arg Lys Arg
            130                 135                 140

Arg Lys Tyr Phe Ala Asp Leu Ala Met Ser Tyr Lys Tyr Gly Asp Pro
145                 150                 155                 160

Ile Pro Lys Val Glu Phe Thr Glu Glu Ile Lys Thr Trp Gly Thr
                165                 170                 175

Val Phe Arg Glu Leu Asn Lys Leu Tyr Pro Thr His Ala Cys Arg Glu
            180                 185                 190

Tyr Leu Lys Asn Leu Pro Leu Leu Ser Lys Tyr Cys Gly Tyr Arg Glu
            195                 200                 205

Asp Asn Ile Pro Gln Leu Glu Asp Ile Ser Asn Phe Leu Lys Glu Arg
210                 215                 220

Thr Gly Phe Ser Ile Arg Pro Val Ala Gly Tyr Leu Ser Pro Arg Asp
225                 230                 235                 240

Phe Leu Ser Gly Leu Ala Phe Arg Val Phe His Cys Thr Gln Tyr Val
                245                 250                 255

Arg His Ser Ser Asp Pro Phe Tyr Thr Pro Glu Pro Asp Thr Cys His
            260                 265                 270

Glu Leu Leu Gly His Val Pro Leu Leu Ala Glu Pro Ser Phe Ala Gln
            275                 280                 285

Phe Ser Gln Glu Ile Gly Leu Ala Ser Leu Gly Ala Ser Glu Glu Ala
            290                 295                 300

Val Gln Lys Leu Ala Thr Cys Tyr Phe Phe Thr Val Glu Phe Gly Leu
305                 310                 315                 320

Cys Lys Gln Asp Gly Gln Leu Arg Val Phe Gly Ala Gly Leu Leu Ser
                325                 330                 335

Ser Ile Ser Glu Leu Lys His Val Leu Ser Gly His Ala Lys Val Lys
            340                 345                 350

Pro Phe Asp Pro Lys Ile Thr Tyr Lys Gln Glu Cys Leu Ile Thr Thr
            355                 360                 365

Phe Gln Asp Val Tyr Phe Val Ser Glu Ser Phe Glu Asp Ala Lys Glu
            370                 375                 380

Lys Met Arg Glu Phe Thr Lys Thr Ile Lys Arg Pro Phe Gly Val Lys
385                 390                 395                 400

Tyr Asn Pro Tyr Thr Arg Ser Ile Gln Ile Leu Lys Asp Ala Lys Ser
                405                 410                 415

Ile Thr Asn Ala Met Asn Glu Leu Arg His Asp Leu Ala Val Val Ser
            420                 425                 430

Asp Ala Leu Gly Lys Val Ser Arg Gln Leu Ser Val
            435                 440

<210> SEQ ID NO 2
```

```
<211> LENGTH: 444
<212> TYPE: PRT
<213> ORGANISM: Homo sapiens

<400> SEQUENCE: 2

Met Ile Glu Asp Asn Lys Glu Asn Lys Asp His Ser Leu Glu Arg Gly
1               5                   10                  15

Arg Ala Ser Leu Ile Phe Ser Leu Lys Asn Glu Val Gly Gly Leu Ile
            20                  25                  30

Lys Ala Leu Lys Ile Phe Gln Glu Lys His Val Asn Leu Leu His Ile
        35                  40                  45

Glu Ser Arg Lys Ser Lys Arg Arg Asn Ser Glu Phe Glu Ile Phe Val
    50                  55                  60

Asp Cys Asp Ile Asn Arg Glu Gln Leu Asn Asp Ile Phe His Leu Leu
65                  70                  75                  80

Lys Ser His Thr Asn Val Leu Ser Val Asn Leu Pro Asp Asn Phe Thr
                85                  90                  95

Leu Lys Glu Asp Gly Met Glu Thr Val Pro Trp Phe Pro Lys Lys Ile
            100                 105                 110

Ser Asp Leu Asp His Cys Ala Asn Arg Val Leu Met Tyr Gly Ser Glu
        115                 120                 125

Leu Asp Ala Asp His Pro Gly Phe Lys Asp Asn Val Tyr Arg Lys Arg
    130                 135                 140

Arg Lys Tyr Phe Ala Asp Leu Ala Met Asn Tyr Lys His Gly Asp Pro
145                 150                 155                 160

Ile Pro Lys Val Glu Phe Thr Glu Glu Ile Lys Thr Trp Gly Thr
                165                 170                 175

Val Phe Gln Glu Leu Asn Lys Leu Tyr Pro Thr His Ala Cys Arg Glu
            180                 185                 190

Tyr Leu Lys Asn Leu Pro Leu Leu Ser Lys Tyr Cys Gly Tyr Arg Glu
        195                 200                 205

Asp Asn Ile Pro Gln Leu Glu Asp Val Ser Asn Phe Leu Lys Glu Arg
    210                 215                 220

Thr Gly Phe Ser Ile Arg Pro Val Ala Gly Tyr Leu Ser Pro Arg Asp
225                 230                 235                 240

Phe Leu Ser Gly Leu Ala Phe Arg Val Phe His Cys Thr Gln Tyr Val
                245                 250                 255

Arg His Ser Ser Asp Pro Phe Tyr Thr Pro Glu Pro Asp Thr Cys His
            260                 265                 270

Glu Leu Leu Gly His Val Pro Leu Leu Ala Glu Pro Ser Phe Ala Gln
        275                 280                 285

Phe Ser Gln Glu Ile Gly Leu Ala Ser Leu Gly Ala Ser Glu Glu Ala
    290                 295                 300

Val Gln Lys Leu Ala Thr Cys Tyr Phe Phe Thr Val Glu Phe Gly Leu
305                 310                 315                 320

Cys Lys Gln Asp Gly Gln Leu Arg Val Phe Gly Ala Gly Leu Leu Ser
                325                 330                 335

Ser Ile Ser Glu Leu Lys His Ala Leu Ser Gly His Ala Lys Val Lys
            340                 345                 350

Pro Phe Asp Pro Lys Ile Thr Cys Lys Gln Glu Cys Leu Ile Thr Thr
        355                 360                 365

Phe Gln Asp Val Tyr Phe Val Ser Glu Ser Phe Glu Asp Ala Lys Glu
    370                 375                 380

Lys Met Arg Glu Phe Thr Lys Thr Ile Lys Arg Pro Phe Gly Val Lys
```

```
                385                 390                 395                 400

Tyr Asn Pro Tyr Thr Arg Ser Ile Gln Ile Leu Lys Asp Thr Lys Ser
                    405                 410                 415

Ile Thr Ser Ala Met Asn Glu Leu Gln His Asp Leu Asp Val Val Ser
                420                 425                 430

Asp Ala Leu Ala Lys Val Ser Arg Lys Pro Ser Ile
                435                 440

<210> SEQ ID NO 3
<211> LENGTH: 490
<212> TYPE: PRT
<213> ORGANISM: Homo sapiens

<400> SEQUENCE: 3

Met Gln Pro Ala Met Met Phe Ser Ser Lys Tyr Trp Ala Arg Arg
1               5                   10                  15

Gly Phe Ser Leu Asp Ser Ala Val Pro Glu Glu His Gln Leu Leu Gly
                20                  25                  30

Ser Ser Thr Leu Asn Lys Pro Asn Ser Gly Lys Asn Asp Asp Lys Gly
            35                  40                  45

Asn Lys Gly Ser Ser Lys Arg Glu Ala Ala Thr Glu Ser Gly Lys Thr
50                  55                  60

Ala Val Val Phe Ser Leu Lys Asn Glu Val Gly Gly Leu Val Lys Ala
65                  70                  75                  80

Leu Arg Leu Phe Gln Glu Lys Arg Val Asn Met Val His Ile Glu Ser
                85                  90                  95

Arg Lys Ser Arg Arg Arg Ser Ser Glu Val Glu Ile Phe Val Asp Cys
                100                 105                 110

Glu Cys Gly Lys Thr Glu Phe Asn Glu Leu Ile Gln Leu Leu Lys Phe
            115                 120                 125

Gln Thr Thr Ile Val Thr Leu Asn Pro Pro Glu Asn Ile Trp Thr Glu
130                 135                 140

Glu Glu Glu Leu Glu Asp Val Pro Trp Phe Pro Arg Lys Ile Ser Glu
145                 150                 155                 160

Leu Asp Lys Cys Ser His Arg Val Leu Met Tyr Gly Ser Glu Leu Asp
                165                 170                 175

Ala Asp His Pro Gly Phe Lys Asp Asn Val Tyr Arg Gln Arg Arg Lys
            180                 185                 190

Tyr Phe Val Asp Val Ala Met Gly Tyr Lys Tyr Gly Gln Pro Ile Pro
                195                 200                 205

Arg Val Glu Tyr Thr Glu Glu Glu Thr Lys Thr Trp Gly Val Val Phe
210                 215                 220

Arg Glu Leu Ser Lys Leu Tyr Pro Thr His Ala Cys Arg Glu Tyr Leu
225                 230                 235                 240

Lys Asn Phe Pro Leu Leu Thr Lys Tyr Cys Gly Tyr Arg Glu Asp Asn
                245                 250                 255

Val Pro Gln Leu Glu Asp Val Ser Met Phe Leu Lys Glu Arg Ser Gly
            260                 265                 270

Phe Thr Val Arg Pro Val Ala Gly Tyr Leu Ser Pro Arg Asp Phe Leu
                275                 280                 285

Ala Gly Leu Ala Tyr Arg Val Phe His Cys Thr Gln Tyr Ile Arg His
            290                 295                 300

Gly Ser Asp Pro Leu Tyr Thr Pro Glu Pro Asp Thr Cys His Glu Leu
305                 310                 315                 320
```

```
Leu Gly His Val Pro Leu Leu Ala Asp Pro Lys Phe Ala Gln Phe Ser
            325                 330                 335

Gln Glu Ile Gly Leu Ala Ser Leu Gly Ala Ser Asp Glu Asp Val Gln
        340                 345                 350

Lys Leu Ala Thr Cys Tyr Phe Phe Thr Ile Glu Phe Gly Leu Cys Lys
            355                 360                 365

Gln Glu Gly Gln Leu Arg Ala Tyr Gly Ala Gly Leu Leu Ser Ser Ile
    370                 375                 380

Gly Glu Leu Lys His Ala Leu Ser Asp Lys Ala Cys Val Lys Ala Phe
385                 390                 395                 400

Asp Pro Lys Thr Thr Cys Leu Gln Glu Cys Leu Ile Thr Thr Phe Gln
                405                 410                 415

Glu Ala Tyr Phe Val Ser Glu Ser Phe Glu Glu Ala Lys Glu Lys Met
            420                 425                 430

Arg Asp Phe Ala Lys Ser Ile Thr Arg Pro Phe Ser Val Tyr Phe Asn
        435                 440                 445

Pro Tyr Thr Gln Ser Ile Glu Ile Leu Lys Asp Thr Arg Ser Ile Glu
    450                 455                 460

Asn Val Val Gln Asp Leu Arg Ser Asp Leu Asn Thr Val Cys Asp Ala
465                 470                 475                 480

Leu Asn Lys Met Asn Gln Tyr Leu Gly Ile
                485                 490

<210> SEQ ID NO 4
<211> LENGTH: 502
<212> TYPE: PRT
<213> ORGANISM: Bos taurus

<400> SEQUENCE: 4

Met Gln Pro Ala Met Met Met Phe Ser Ser Lys Tyr Trp Ala Arg Arg
1               5                   10                  15

Gly Leu Ser Leu Asp Ser Ala Val Pro Glu Glu His Gln Leu Leu Thr
            20                  25                  30

Ser Leu Thr Leu Asn Lys Thr Asn Ser Gly Lys Asn Asp Asp Lys Lys
        35                  40                  45

Gly Asn Lys Gly Ser Ser Lys Asn Asp Thr Ala Thr Glu Ser Gly Lys
    50                  55                  60

Thr Ala Val Val Phe Ser Leu Lys Asn Glu Val Gly Gly Leu Val Lys
65                  70                  75                  80

Ala Leu Lys Leu Phe Gln Glu Lys His Val Asn Met Ile His Ile Glu
                85                  90                  95

Ser Arg Lys Ser Arg Arg Arg Ser Ser Glu Val Glu Ile Phe Val Asp
            100                 105                 110

Cys Glu Cys Gly Lys Thr Glu Phe Asn Glu Leu Ile Gln Ser Leu Lys
        115                 120                 125

Phe Gln Thr Thr Ile Val Thr Leu Asn Pro Pro Glu Asn Ile Trp Thr
    130                 135                 140

Glu Glu Glu Gly Lys Leu Thr Cys Val Ala Lys Gly Lys Glu Leu Glu
145                 150                 155                 160

Asp Val Pro Trp Phe Pro Arg Lys Ile Ser Glu Leu Asp Arg Cys Ser
                165                 170                 175

His Arg Val Leu Met Tyr Gly Ser Glu Leu Asp Ala Asp His Pro Gly
            180                 185                 190

Phe Lys Asp Asn Val Tyr Arg Gln Arg Arg Lys Tyr Phe Val Asp Val
        195                 200                 205
```

Ala Met Gly Tyr Lys Tyr Gly Gln Pro Ile Pro Arg Val Glu Tyr Thr
         210                 215                 220

Glu Glu Glu Thr Lys Thr Trp Gly Val Val Phe Arg Glu Leu Ser Lys
225                 230                 235                 240

Leu Tyr Pro Thr His Ala Cys Arg Glu Tyr Leu Lys Asn Phe Pro Leu
             245                 250                 255

Leu Thr Lys His Cys Gly Tyr Arg Glu Asp Asn Val Pro Gln Leu Glu
             260                 265                 270

Asp Val Ala Ala Phe Leu Lys Glu Arg Ser Gly Phe Thr Val Arg Pro
         275                 280                 285

Val Ala Gly Tyr Leu Ser Pro Arg Asp Phe Leu Ala Gly Leu Ala Tyr
         290                 295                 300

Arg Val Phe His Cys Thr Gln Tyr Val Arg His Gly Ser Asp Pro Leu
305                 310                 315                 320

Tyr Thr Pro Glu Pro Asp Val Thr Leu Ser Leu Leu Ser His Val Pro
             325                 330                 335

Leu Ile Phe Asp Asp Gln Phe Pro Thr Ser Phe Ser Asn Glu Val Gly
             340                 345                 350

Arg Ala Val Ile Leu Ala Ser Trp Gly Asp Lys Gln Glu Asn Asn Gln
         355                 360                 365

Cys Tyr Phe Phe Thr Ile Glu Phe Gly Leu Cys Lys Gln Glu Gly Gln
         370                 375                 380

Leu Arg Ala Tyr Gly Ala Gly Leu Leu Ser Ser Ile Gly Glu Leu Lys
385                 390                 395                 400

His Ala Leu Ser Asp Lys Ala Cys Val Lys Ala Phe Asp Pro Lys Thr
             405                 410                 415

Thr Cys Leu Gln Glu Cys Leu Ile Thr Thr Phe Gln Glu Ala Tyr Phe
             420                 425                 430

Val Ser Glu Ser Phe Glu Glu Ala Lys Glu Lys Met Arg Asp Phe Ala
         435                 440                 445

Lys Ser Ile Thr Arg Pro Phe Ser Val Tyr Phe Asn Pro Tyr Thr Gln
         450                 455                 460

Ser Ile Glu Ile Leu Lys Asp Thr Arg Ser Ile Glu Asn Val Val Gln
465                 470                 475                 480

Asp Leu Arg Ser Asp Leu Asn Thr Val Cys Asp Ala Leu Asn Lys Met
             485                 490                 495

Asn Gln Tyr Leu Gly Ile
             500

<210> SEQ ID NO 5
<211> LENGTH: 497
<212> TYPE: PRT
<213> ORGANISM: Sus scrofa

<400> SEQUENCE: 5

Met Gln Pro Ala Met Met Met Phe Ser Ser Lys Tyr Trp Ala Arg Arg
1               5                   10                  15

Gly Leu Ser Leu Asp Ser Ala Val Pro Glu Glu His Gln Leu Leu Gly
            20                  25                  30

Ser Leu Thr Val Ser Thr Phe Leu Lys Leu Asn Lys Ser Asn Ser Gly
        35                  40                  45

Lys Asn Asp Asp Lys Lys Gly Asn Lys Gly Ser Gly Lys Ser Asp Thr
    50                  55                  60

Ala Thr Glu Ser Gly Lys Thr Ala Val Val Phe Ser Leu Lys Asn Glu

-continued

```
            65                  70                  75                  80
        Val Gly Gly Leu Val Lys Ala Leu Lys Leu Phe Gln Glu Lys His Val
                        85                  90                  95

Asn Met Val His Ile Glu Ser Arg Lys Ser Arg Arg Ser Ser Glu
                        100                 105                 110

Val Glu Ile Phe Val Asp Cys Glu Cys Gly Lys Thr Glu Phe Asn Glu
                        115                 120                 125

Leu Ile Gln Ser Leu Lys Phe Gln Thr Thr Ile Val Thr Leu Asn Pro
                        130                 135                 140

Pro Glu Asn Ile Trp Thr Glu Glu Glu Leu Glu Asp Val Pro Trp
        145                 150                 155                 160

Phe Pro Arg Lys Ile Ser Glu Leu Asp Lys Cys Ser His Arg Val Leu
                        165                 170                 175

Met Tyr Gly Ser Glu Leu Asp Ala Asp His Pro Gly Phe Lys Asp Asn
                        180                 185                 190

Val Tyr Arg Gln Arg Arg Lys Tyr Phe Val Asp Leu Ala Met Gly Tyr
                        195                 200                 205

Lys Tyr Gly Gln Pro Ile Pro Arg Val Glu Tyr Thr Glu Glu Thr
        210                 215                 220

Lys Thr Trp Gly Ile Val Phe Arg Glu Leu Ser Lys Leu Tyr Pro Thr
        225                 230                 235                 240

His Ala Cys Arg Glu Tyr Leu Lys Asn Phe Pro Leu Leu Thr Lys Tyr
                        245                 250                 255

Cys Gly Tyr Arg Glu Asp Asn Val Pro Gln Leu Glu Asp Val Ser Val
                        260                 265                 270

Phe Leu Lys Glu Arg Ser Gly Phe Thr Val Arg Pro Val Ala Gly Tyr
                        275                 280                 285

Leu Ser Pro Arg Asp Phe Leu Ala Gly Leu Ala Tyr Arg Val Phe His
                        290                 295                 300

Cys Thr Gln Tyr Val Arg His Gly Ser Asp Pro Leu Tyr Thr Pro Glu
        305                 310                 315                 320

Pro Asp Thr Cys His Glu Leu Leu Gly His Val Pro Leu Leu Ala Asp
                        325                 330                 335

Pro Lys Phe Ala Gln Phe Ser Gln Glu Ile Gly Leu Ala Ser Leu Gly
                        340                 345                 350

Ala Ser Asp Glu Asp Val Gln Lys Leu Ala Thr Cys Tyr Phe Phe Thr
                        355                 360                 365

Ile Glu Phe Gly Leu Cys Lys Gln Glu Gly Gln Leu Arg Ala Tyr Gly
                        370                 375                 380

Ala Gly Leu Leu Ser Ser Ile Gly Glu Leu Lys His Ala Leu Ser Asp
        385                 390                 395                 400

Lys Ala Cys Val Lys Ala Phe Asp Pro Lys Thr Thr Cys Leu Gln Glu
                        405                 410                 415

Cys Leu Ile Thr Thr Phe Gln Glu Ala Tyr Phe Val Ser Glu Ser Phe
                        420                 425                 430

Glu Glu Ala Lys Glu Lys Met Arg Asp Phe Ala Lys Ser Ile Thr Arg
                        435                 440                 445

Pro Phe Ser Val Tyr Phe Asn Pro Tyr Thr Gln Ser Ile Glu Ile Leu
                        450                 455                 460

Lys Asp Thr Arg Ser Ile Glu Asn Val Val Gln Asp Leu Arg Ser Asp
        465                 470                 475                 480

Leu Asn Thr Val Cys Asp Ala Leu Asn Lys Met Asn Gln Tyr Leu Gly
                        485                 490                 495
```

Ile

<210> SEQ ID NO 6
<211> LENGTH: 445
<212> TYPE: PRT
<213> ORGANISM: Gallus gallus

<400> SEQUENCE: 6

```
Met Ile Glu Asp Asn Lys Glu Asn Lys Asp His Ala Pro Arg Gly
1               5                  10                  15

Arg Thr Ala Ile Ile Phe Ser Leu Lys Asn Glu Val Gly Gly Leu Val
            20                  25                  30

Lys Ala Leu Lys Leu Phe Gln Glu Lys His Val Asn Leu Val His Ile
            35                  40                  45

Glu Ser Arg Lys Ser Lys Arg Arg Asn Ser Glu Phe Glu Ile Phe Val
    50                  55                  60

Asp Cys Asp Ser Asn Arg Glu Gln Leu Asn Glu Ile Phe Gln Leu Leu
65                  70                  75                  80

Lys Ser His Val Ser Ile Val Ser Met Asn Pro Thr Glu His Phe Asn
                85                  90                  95

Val Gln Glu Asp Gly Asp Met Glu Asn Ile Pro Trp Tyr Pro Lys Lys
            100                 105                 110

Ile Ser Asp Leu Asp Lys Cys Ala Asn Arg Val Leu Met Tyr Gly Ser
        115                 120                 125

Asp Leu Asp Ala Asp His Pro Gly Phe Lys Asp Asn Val Tyr Arg Lys
    130                 135                 140

Arg Arg Lys Tyr Phe Ala Asp Leu Ala Met Asn Tyr Lys His Gly Asp
145                 150                 155                 160

Pro Ile Pro Glu Ile Glu Phe Thr Glu Glu Ile Lys Thr Trp Gly
                165                 170                 175

Thr Val Tyr Arg Glu Leu Asn Lys Leu Tyr Pro Thr His Ala Cys Arg
            180                 185                 190

Glu Tyr Leu Lys Asn Leu Pro Leu Leu Thr Lys Tyr Cys Gly Tyr Arg
        195                 200                 205

Glu Asp Asn Ile Pro Gln Leu Glu Asp Val Ser Arg Phe Leu Lys Glu
    210                 215                 220

Arg Thr Gly Phe Thr Ile Arg Pro Val Ala Gly Tyr Leu Ser Pro Arg
225                 230                 235                 240

Asp Phe Leu Ala Gly Leu Ala Phe Arg Val Phe His Cys Thr Gln Tyr
                245                 250                 255

Val Arg His Ser Ser Asp Pro Leu Tyr Thr Pro Glu Pro Asp Thr Cys
            260                 265                 270

His Glu Leu Leu Gly His Val Pro Leu Leu Ala Glu Pro Ser Phe Ala
        275                 280                 285

Gln Phe Ser Gln Glu Ile Gly Leu Ala Ser Leu Gly Ala Ser Asp Glu
    290                 295                 300

Ala Val Gln Lys Leu Ala Thr Cys Tyr Phe Phe Thr Val Glu Phe Gly
305                 310                 315                 320

Leu Cys Lys Gln Glu Gly Gln Leu Arg Val Tyr Gly Ala Gly Leu Leu
                325                 330                 335

Ser Ser Ile Ser Glu Leu Lys His Ser Leu Ser Gly Ser Ala Lys Val
            340                 345                 350

Lys Pro Phe Asp Pro Lys Val Thr Cys Lys Gln Glu Cys Leu Ile Thr
        355                 360                 365
```

```
Thr Phe Gln Glu Val Tyr Phe Ser Glu Ser Phe Glu Glu Ala Lys
        370                 375                 380

Glu Lys Met Arg Glu Phe Ala Lys Thr Ile Lys Arg Pro Phe Gly Val
385                 390                 395                 400

Lys Tyr Asn Pro Tyr Thr Gln Ser Val Gln Ile Leu Lys Asp Thr Lys
                405                 410                 415

Ser Ile Ala Ser Val Val Asn Glu Leu Arg His Glu Leu Asp Ile Val
                420                 425                 430

Ser Asp Ala Leu Ser Lys Met Gly Lys Gln Leu Glu Val
                435                 440                 445
```

<210> SEQ ID NO 7
<211> LENGTH: 447
<212> TYPE: PRT
<213> ORGANISM: Mus musculus

<400> SEQUENCE: 7

```
Met Ile Glu Asp Asn Lys Glu Asn Lys Glu Asn Lys Asp His Ser Ser
1               5                   10                  15

Glu Arg Gly Arg Val Thr Leu Ile Phe Ser Leu Glu Asn Glu Val Gly
                20                  25                  30

Gly Leu Ile Lys Val Leu Lys Ile Phe Gln Glu Asn His Val Ser Leu
            35                  40                  45

Leu His Ile Glu Ser Arg Lys Ser Lys Gln Arg Asn Ser Glu Phe Glu
    50                  55                  60

Ile Phe Val Asp Cys Asp Ile Ser Arg Glu Gln Leu Asn Asp Ile Phe
65                  70                  75                  80

Pro Leu Leu Lys Ser His Ala Thr Val Leu Ser Val Asp Ser Pro Asp
                85                  90                  95

Gln Leu Thr Ala Lys Glu Asp Val Met Glu Thr Val Pro Trp Phe Pro
                100                 105                 110

Lys Lys Ile Ser Asp Leu Asp Phe Cys Ala Asn Arg Val Leu Leu Tyr
            115                 120                 125

Gly Ser Glu Leu Asp Ala Asp His Pro Gly Phe Lys Asp Asn Val Tyr
130                 135                 140

Arg Arg Arg Arg Lys Tyr Phe Ala Glu Leu Ala Met Asn Tyr Lys His
145                 150                 155                 160

Gly Asp Pro Ile Pro Lys Ile Glu Phe Thr Glu Glu Ile Lys Thr
                165                 170                 175

Trp Gly Thr Ile Phe Arg Glu Leu Asn Lys Leu Tyr Pro Thr His Ala
                180                 185                 190

Cys Arg Glu Tyr Leu Arg Asn Leu Pro Leu Leu Ser Lys Tyr Cys Gly
            195                 200                 205

Tyr Arg Glu Asp Asn Ile Pro Gln Leu Glu Asp Val Ser Asn Phe Leu
210                 215                 220

Lys Glu Arg Thr Gly Phe Ser Ile Arg Pro Val Ala Gly Tyr Leu Ser
225                 230                 235                 240

Pro Arg Asp Phe Leu Ser Gly Leu Ala Phe Arg Val Phe His Cys Thr
                245                 250                 255

Gln Tyr Val Arg His Ser Ser Asp Pro Leu Tyr Thr Pro Glu Pro Asp
                260                 265                 270

Thr Cys His Glu Leu Leu Gly His Val Pro Leu Leu Ala Glu Pro Ser
            275                 280                 285

Phe Ala Gln Phe Ser Gln Glu Ile Gly Leu Ala Ser Leu Gly Ala Ser
```

```
                    290                 295                 300

Glu Glu Thr Val Gln Lys Leu Ala Thr Cys Tyr Phe Phe Thr Val Glu
305                 310                 315                 320

Phe Gly Leu Cys Lys Gln Asp Gly Gln Leu Arg Val Phe Gly Ala Gly
                    325                 330                 335

Leu Leu Ser Ser Ile Ser Glu Leu Lys His Ala Leu Ser Gly His Ala
                    340                 345                 350

Lys Val Lys Pro Phe Asp Pro Lys Ile Ala Cys Lys Gln Glu Cys Leu
                    355                 360                 365

Ile Thr Ser Phe Gln Asp Val Tyr Phe Val Ser Glu Ser Phe Glu Asp
                    370                 375                 380

Ala Lys Glu Lys Met Arg Glu Phe Ala Lys Thr Val Lys Arg Pro Phe
385                 390                 395                 400

Gly Leu Lys Tyr Asn Pro Tyr Thr Gln Ser Val Gln Val Leu Arg Asp
                    405                 410                 415

Thr Lys Ser Ile Thr Ser Ala Met Asn Glu Leu Arg Tyr Asp Leu Asp
                    420                 425                 430

Val Ile Ser Asp Ala Leu Ala Arg Val Thr Arg Trp Pro Ser Val
                    435                 440                 445

<210> SEQ ID NO 8
<211> LENGTH: 491
<212> TYPE: PRT
<213> ORGANISM: Equus caballus

<400> SEQUENCE: 8

Met Gln Pro Ala Met Met Met Phe Ser Ser Lys Tyr Trp Ala Arg Arg
1               5                   10                  15

Gly Phe Ser Leu Asp Ser Ala Val Pro Glu Glu His Gln Leu Leu Gly
                20                  25                  30

Asn Leu Thr Val Asn Lys Ser Asn Ser Gly Lys Asn Asp Asp Lys Lys
                35                  40                  45

Gly Asn Lys Gly Ser Ser Arg Ser Glu Thr Ala Pro Asp Ser Gly Lys
50                  55                  60

Thr Ala Val Val Phe Ser Leu Arg Asn Glu Val Gly Gly Leu Val Lys
65                  70                  75                  80

Ala Leu Lys Leu Phe Gln Glu Lys His Val Asn Met Val His Ile Glu
                85                  90                  95

Ser Arg Lys Ser Arg Arg Arg Ser Ser Glu Val Glu Ile Phe Val Asp
                100                 105                 110

Cys Glu Cys Gly Lys Thr Glu Phe Asn Glu Leu Ile Gln Leu Leu Lys
                115                 120                 125

Phe Gln Thr Thr Ile Val Thr Leu Asn Pro Pro Glu Asn Ile Trp Thr
                130                 135                 140

Glu Glu Glu Glu Leu Glu Asp Val Pro Trp Phe Pro Arg Lys Ile Ser
145                 150                 155                 160

Glu Leu Asp Lys Cys Ser His Arg Val Leu Met Tyr Gly Ser Glu Leu
                165                 170                 175

Asp Ala Asp His Pro Gly Phe Lys Asp Asn Val Tyr Arg Gln Arg Arg
                180                 185                 190

Lys Tyr Phe Val Asp Val Ala Met Ser Tyr Lys Tyr Gly Gln Pro Ile
                195                 200                 205

Pro Arg Val Glu Tyr Thr Glu Glu Glu Thr Lys Thr Trp Gly Val Val
                210                 215                 220
```

```
Phe Arg Glu Leu Ser Arg Leu Tyr Pro Thr His Ala Cys Gln Glu Tyr
225                 230                 235                 240

Leu Lys Asn Phe Pro Leu Leu Thr Lys Tyr Cys Gly Tyr Arg Glu Asp
            245                 250                 255

Asn Val Pro Gln Leu Glu Asp Val Ser Met Phe Leu Lys Glu Arg Ser
        260                 265                 270

Gly Phe Ala Val Arg Pro Val Ala Gly Tyr Leu Ser Pro Arg Asp Phe
    275                 280                 285

Leu Ala Gly Leu Ala Tyr Arg Val Phe His Cys Thr Gln Tyr Val Arg
290                 295                 300

His Ser Ser Asp Pro Leu Tyr Thr Pro Glu Pro Asp Thr Cys His Glu
305                 310                 315                 320

Leu Leu Gly His Val Pro Leu Leu Ala Asp Pro Lys Phe Ala Gln Phe
            325                 330                 335

Ser Gln Glu Ile Gly Leu Ala Ser Leu Gly Ala Ser Asp Glu Asp Val
        340                 345                 350

Gln Lys Leu Ala Thr Cys Tyr Phe Phe Thr Ile Glu Phe Gly Leu Cys
    355                 360                 365

Lys Gln Glu Gly Gln Leu Arg Ala Tyr Gly Ala Gly Leu Leu Ser Ser
370                 375                 380

Ile Gly Glu Leu Lys His Ala Leu Ser Asp Lys Ala Cys Val Lys Ala
385                 390                 395                 400

Phe Asp Pro Lys Thr Thr Cys Leu Gln Glu Cys Leu Ile Thr Thr Phe
            405                 410                 415

Gln Glu Ala Tyr Phe Val Ser Glu Ser Phe Glu Glu Ala Lys Glu Lys
        420                 425                 430

Met Arg Glu Phe Ala Lys Ser Ile Thr Arg Pro Phe Ser Val His Phe
    435                 440                 445

Asn Pro Tyr Thr Gln Ser Val Glu Val Leu Lys Asp Ser Arg Ser Ile
450                 455                 460

Glu Ser Val Val Gln Asp Leu Arg Ser Asp Leu Asn Thr Val Cys Asp
465                 470                 475                 480

Ala Leu Asn Lys Met Asn Gln Tyr Leu Gly Val
            485                 490

<210> SEQ ID NO 9
<211> LENGTH: 497
<212> TYPE: PRT
<213> ORGANISM: Schistosoma mansoni

<400> SEQUENCE: 9

Met Ile Ser Thr Glu Ser Asp Leu Arg Arg Gln Leu Asp Glu Asn Val
1               5                   10                  15

Arg Ser Glu Ala Asp Glu Ser Thr Lys Glu Glu Cys Pro Tyr Ile Asn
            20                  25                  30

Ala Val Gln Ser His His Gln Asn Val Gln Glu Met Ser Ile Ile Ile
        35                  40                  45

Ser Leu Val Lys Asn Met Asn Asp Met Lys Ser Ile Ile Ser Ile Phe
    50                  55                  60

Thr Asp Arg Asn Ile Asn Ile Leu His Ile Glu Ser Arg Leu Gly Arg
65                  70                  75                  80

Leu Asn Met Lys Lys His Thr Glu Lys Ser Glu Phe Glu Pro Leu Glu
            85                  90                  95

Leu Leu Val His Val Glu Val Pro Cys Ile Glu Val Glu Arg Leu Leu
        100                 105                 110
```

Glu Glu Leu Lys Ser Phe Ser Ser Tyr Arg Ile Val Gln Asn Pro Leu
            115                 120                 125

Met Asn Leu Pro Glu Ala Lys Asn Pro Thr Leu Asp Asp Lys Val Pro
130                 135                 140

Trp Phe Pro Arg His Ile Ser Asp Leu Asp Lys Val Ser Asn Ser Val
145                 150                 155                 160

Leu Met Tyr Gly Lys Glu Leu Asp Ala Asp His Pro Gly Phe Lys Asp
                165                 170                 175

Lys Glu Tyr Arg Lys Arg Met Met Phe Ala Asp Ile Ala Leu Asn
            180                 185                 190

Tyr Lys Trp Gly Gln Gln Ile Pro Ile Val Glu Tyr Thr Glu Ile Glu
        195                 200                 205

Lys Thr Thr Trp Gly Arg Ile Tyr Arg Glu Leu Thr Arg Leu Tyr Lys
    210                 215                 220

Thr Ser Ala Cys His Glu Phe Gln Lys Asn Leu Gly Leu Leu Gln Asp
225                 230                 235                 240

Lys Ala Gly Tyr Asn Glu Phe Asp Leu Pro Gln Leu Gln Val Val Ser
                245                 250                 255

Asp Phe Leu Lys Ala Arg Thr Gly Phe Cys Leu Arg Pro Val Ala Gly
            260                 265                 270

Tyr Leu Ser Ala Arg Asp Phe Leu Ser Gly Leu Ala Phe Arg Val Phe
        275                 280                 285

Tyr Cys Thr Gln Tyr Ile Arg His Gln Ala Asp Pro Phe Tyr Thr Pro
    290                 295                 300

Glu Pro Asp Cys Cys His Glu Leu Leu Gly His Val Pro Met Leu Ala
305                 310                 315                 320

Asp Pro Lys Phe Ala Arg Phe Ser Gln Glu Ile Gly Leu Ala Ser Leu
                325                 330                 335

Gly Thr Ser Asp Glu Glu Ile Lys Lys Leu Ala Thr Cys Tyr Phe Phe
            340                 345                 350

Thr Ile Glu Phe Gly Leu Cys Arg Gln Asp Asn Gln Leu Lys Ala Tyr
        355                 360                 365

Gly Ala Gly Leu Leu Ser Ser Val Ala Glu Leu Gln His Ala Leu Ser
    370                 375                 380

Asp Lys Ala Val Ile Lys Pro Phe Ile Pro Met Lys Val Ile Asn Glu
385                 390                 395                 400

Glu Cys Leu Val Thr Thr Phe Gln Asn Gly Tyr Phe Glu Thr Ser Ser
                405                 410                 415

Phe Glu Asp Ala Thr Arg Gln Met Arg Glu Phe Val Arg Thr Ile Lys
            420                 425                 430

Arg Pro Phe Asp Val His Tyr Asn Pro Tyr Thr Gln Ser Ile Glu Ile
        435                 440                 445

Ile Lys Thr Pro Lys Ser Val Ala Lys Leu Val Gln Asp Leu Gln Phe
    450                 455                 460

Glu Leu Thr Ala Ile Asn Glu Ser Leu Leu Lys Met Asn Lys Glu Ile
465                 470                 475                 480

Arg Ser Gln Gln Phe Thr Thr Asn Lys Ile Val Thr Glu Asn Arg Ser
                485                 490                 495

Ser

<210> SEQ ID NO 10
<211> LENGTH: 496
<212> TYPE: PRT

<213> ORGANISM: Homo sapiens

<400> SEQUENCE: 10

Met Gln Pro Ala Met Met Phe Ser Ser Lys Tyr Trp Ala Arg Arg
1               5                   10                  15

Gly Phe Ser Leu Asp Ser Ala Val Pro Glu Glu His Gln Leu Leu Gly
            20                  25                  30

Ser Ser Thr Ala Ser Thr Phe Leu Lys Leu Asn Lys Pro Asn Ser Gly
                35                  40                  45

Lys Asn Asp Asp Lys Gly Asn Lys Gly Ser Ser Lys Arg Glu Ala Ala
        50                  55                  60

Thr Glu Ser Gly Lys Thr Ala Val Val Phe Ser Leu Lys Asn Glu Val
65                  70                  75                  80

Gly Gly Leu Val Lys Ala Leu Arg Leu Phe Gln Glu Lys Arg Val Asn
                85                  90                  95

Met Val His Ile Glu Ser Arg Lys Ser Arg Arg Ser Ser Glu Val
            100                 105                 110

Glu Ile Phe Val Asp Cys Glu Cys Gly Lys Thr Glu Phe Asn Glu Leu
            115                 120                 125

Ile Gln Leu Leu Lys Phe Gln Thr Thr Ile Val Thr Leu Asn Pro Pro
        130                 135                 140

Glu Asn Ile Trp Thr Glu Glu Glu Leu Glu Asp Val Pro Trp Phe
145                 150                 155                 160

Pro Arg Lys Ile Ser Glu Leu Asp Lys Cys Ser His Arg Val Leu Met
                165                 170                 175

Tyr Gly Ser Glu Leu Asp Ala Asp His Pro Gly Phe Lys Asp Asn Val
            180                 185                 190

Tyr Arg Gln Arg Arg Lys Tyr Phe Val Asp Val Ala Met Gly Tyr Lys
        195                 200                 205

Tyr Gly Gln Pro Ile Pro Arg Val Glu Tyr Thr Glu Glu Thr Lys
    210                 215                 220

Thr Trp Gly Val Val Phe Arg Glu Leu Ser Lys Leu Tyr Pro Thr His
225                 230                 235                 240

Ala Cys Arg Glu Tyr Leu Lys Asn Phe Pro Leu Leu Thr Lys Tyr Cys
                245                 250                 255

Gly Tyr Arg Glu Asp Asn Val Pro Gln Leu Glu Asp Val Ser Met Phe
            260                 265                 270

Leu Lys Glu Arg Ser Gly Phe Thr Val Arg Pro Val Ala Gly Tyr Leu
        275                 280                 285

Ser Pro Arg Asp Phe Leu Ala Gly Leu Ala Tyr Arg Val Phe His Cys
    290                 295                 300

Thr Gln Tyr Ile Arg His Gly Ser Asp Pro Leu Tyr Thr Pro Glu Pro
305                 310                 315                 320

Asp Thr Cys His Glu Leu Leu Gly His Val Pro Leu Leu Ala Asp Pro
                325                 330                 335

Lys Phe Ala Gln Phe Ser Gln Glu Ile Gly Leu Ala Ser Leu Gly Ala
            340                 345                 350

Ser Asp Glu Asp Val Gln Lys Leu Ala Thr Cys Tyr Phe Phe Thr Ile
        355                 360                 365

Glu Phe Gly Leu Cys Lys Gln Glu Gly Gln Leu Arg Ala Tyr Gly Ala
    370                 375                 380

Gly Leu Leu Ser Ser Ile Gly Glu Leu Lys His Ala Leu Ser Asp Lys
385                 390                 395                 400

-continued

Ala Cys Val Lys Ala Phe Asp Pro Lys Thr Thr Cys Leu Gln Glu Cys
             405                 410                 415

Leu Ile Thr Thr Phe Gln Glu Ala Tyr Phe Val Ser Glu Ser Phe Glu
             420                 425                 430

Glu Ala Lys Glu Lys Met Arg Asp Phe Ala Lys Ser Ile Thr Arg Pro
             435                 440                 445

Phe Ser Val Tyr Phe Asn Pro Tyr Thr Gln Ser Ile Glu Ile Leu Lys
             450                 455                 460

Asp Thr Arg Ser Ile Glu Asn Val Val Gln Leu Arg Ser Asp Leu
465                 470                 475                 480

Asn Thr Val Cys Asp Ala Leu Asn Lys Met Asn Gln Tyr Leu Gly Ile
             485                 490                 495

<210> SEQ ID NO 11
<211> LENGTH: 448
<212> TYPE: PRT
<213> ORGANISM: Homo sapiens

<400> SEQUENCE: 11

Met Asp Asp Lys Gly Asn Lys Gly Ser Ser Lys Arg Glu Ala Ala Thr
1               5                   10                  15

Glu Ser Gly Lys Thr Ala Val Val Phe Ser Leu Lys Asn Glu Val Gly
                20                  25                  30

Gly Leu Val Lys Ala Leu Arg Leu Phe Gln Glu Lys Arg Val Asn Met
            35                  40                  45

Val His Ile Glu Ser Arg Lys Ser Arg Arg Arg Ser Ser Glu Val Glu
        50                  55                  60

Ile Phe Val Asp Cys Glu Cys Gly Lys Thr Glu Phe Asn Glu Leu Ile
65                  70                  75                  80

Gln Leu Leu Lys Phe Gln Thr Thr Ile Val Thr Leu Asn Pro Pro Glu
                85                  90                  95

Asn Ile Trp Thr Glu Glu Glu Leu Glu Asp Val Pro Trp Phe Pro
                100                 105                 110

Arg Lys Ile Ser Glu Leu Asp Lys Cys Ser His Arg Val Leu Met Tyr
            115                 120                 125

Gly Ser Glu Leu Asp Ala Asp His Pro Gly Phe Lys Asp Asn Val Tyr
        130                 135                 140

Arg Gln Arg Arg Lys Tyr Phe Val Asp Val Ala Met Gly Tyr Lys Tyr
145                 150                 155                 160

Gly Gln Pro Ile Pro Arg Val Glu Tyr Thr Glu Glu Glu Thr Lys Thr
                165                 170                 175

Trp Gly Val Val Phe Arg Glu Leu Ser Lys Leu Tyr Pro Thr His Ala
            180                 185                 190

Cys Arg Glu Tyr Leu Lys Asn Phe Pro Leu Leu Thr Lys Tyr Cys Gly
        195                 200                 205

Tyr Arg Glu Asp Asn Val Pro Gln Leu Glu Asp Val Ser Met Phe Leu
    210                 215                 220

Lys Glu Arg Ser Gly Phe Thr Val Arg Pro Val Ala Gly Tyr Leu Ser
225                 230                 235                 240

Pro Arg Asp Phe Leu Ala Gly Leu Ala Tyr Arg Val Phe His Cys Thr
                245                 250                 255

Gln Tyr Ile Arg His Gly Ser Asp Pro Leu Tyr Thr Pro Glu Pro Asp
            260                 265                 270

Thr Cys His Glu Leu Leu Gly His Val Pro Leu Leu Ala Asp Pro Lys
        275                 280                 285

Phe Ala Gln Phe Ser Gln Glu Ile Gly Leu Ala Ser Leu Gly Ala Ser
        290                 295                 300

Asp Glu Asp Val Gln Lys Leu Ala Thr Cys Tyr Phe Phe Thr Ile Glu
305                 310                 315                 320

Phe Gly Leu Cys Lys Gln Glu Gly Gln Leu Arg Ala Tyr Gly Ala Gly
                    325                 330                 335

Leu Leu Ser Ser Ile Gly Glu Leu Lys His Ala Leu Ser Asp Lys Ala
                340                 345                 350

Cys Val Lys Ala Phe Asp Pro Lys Thr Thr Cys Leu Gln Glu Cys Leu
            355                 360                 365

Ile Thr Thr Phe Gln Glu Ala Tyr Phe Val Ser Glu Ser Phe Glu Glu
        370                 375                 380

Ala Lys Glu Lys Met Arg Asp Phe Ala Lys Ser Ile Thr Arg Pro Phe
385                 390                 395                 400

Ser Val Tyr Phe Asn Pro Tyr Thr Gln Ser Ile Glu Ile Leu Lys Asp
                    405                 410                 415

Thr Arg Ser Ile Glu Asn Val Val Gln Asp Leu Arg Ile Asn Arg Val
                420                 425                 430

His Ser Ser Ala Leu Thr Glu Lys Glu Gly Val Arg Gln Pro Glu Val
            435                 440                 445

<210> SEQ ID NO 12
<211> LENGTH: 428
<212> TYPE: PRT
<213> ORGANISM: Homo sapiens

<400> SEQUENCE: 12

Met Asp Asp Lys Gly Asn Lys Gly Ser Ser Lys Arg Glu Ala Ala Thr
1               5                   10                  15

Glu Ser Gly Lys Thr Ala Val Val Phe Ser Leu Lys Asn Glu Val Gly
                20                  25                  30

Gly Leu Val Lys Ala Leu Arg Leu Phe Gln Glu Lys Arg Val Asn Met
            35                  40                  45

Val His Ile Glu Ser Arg Lys Ser Arg Arg Arg Ser Ser Glu Val Glu
50                  55                  60

Ile Phe Val Asp Cys Glu Cys Gly Lys Thr Glu Phe Asn Glu Leu Ile
65                  70                  75                  80

Gln Leu Leu Lys Phe Gln Thr Thr Ile Val Thr Leu Asn Pro Pro Glu
                85                  90                  95

Asn Ile Trp Thr Glu Glu Glu Leu Glu Asp Val Pro Trp Phe Pro
            100                 105                 110

Arg Lys Ile Ser Glu Leu Asp Lys Cys Ser His Arg Val Leu Met Tyr
        115                 120                 125

Gly Ser Glu Leu Asp Ala Asp His Pro Gly Phe Lys Asp Asn Val Tyr
    130                 135                 140

Arg Gln Arg Arg Lys Tyr Phe Val Asp Val Ala Met Gly Tyr Lys Tyr
145                 150                 155                 160

Gly Gln Pro Ile Pro Arg Val Glu Tyr Thr Glu Glu Glu Thr Lys Thr
                165                 170                 175

Trp Gly Val Val Phe Arg Glu Leu Ser Lys Leu Tyr Pro Thr His Ala
            180                 185                 190

Cys Arg Glu Tyr Leu Lys Asn Phe Pro Leu Leu Thr Lys Tyr Cys Gly
        195                 200                 205

Tyr Arg Glu Asp Asn Val Pro Gln Leu Glu Asp Val Ser Met Phe Leu

```
                  210                 215                 220
Lys Glu Arg Ser Gly Phe Thr Val Arg Pro Val Ala Gly Tyr Leu Ser
225                 230                 235                 240

Pro Arg Asp Phe Leu Ala Gly Leu Ala Tyr Arg Val Phe His Cys Thr
                245                 250                 255

Gln Tyr Ile Arg His Gly Ser Asp Pro Leu Tyr Thr Pro Glu Pro Asp
            260                 265                 270

Thr Cys His Glu Leu Leu Gly His Val Pro Leu Leu Ala Asp Pro Lys
        275                 280                 285

Phe Ala Gln Phe Ser Gln Glu Ile Gly Leu Ala Ser Leu Gly Ala Ser
    290                 295                 300

Asp Glu Asp Val Gln Lys Leu Ala Thr Cys Tyr Phe Phe Thr Ile Glu
305                 310                 315                 320

Phe Gly Leu Cys Lys Gln Glu Gly Gln Leu Arg Ala Tyr Gly Ala Gly
                325                 330                 335

Leu Leu Ser Ser Ile Gly Glu Leu Lys His Ala Leu Ser Asp Lys Ala
                340                 345                 350

Cys Val Lys Ala Phe Asp Pro Lys Thr Thr Cys Leu Gln Glu Cys Leu
            355                 360                 365

Ile Thr Thr Phe Gln Glu Ala Tyr Phe Val Ser Glu Ser Phe Glu Glu
        370                 375                 380

Ala Lys Glu Lys Met Arg Asp Phe Ala Lys Ser Ile Thr Arg Pro Phe
385                 390                 395                 400

Ser Val Tyr Phe Asn Pro Tyr Thr Gln Ser Ile Glu Ile Leu Lys Asp
                405                 410                 415

Thr Arg Ser Ile Glu Asn Val Val Gln Asp Leu Arg
                420                 425

<210> SEQ ID NO 13
<211> LENGTH: 315
<212> TYPE: PRT
<213> ORGANISM: Homo sapiens

<400> SEQUENCE: 13

Met Glu Leu Glu Asp Val Pro Trp Phe Pro Arg Lys Ile Ser Glu Leu
1               5                   10                  15

Asp Lys Cys Ser His Arg Val Leu Met Tyr Gly Ser Glu Leu Asp Ala
                20                  25                  30

Asp His Pro Gly Phe Lys Asp Asn Val Tyr Arg Gln Arg Arg Lys Tyr
            35                  40                  45

Phe Val Asp Val Ala Met Gly Tyr Lys Tyr Gly Gln Pro Ile Pro Arg
    50                  55                  60

Val Glu Tyr Thr Glu Glu Thr Lys Thr Trp Gly Val Val Phe Arg
65                  70                  75                  80

Glu Leu Ser Lys Leu Tyr Pro Thr His Ala Cys Arg Glu Tyr Leu Lys
                85                  90                  95

Asn Phe Pro Leu Leu Thr Lys Tyr Cys Gly Tyr Arg Glu Asp Asn Val
                100                 105                 110

Pro Gln Leu Glu Asp Val Ser Met Phe Leu Lys Glu Arg Ser Gly Phe
            115                 120                 125

Thr Val Arg Pro Val Ala Gly Tyr Leu Ser Pro Arg Asp Phe Leu Ala
        130                 135                 140

Gly Leu Ala Tyr Arg Val Phe His Cys Thr Gln Tyr Ile Arg His Gly
145                 150                 155                 160
```

```
Ser Asp Pro Leu Tyr Thr Pro Glu Pro Asp Thr Cys His Glu Leu Leu
            165                 170                 175

Gly His Val Pro Leu Leu Ala Asp Pro Lys Phe Ala Gln Phe Ser Gln
        180                 185                 190

Glu Ile Gly Leu Ala Ser Leu Gly Ala Ser Asp Glu Asp Val Gln Lys
            195                 200                 205

Leu Ala Thr Cys Tyr Phe Phe Thr Ile Glu Phe Gly Leu Cys Lys Gln
        210                 215                 220

Glu Gly Gln Leu Arg Ala Tyr Gly Ala Gly Leu Leu Ser Ser Ile Gly
225                 230                 235                 240

Glu Leu Lys His Ala Leu Ser Asp Lys Ala Cys Val Lys Ala Phe Asp
            245                 250                 255

Pro Lys Thr Thr Cys Leu Gln Glu Cys Leu Ile Thr Thr Phe Gln Glu
        260                 265                 270

Ala Tyr Phe Val Ser Glu Ser Phe Glu Ala Lys Glu Lys Met Arg
            275                 280                 285

Asp Phe Ala Lys Ser Ile Thr Arg Pro Phe Ser Val Tyr Phe Asn Pro
        290                 295                 300

Tyr Thr Gln Ser Ile Glu Ile Leu Lys Asp Thr
305                 310                 315

<210> SEQ ID NO 14
<211> LENGTH: 250
<212> TYPE: PRT
<213> ORGANISM: Homo sapiens

<400> SEQUENCE: 14

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr His Met Cys Met Val Met Arg Gly Val Gln Lys Met Asn Ser Lys
    210                 215                 220
```

```
Thr Val Thr Ser Thr Met Leu Gly Val Phe Arg Glu Asp Pro Lys Thr
225                 230                 235                 240

Arg Glu Glu Phe Leu Thr Leu Ile Arg Ser
            245                 250
```

<210> SEQ ID NO 15
<211> LENGTH: 241
<212> TYPE: PRT
<213> ORGANISM: Mus musculus

<400> SEQUENCE: 15

```
Met Glu Lys Pro Arg Gly Val Arg Cys Thr Asn Gly Phe Ser Glu Arg
1               5                   10                  15

Glu Leu Pro Arg Pro Gly Ala Ser Pro Ala Glu Lys Ser Arg Pro
            20                  25                  30

Pro Glu Ala Lys Gly Ala Gln Pro Ala Asp Ala Trp Lys Ala Gly Arg
            35                  40                  45

His Arg Ser Glu Glu Asn Gln Val Asn Leu Pro Lys Leu Ala Ala
    50                  55                  60

Ala Tyr Ser Ser Ile Leu Leu Ser Leu Gly Glu Asp Pro Gln Arg Gln
65                  70                  75                  80

Gly Leu Leu Lys Thr Pro Trp Arg Ala Ala Thr Ala Met Gln Tyr Phe
                85                  90                  95

Thr Lys Gly Tyr Gln Glu Thr Ile Ser Asp Val Leu Asn Asp Ala Ile
                100                 105                 110

Phe Asp Glu Asp His Asp Glu Met Val Ile Val Lys Asp Ile Asp Met
            115                 120                 125

Phe Ser Met Cys Glu His His Leu Val Pro Phe Val Gly Arg Val His
130                 135                 140

Ile Gly Tyr Leu Pro Asn Lys Gln Val Leu Gly Leu Ser Lys Leu Ala
145                 150                 155                 160

Arg Ile Val Glu Ile Tyr Ser Arg Arg Leu Gln Val Gln Glu Arg Leu
                165                 170                 175

Thr Lys Gln Ile Ala Val Ala Ile Thr Glu Ala Leu Gln Pro Ala Gly
            180                 185                 190

Val Gly Val Val Ile Glu Ala Thr His Met Cys Met Val Met Arg Gly
        195                 200                 205

Val Gln Lys Met Asn Ser Lys Thr Val Thr Ser Thr Met Leu Gly Val
210                 215                 220

Phe Arg Glu Asp Pro Lys Thr Arg Glu Glu Phe Leu Thr Leu Ile Arg
225                 230                 235                 240

Ser
```

<210> SEQ ID NO 16
<211> LENGTH: 222
<212> TYPE: PRT
<213> ORGANISM: Escherichia coli

<400> SEQUENCE: 16

```
Met Pro Ser Leu Ser Lys Glu Ala Ala Leu Val His Glu Ala Leu Val
1               5                   10                  15

Ala Arg Gly Leu Glu Thr Pro Leu Arg Pro Pro Val His Glu Met Asp
            20                  25                  30

Asn Glu Thr Arg Lys Ser Leu Ile Ala Gly His Met Thr Glu Ile Met
            35                  40                  45
```

```
Gln Leu Leu Asn Leu Asp Leu Ala Asp Asp Ser Leu Met Glu Thr Pro
 50                  55                  60

His Arg Ile Ala Lys Met Tyr Val Asp Glu Ile Phe Ser Gly Leu Asp
 65                  70                  75                  80

Tyr Ala Asn Phe Pro Lys Ile Thr Leu Ile Glu Asn Lys Met Lys Val
                 85                  90                  95

Asp Glu Met Val Thr Val Arg Asp Ile Thr Leu Thr Ser Thr Cys Glu
            100                 105                 110

His His Phe Val Thr Ile Asp Gly Lys Ala Thr Val Ala Tyr Ile Pro
        115                 120                 125

Lys Asp Ser Val Ile Gly Leu Ser Lys Ile Asn Arg Ile Val Gln Phe
130                 135                 140

Phe Ala Gln Arg Pro Gln Val Gln Glu Arg Leu Thr Gln Gln Ile Leu
145                 150                 155                 160

Ile Ala Leu Gln Thr Leu Leu Gly Thr Asn Asn Val Ala Val Ser Ile
                165                 170                 175

Asp Ala Val His Tyr Cys Val Lys Ala Arg Gly Ile Arg Asp Ala Thr
            180                 185                 190

Ser Ala Thr Thr Thr Thr Ser Leu Gly Gly Leu Phe Lys Ser Ser Gln
        195                 200                 205

Asn Thr Arg His Glu Phe Leu Arg Ala Val Arg His His Asn
210                 215                 220

<210> SEQ ID NO 17
<211> LENGTH: 243
<212> TYPE: PRT
<213> ORGANISM: Saccharomyces cerevisiae

<400> SEQUENCE: 17

Met His Asn Ile Gln Leu Val Gln Glu Ile Glu Arg His Glu Thr Pro
  1               5                  10                  15

Leu Asn Ile Arg Pro Thr Ser Pro Tyr Thr Leu Asn Pro Pro Val Glu
                 20                  25                  30

Arg Asp Gly Phe Ser Trp Pro Ser Val Gly Thr Arg Gln Arg Ala Glu
             35                  40                  45

Glu Thr Glu Glu Glu Glu Lys Glu Arg Ile Gln Arg Ile Ser Gly Ala
 50                  55                  60

Ile Lys Thr Ile Leu Thr Glu Leu Gly Glu Asp Val Asn Arg Glu Gly
 65                  70                  75                  80

Leu Leu Asp Thr Pro Gln Arg Tyr Ala Lys Ala Met Leu Tyr Phe Thr
                 85                  90                  95

Lys Gly Tyr Gln Thr Asn Ile Met Asp Asp Val Ile Lys Asn Ala Val
            100                 105                 110

Phe Glu Glu Asp His Asp Glu Met Val Ile Val Arg Asp Ile Glu Ile
        115                 120                 125

Tyr Ser Leu Cys Glu His His Leu Val Pro Phe Phe Gly Lys Val His
130                 135                 140

Ile Gly Tyr Ile Pro Asn Lys Lys Val Ile Gly Leu Ser Lys Leu Ala
145                 150                 155                 160

Arg Leu Ala Glu Met Tyr Ala Arg Arg Leu Gln Val Gln Glu Arg Leu
                165                 170                 175

Thr Lys Gln Ile Ala Met Ala Leu Ser Asp Ile Leu Lys Pro Leu Gly
            180                 185                 190

Val Ala Val Val Met Glu Ala Ser His Met Cys Met Val Ser Arg Gly
        195                 200                 205
```

Ile Gln Lys Thr Gly Ser Ser Thr Val Thr Ser Cys Met Leu Gly Gly
210                 215                 220

Phe Arg Ala His Lys Thr Arg Glu Glu Phe Leu Thr Leu Leu Gly Arg
225                 230                 235                 240

Arg Ser Ile

<210> SEQ ID NO 18
<211> LENGTH: 190
<212> TYPE: PRT
<213> ORGANISM: Bacillus subtilis

<400> SEQUENCE: 18

Met Lys Glu Val Asn Lys Glu Gln Ile Glu Gln Ala Val Arg Gln Ile
1               5                   10                  15

Leu Glu Ala Ile Gly Glu Asp Pro Asn Arg Gly Leu Leu Asp Thr
            20                  25                  30

Pro Lys Arg Val Ala Lys Met Tyr Ala Glu Val Phe Ser Gly Leu Asn
            35                  40                  45

Glu Asp Pro Lys Glu His Phe Gln Thr Ile Phe Gly Glu Asn His Glu
    50                  55                  60

Glu Leu Val Leu Val Lys Asp Ile Ala Phe His Ser Met Cys Glu His
65                  70                  75                  80

His Leu Val Pro Phe Tyr Gly Lys Ala His Val Ala Tyr Ile Pro Arg
                85                  90                  95

Gly Gly Lys Val Thr Gly Leu Ser Lys Leu Ala Arg Ala Val Glu Ala
            100                 105                 110

Val Ala Lys Arg Pro Gln Leu Gln Glu Arg Ile Thr Ser Thr Ile Ala
        115                 120                 125

Glu Ser Ile Val Glu Thr Leu Asp Pro His Gly Val Met Val Val Val
    130                 135                 140

Glu Ala Glu His Met Cys Met Thr Met Arg Gly Val Arg Lys Pro Gly
145                 150                 155                 160

Ala Lys Thr Val Thr Ser Ala Val Arg Gly Val Phe Lys Asp Asp Ala
                165                 170                 175

Ala Ala Arg Ala Glu Val Leu Glu His Ile Lys Arg Gln Asp
            180                 185                 190

<210> SEQ ID NO 19
<211> LENGTH: 201
<212> TYPE: PRT
<213> ORGANISM: Streptomyces avermitilis

<400> SEQUENCE: 19

Met Thr Asp Pro Val Thr Leu Asp Gly Glu Gly Thr Ile Gly Glu Phe
1               5                   10                  15

Asp Glu Lys Arg Ala Glu Asn Ala Val Arg Glu Leu Leu Ile Ala Val
            20                  25                  30

Gly Glu Asp Pro Asp Arg Glu Gly Leu Arg Glu Thr Pro Gly Arg Val
            35                  40                  45

Ala Arg Ala Tyr Arg Glu Ile Phe Ala Gly Leu Trp Gln Lys Pro Glu
    50                  55                  60

Asp Val Leu Thr Thr Thr Phe Asp Ile Gly His Asp Glu Met Val Leu
65                  70                  75                  80

Val Lys Asp Ile Glu Val Leu Ser Ser Cys Glu His His Leu Val Pro
                85                  90                  95

```
Phe Val Gly Val Ala His Val Gly Tyr Ile Pro Ser Thr Asp Gly Lys
                100                 105                 110

Ile Thr Gly Leu Ser Lys Leu Ala Arg Leu Val Asp Val Tyr Ala Arg
            115                 120                 125

Arg Pro Gln Val Gln Glu Arg Leu Thr Thr Gln Val Ala Asp Ser Leu
        130                 135                 140

Met Glu Ile Leu Glu Pro Arg Gly Val Ile Val Val Glu Cys Glu
145                 150                 155                 160

His Met Cys Met Ser Met Arg Gly Val Arg Lys Pro Gly Ala Lys Thr
                165                 170                 175

Ile Thr Ser Ala Val Arg Gly Gln Leu Arg Asp Pro Ala Thr Arg Asn
            180                 185                 190

Glu Ala Met Ser Leu Ile Met Ala Arg
        195                 200

<210> SEQ ID NO 20
<211> LENGTH: 222
<212> TYPE: PRT
<213> ORGANISM: Salmonella typhi

<400> SEQUENCE: 20

Met Pro Ser Leu Ser Lys Glu Ala Ala Leu Val His Asp Ala Leu Val
1               5                   10                  15

Ala Arg Gly Leu Glu Thr Pro Leu Arg Pro Pro Met Asp Glu Leu Asp
                20                  25                  30

Asn Glu Thr Arg Lys Ser Leu Ile Ala Gly His Met Thr Glu Ile Met
            35                  40                  45

Gln Leu Leu Asn Leu Asp Leu Ser Asp Ser Leu Met Glu Thr Pro
    50                  55                  60

His Arg Ile Ala Lys Met Tyr Val Asp Glu Ile Phe Ala Gly Leu Asp
65                  70                  75                  80

Tyr Ala Asn Phe Pro Lys Ile Thr Leu Ile Glu Asn Lys Met Lys Val
                85                  90                  95

Asp Glu Met Val Thr Val Arg Asp Ile Thr Leu Thr Ser Thr Cys Glu
                100                 105                 110

His His Phe Val Thr Ile Asp Gly Lys Ala Thr Val Ala Tyr Ile Pro
            115                 120                 125

Lys Asp Ser Val Ile Gly Leu Ser Lys Ile Asn Arg Ile Val Gln Phe
        130                 135                 140

Phe Ala Gln Arg Pro Gln Val Gln Glu Arg Leu Thr Gln Gln Ile Leu
145                 150                 155                 160

Thr Ala Leu Gln Thr Leu Leu Gly Thr Asn Asn Val Ala Val Ser Ile
                165                 170                 175

Asp Ala Val His Tyr Cys Val Lys Ala Arg Gly Ile Arg Asp Ala Thr
            180                 185                 190

Ser Ala Thr Thr Thr Thr Ser Leu Gly Gly Leu Phe Lys Ser Ser Gln
        195                 200                 205

Asn Thr Arg Gln Glu Phe Leu Arg Ala Val Arg His His Pro
    210                 215                 220

<210> SEQ ID NO 21
<211> LENGTH: 108
<212> TYPE: PRT
<213> ORGANISM: Chromobacterium violaceum

<400> SEQUENCE: 21
```

-continued

```
Met Asn Leu Leu Glu Leu Ser Cys Thr Pro Gln His Gly Gln Ser Pro
1               5                   10                  15

Leu Ala Asp Asn Thr Val Lys Gln Leu Leu Ser Thr Leu Pro Asp Trp
            20                  25                  30

Glu Ile Val Gly Ile Glu Leu Arg Lys Thr Tyr Arg Phe Ala Asn Tyr
        35                  40                  45

His Glu Thr Met Ala Phe Val Asn Ala Leu Ala Trp Ile Ala Asn Gln
    50                  55                  60

Glu Asp His His Pro Asp Met Ser Val His Tyr Asn Arg Ala Val Val
65                  70                  75                  80

Asn Phe Ser Thr His Asp Ala Gly Gly Leu Thr Leu Asn Asp Phe Ile
                85                  90                  95

Cys Ala Ala Lys Thr Glu Ala Leu Phe Arg Arg Pro
            100                 105
```

<210> SEQ ID NO 22
<211> LENGTH: 118
<212> TYPE: PRT
<213> ORGANISM: Pseudomonas aeruginosa

<400> SEQUENCE: 22

```
Met Thr Ala Leu Thr Gln Ala His Cys Glu Ala Cys Arg Ala Asp Ala
1               5                   10                  15

Pro His Val Ser Asp Glu Glu Leu Pro Val Leu Leu Arg Gln Ile Pro
            20                  25                  30

Asp Trp Asn Ile Glu Val Arg Asp Gly Ile Met Gln Leu Glu Lys Val
        35                  40                  45

Tyr Leu Phe Lys Asn Phe Lys His Ala Leu Ala Phe Thr Asn Ala Val
    50                  55                  60

Gly Glu Ile Ser Glu Ala Glu Gly His His Pro Gly Leu Leu Thr Glu
65                  70                  75                  80

Trp Gly Lys Val Thr Val Thr Trp Trp Ser His Ser Ile Lys Gly Leu
                85                  90                  95

His Arg Asn Asp Phe Ile Met Ala Ala Arg Thr Asp Glu Val Ala Lys
            100                 105                 110

Thr Ala Glu Gly Arg Lys
            115
```

<210> SEQ ID NO 23
<211> LENGTH: 104
<212> TYPE: PRT
<213> ORGANISM: Bacillus cereus var. anthracis

<400> SEQUENCE: 23

```
Met Met Leu Arg Leu Thr Glu Glu Val Gln Glu Glu Leu Leu Lys
1               5                   10                  15

Leu Asp Lys Trp Val Val Lys Asp Glu Lys Trp Ile Glu Arg Lys Tyr
            20                  25                  30

Met Phe Ser Asp Tyr Leu Lys Gly Val Glu Phe Val Ser Glu Ala Ala
        35                  40                  45

Lys Leu Ser Glu Glu His Asn His His Pro Phe Ile Leu Ile Gln Tyr
    50                  55                  60

Lys Ala Val Ile Ile Thr Leu Ser Ser Trp Asn Ala Lys Gly Leu Thr
65                  70                  75                  80

Lys Leu Asp Phe Glu Leu Ala Lys Gln Phe Asp Glu Leu Phe Val Gln
                85                  90                  95
```

```
Asn Glu Lys Ala Val Ile Arg Lys
            100

<210> SEQ ID NO 24
<211> LENGTH: 188
<212> TYPE: PRT
<213> ORGANISM: Corynebacterium genitalium

<400> SEQUENCE: 24

Met Ser Asp Thr Leu Asp Ala Leu Asp Ile His Glu Pro Asp Glu Ala
1               5                   10                  15

Phe Leu Met Ala Thr Glu Ala Glu Val Glu Val Pro Ser Gln Pro Cys
            20                  25                  30

Ala Leu Ala Val Leu Val Ser Asp His Lys Gln Gly Gly Ala Ile Asp
        35                  40                  45

Glu Gly Thr Asp Arg Leu Val Phe Glu Leu Leu Gln Glu Ile Gly Phe
    50                  55                  60

Lys Val Asp Gly Val Val Tyr Val Lys Ser Lys Lys Ser Glu Ile Arg
65                  70                  75                  80

Lys Val Ile Glu Thr Ala Val Val Gly Gly Val Asp Leu Val Val Thr
                85                  90                  95

Val Gly Gly Thr Gly Val Gly Pro Arg Asp Lys Ala Pro Glu Ala Thr
            100                 105                 110

Arg Gly Val Ile Asp Gln Leu Val Pro Gly Val Ala Gln Ala Val Arg
        115                 120                 125

Ala Ser Gly Gln Ala Cys Gly Ala Val Asp Ala Cys Thr Ser Arg Gly
    130                 135                 140

Ile Cys Gly Val Ser Gly Ser Thr Val Val Asn Leu Ala Pro Ser
145                 150                 155                 160

Arg Ala Ala Ile Arg Asp Gly Ile Ser Thr Ile Ser Pro Leu Val Ala
                165                 170                 175

His Leu Ile Ser Glu Leu Arg Lys Tyr Ser Val Gln
            180                 185

<210> SEQ ID NO 25
<211> LENGTH: 63
<212> TYPE: PRT
<213> ORGANISM: Lactobacillus ruminis

<400> SEQUENCE: 25

Met Val Lys Leu Phe Pro Ser Glu Asn Ala Arg Arg Trp His Arg Trp
1               5                   10                  15

Asn His Glu Val Leu Leu Leu Val Asn Ile Gln Cys Ser Leu Lys Gln
            20                  25                  30

Pro Leu Trp Ser Ala Glu Gly Lys Val Asp Lys Asn Arg Glu Lys Cys
        35                  40                  45

Ala Ala Phe Val Tyr Arg Leu Val Glu Ile Gln Asp Ala Arg Ile
    50                  55                  60

<210> SEQ ID NO 26
<211> LENGTH: 96
<212> TYPE: PRT
<213> ORGANISM: Rhodobacteraceae bacterium

<400> SEQUENCE: 26

Met Ser Glu Arg Leu Phe Asp Asp Thr Arg Gly Pro Leu Leu Asp Pro
1               5                   10                  15

Leu Phe Ala Thr Gly Trp Ala Met Val Glu Gly Arg Asp Ala Ile Glu
```

```
                    20                  25                  30
Lys His Tyr Lys Phe Lys Asn Phe Ala Asp Ala Phe Gly Trp Met Thr
            35                  40                  45

Arg Ala Ala Ile Trp Ser Glu Lys Trp Asp His His Pro Glu Trp Leu
    50                  55                  60

Asn Val Tyr Asn Lys Val His Val Val Leu Thr Thr His Ser Val Asp
65                  70                  75                  80

Gly Leu Ser Pro Leu Asp Val Lys Leu Ala Arg Lys Phe Asp Ser Leu
                85                  90                  95

<210> SEQ ID NO 27
<211> LENGTH: 104
<212> TYPE: PRT
<213> ORGANISM: Homo sapiens

<400> SEQUENCE: 27

Met Ala Gly Lys Ala His Arg Leu Ser Ala Glu Glu Arg Asp Gln Leu
1               5                   10                  15

Leu Pro Asn Leu Arg Ala Val Gly Trp Asn Glu Leu Glu Gly Arg Asp
                20                  25                  30

Ala Ile Phe Lys Gln Phe His Phe Lys Asp Phe Asn Arg Ala Phe Gly
            35                  40                  45

Phe Met Thr Arg Val Ala Leu Gln Ala Glu Lys Leu Asp His His Pro
    50                  55                  60

Glu Trp Phe Asn Val Tyr Asn Lys Val His Ile Thr Leu Ser Thr His
65                  70                  75                  80

Glu Cys Ala Gly Leu Ser Glu Arg Asp Ile Asn Leu Ala Ser Phe Ile
                85                  90                  95

Glu Gln Val Ala Val Ser Met Thr
                100

<210> SEQ ID NO 28
<211> LENGTH: 430
<212> TYPE: PRT
<213> ORGANISM: Acidobacterium capsulatum

<400> SEQUENCE: 28

Ser Ala Gly Gln Ala Tyr Ala Asp Tyr Leu His Leu Val Gln Pro Tyr
1               5                   10                  15

Thr Asn Gly Asn Arg His Pro Arg Ala Trp Gly Trp Val Arg Gly Asn
                20                  25                  30

Gly Thr Pro Ile Gly Ala Met Ala Glu Met Leu Ala Ala Ala Ile Asn
            35                  40                  45

Pro His Leu Gly Gly Gly Asp Gln Ser Pro Thr Tyr Val Glu Glu Arg
    50                  55                  60

Cys Leu Gln Trp Leu Ala Gln Val Met Gly Met Pro Ala Thr Ala Thr
65                  70                  75                  80

Gly Ile Leu Thr Ser Gly Gly Thr Met Ala Asn Leu Leu Gly Leu Ala
                85                  90                  95

Val Ala Arg His Ala Lys Ala Gly Phe Asp Val Arg Ala Glu Gly Leu
                100                 105                 110

Ala Ala His Thr Pro Leu Thr Val Tyr Ala Ser Ser Glu Ala His Met
            115                 120                 125

Trp Ala Gly Asn Ala Met Asp Leu Leu Gly Leu Gly Ser Ser Arg Leu
    130                 135                 140

Arg Ser Ile Pro Val Asp Glu Asn Phe Arg Ile Asp Leu Ala Ala Leu
```

```
                145                 150                 155                 160
Arg Leu Lys Ile Arg Glu Asp Arg Ala Ala Gly Leu Gln Pro Ile Ala
                165                 170                 175

Val Ile Gly Asn Ala Gly Thr Val Asn Thr Gly Ala Val Asp Asp Leu
            180                 185                 190

Glu Ala Leu Ala Ala Leu Cys Arg Glu Glu Leu Trp Phe His Val
        195                 200                 205

Asp Gly Ala Phe Gly Ala Leu Leu Lys Leu Ser Pro Arg His Ala Ser
    210                 215                 220

Leu Val Arg Gly Leu Glu Gln Ala Asp Ser Leu Ala Phe Asp Leu His
225                 230                 235                 240

Lys Trp Met Tyr Leu Pro Phe Glu Ile Gly Cys Val Leu Val Ala Asn
                245                 250                 255

Gly Glu Glu His Arg Ala Ala Phe Ala Ser Ser Ala Ser Tyr Leu Glu
            260                 265                 270

Gly Ala Lys Arg Gly Ile Leu Ala Thr Gly Leu Ile Phe Ala Asp Arg
        275                 280                 285

Gly Leu Glu Leu Thr Arg Gly Phe Lys Ala Leu Lys Leu Trp Met Ala
    290                 295                 300

Leu Lys Ala His Gly Leu Asn Ala Phe Ser Glu Met Ile Glu Gln Asn
305                 310                 315                 320

Met Ala Gln Ala Arg Tyr Leu Glu Arg Val Leu Glu Glu Pro Glu
                325                 330                 335

Leu Glu Leu Leu Ala Pro Arg Ser Met Asn Ile Val Cys Phe Arg Tyr
            340                 345                 350

Arg Gly Arg Gly Ala Ala Gly Asp Glu Leu Leu Asn Ala Leu Asn Arg
        355                 360                 365

Glu Leu Val Leu Arg Leu Gln Glu Ser Gly Glu Phe Val Val Ser Gly
    370                 375                 380

Thr Met Leu Lys Gly Arg Tyr Ala Leu Arg Ile Ala Asn Thr Asn His
385                 390                 395                 400

Arg Ser Arg Leu Gln Asp Phe Glu Asp Leu Val Gln Trp Ser Leu Lys
                405                 410                 415

Leu Gly Cys Glu Ile Glu Ala Glu Ser Gln Ala Ala Arg Thr
            420                 425                 430

<210> SEQ ID NO 29
<211> LENGTH: 480
<212> TYPE: PRT
<213> ORGANISM: Rattus norvegicus

<400> SEQUENCE: 29

Met Asp Ser Arg Glu Phe Arg Arg Gly Lys Glu Met Val Asp Tyr
1               5                   10                  15

Ile Ala Asp Tyr Leu Asp Gly Ile Glu Gly Arg Pro Val Tyr Pro Asp
                20                  25                  30

Val Glu Pro Gly Tyr Leu Arg Ala Leu Ile Pro Thr Thr Ala Pro Gln
            35                  40                  45

Glu Pro Glu Thr Tyr Glu Asp Ile Ile Arg Asp Ile Glu Lys Ile Ile
        50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95
```

Ala Ile Gly Cys Ile Gly Phe Ser Trp Ala Ala Ser Pro Ala Cys Thr
                100                 105                 110

Glu Leu Glu Thr Val Met Met Asp Trp Leu Gly Lys Met Leu Glu Leu
            115                 120                 125

Pro Glu Ala Phe Leu Ala Gly Arg Ala Gly Glu Gly Gly Val Ile
        130                 135                 140

Gln Gly Ser Ala Ser Glu Ala Thr Leu Val Ala Leu Ala Ala Arg
145                 150                 155                 160

Thr Lys Met Ile Arg Gln Leu Gln Ala Ser Pro Glu Leu Thr Gln
                165                 170                 175

Ala Ala Leu Met Glu Lys Leu Val Ala Tyr Thr Ser Asp Gln Ala His
            180                 185                 190

Ser Ser Val Glu Arg Ala Gly Leu Ile Gly Gly Val Lys Ile Lys Ala
            195                 200                 205

Ile Pro Ser Asp Gly Asn Tyr Ser Met Arg Ala Ala Ala Leu Arg Glu
        210                 215                 220

Ala Leu Glu Arg Asp Lys Ala Ala Gly Leu Ile Pro Phe Phe Val Val
225                 230                 235                 240

Val Thr Leu Gly Thr Thr Ser Cys Cys Ser Phe Asp Asn Leu Leu Glu
            245                 250                 255

Val Gly Pro Ile Cys Asn Gln Glu Gly Val Trp Leu His Ile Asp Ala
            260                 265                 270

Ala Tyr Ala Gly Ser Ala Phe Ile Cys Pro Glu Phe Arg Tyr Leu Leu
        275                 280                 285

Asn Gly Val Glu Phe Ala Asp Ser Phe Asn Phe Asn Pro His Lys Trp
        290                 295                 300

Leu Leu Val Asn Phe Asp Cys Ser Ala Met Trp Val Lys Lys Arg Thr
305                 310                 315                 320

Asp Leu Thr Glu Ala Phe Asn Met Asp Pro Val Tyr Leu Arg His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Lys Leu
        370                 375                 380

Ser His Glu Phe Glu Ser Leu Val Arg Gln Asp Pro Arg Phe Glu Ile
385                 390                 395                 400

Cys Thr Glu Val Ile Leu Gly Leu Val Cys Phe Arg Leu Lys Gly Ser
                405                 410                 415

Asn Gln Leu Asn Glu Thr Leu Leu Gln Arg Ile Asn Ser Ala Lys Lys
            420                 425                 430

Ile His Leu Val Pro Cys Arg Leu Arg Asp Lys Phe Val Leu Arg Phe
        435                 440                 445

Ala Val Cys Ser Arg Thr Val Gly Ser Ala His Val Gln Leu Ala Trp
        450                 455                 460

Glu His Ile Arg Asp Leu Ala Ser Ser Val Leu Arg Ala Glu Lys Glu
465                 470                 475                 480

<210> SEQ ID NO 30
<211> LENGTH: 486
<212> TYPE: PRT
<213> ORGANISM: Sus scrofa

<400> SEQUENCE: 30

```
Met Asn Ala Ser Asp Phe Arg Arg Gly Lys Glu Met Val Asp Tyr
1               5                   10                  15

Met Ala Asp Tyr Leu Glu Gly Ile Glu Gly Arg Gln Val Tyr Pro Asp
                20                  25                  30

Val Gln Pro Gly Tyr Leu Arg Pro Leu Ile Pro Ala Thr Ala Pro Gln
        35                  40                  45

Glu Pro Asp Thr Phe Glu Asp Ile Leu Gln Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Gln Leu
        115                 120                 125

Pro Glu Ala Phe Leu Ala Gly Glu Ala Gly Glu Gly Gly Val Ile
    130                 135                 140

Gln Gly Ser Ala Ser Glu Ala Thr Leu Val Ala Leu Leu Ala Ala Arg
145                 150                 155                 160

Thr Lys Val Val Arg Arg Leu Gln Ala Ala Ser Pro Gly Leu Thr Gln
                165                 170                 175

Gly Ala Val Leu Glu Lys Leu Val Ala Tyr Ala Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Lys Phe Ala Met Arg Ala Ser Ala Leu Gln Glu
    210                 215                 220

Ala Leu Glu Arg Asp Lys Ala Ala Gly Leu Ile Pro Phe Phe Val Val
225                 230                 235                 240

Ala Thr Leu Gly Thr Thr Ser Cys Cys Ser Phe Asp Asn Leu Leu Glu
                245                 250                 255

Val Gly Pro Ile Cys His Glu Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Arg Arg Thr
305                 310                 315                 320

Asp Leu Thr Gly Ala Phe Lys Leu Asp Pro Val Tyr Leu Lys His Ser
                325                 330                 335

His Gln Gly Ser Gly Leu Ile Thr Asp Tyr Arg His Trp Gln Leu Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ala Phe Val Leu Gln Asp Pro Arg Phe Glu Val
385                 390                 395                 400

Cys Ala Glu Val Thr Leu Gly Leu Val Cys Phe Arg Leu Lys Gly Ser
                405                 410                 415
```

-continued

Asp Gly Leu Asn Glu Ala Leu Leu Glu Arg Ile Asn Ser Ala Arg Lys
            420                 425                 430

Ile His Leu Val Pro Cys Arg Leu Arg Gly Gln Phe Val Leu Arg Phe
            435                 440                 445

Ala Ile Cys Ser Arg Lys Val Glu Ser Gly His Val Arg Leu Ala Trp
            450                 455                 460

Glu His Ile Arg Gly Leu Ala Ala Glu Leu Leu Ala Ala Glu Glu Gly
465                 470                 475                 480

Lys Ala Glu Ile Lys Ser
            485

<210> SEQ ID NO 31
<211> LENGTH: 480
<212> TYPE: PRT
<213> ORGANISM: Homo sapiens

<400> SEQUENCE: 31

Met Asn Ala Ser Glu Phe Arg Arg Gly Lys Glu Met Val Asp Tyr
1               5                   10                  15

Met Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Ala Pro Gln
            35                  40                  45

Glu Pro Asp Thr Phe Glu Asp Ile Ile Asn Asp Val Glu Lys Ile Ile
50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
            115                 120                 125

Pro Lys Ala Phe Leu Asn Glu Lys Ala Gly Glu Gly Gly Val Ile
130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Gly Val Lys Leu Lys Ala
            195                 200                 205

Ile Pro Ser Asp Gly Asn Phe Ala Met Arg Ala Ser Ala Leu Gln Glu
210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
            275                 280                 285

Asn Gly Val Glu Phe Ala Asp Ser Phe Asn Phe Asn Pro His Lys Trp
290                 295                 300

```
Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
                420                 425                 430

Ile His Leu Val Pro Cys His Leu Arg Asp Lys Phe Val Leu Arg Phe
                435                 440                 445

Ala Ile Cys Ser Arg Thr Val Glu Ser Ala His Val Gln Arg Ala Trp
                450                 455                 460

Glu His Ile Lys Glu Leu Ala Ala Asp Val Leu Arg Ala Glu Arg Glu
465                 470                 475                 480

<210> SEQ ID NO 32
<211> LENGTH: 503
<212> TYPE: PRT
<213> ORGANISM: Capsicum annuum

<400> SEQUENCE: 32

Met Gly Ser Leu Asp Ser Asn Asn Ser Thr Gln Thr Gln Ser Asn Val
1               5                   10                  15

Thr Lys Phe Asn Pro Leu Asp Pro Glu Glu Phe Arg Thr Gln Ala His
            20                  25                  30

Gln Met Val Asp Phe Ile Ala Asp Tyr Tyr Lys Asn Ile Glu Ser Tyr
        35                  40                  45

Pro Val Leu Ser Gln Val Glu Pro Gly Tyr Leu Arg Asn His Leu Pro
    50                  55                  60

Glu Asn Ala Pro Tyr Leu Pro Glu Ser Leu Asp Thr Ile Met Lys Asp
65                  70                  75                  80

Val Glu Lys His Ile Ile Pro Gly Met Thr His Trp Leu Ser Pro Asn
                85                  90                  95

Phe Phe Ala Phe Phe Pro Ala Thr Val Ser Ser Ala Ala Phe Leu Gly
            100                 105                 110

Glu Met Leu Cys Asn Cys Phe Asn Ser Val Gly Phe Asn Trp Leu Ala
        115                 120                 125

Ser Pro Ala Met Thr Glu Leu Glu Met Ile Met Asp Trp Leu Ala
    130                 135                 140

Asn Met Leu Lys Leu Pro Glu Cys Phe Met Phe Ser Gly Thr Gly Gly
145                 150                 155                 160

Gly Val Ile Gln Gly Thr Thr Ser Glu Ala Ile Leu Cys Thr Leu Ile
                165                 170                 175

Ala Ala Arg Asp Arg Lys Leu Glu Asn Ile Gly Val Asp Asn Ile Gly
            180                 185                 190

Lys Leu Val Val Tyr Gly Ser Asp Gln Thr His Ser Met Tyr Ala Lys
```

```
                195                 200                 205
Ala Cys Lys Ala Ala Gly Ile Phe Pro Cys Asn Ile Arg Ala Ile Ser
    210                 215                 220

Thr Cys Val Glu Asn Asp Phe Ser Leu Ser Pro Ala Val Leu Arg Gly
225                 230                 235                 240

Ile Val Glu Val Asp Val Ala Ala Gly Leu Val Pro Leu Phe Leu Cys
                245                 250                 255

Ala Thr Val Gly Thr Thr Ser Thr Thr Ala Ile Asp Pro Ile Ser Glu
            260                 265                 270

Leu Gly Glu Leu Ala Asn Glu Phe Asp Ile Trp Leu His Val Asp Ala
        275                 280                 285

Ala Tyr Gly Gly Ser Ala Cys Ile Cys Pro Glu Phe Arg Gln Tyr Leu
    290                 295                 300

Asp Gly Ile Glu Arg Ala Asn Ser Phe Ser Leu Ser Pro His Lys Trp
305                 310                 315                 320

Leu Leu Ser Tyr Leu Asp Cys Cys Cys Met Trp Val Lys Glu Pro Ser
                325                 330                 335

Val Leu Val Lys Ala Leu Ser Thr Asn Pro Glu Tyr Leu Arg Asn Lys
            340                 345                 350

Arg Ser Glu His Gly Ser Val Val Asp Tyr Lys Asp Trp Gln Ile Gly
        355                 360                 365

Thr Gly Arg Lys Phe Lys Ser Leu Arg Leu Trp Leu Ile Met Arg Ser
    370                 375                 380

Tyr Gly Val Ala Asn Leu Gln Ser His Ile Arg Ser Asp Val Arg Met
385                 390                 395                 400

Ala Lys Met Phe Glu Gly Leu Val Arg Ser Asp Pro Tyr Phe Glu Val
                405                 410                 415

Ile Val Pro Arg Arg Phe Ser Leu Val Cys Phe Arg Phe Asn Pro Asp
            420                 425                 430

Lys Glu Tyr Glu Pro Ala Tyr Thr Glu Leu Leu Asn Lys Arg Leu Leu
        435                 440                 445

Asp Asn Val Asn Ser Thr Gly Arg Val Tyr Met Thr His Thr Val Ala
    450                 455                 460

Gly Gly Ile Tyr Met Leu Arg Phe Ala Val Gly Ala Thr Phe Thr Glu
465                 470                 475                 480

Asp Arg His Leu Ile Cys Ala Trp Lys Leu Ile Lys Asp Cys Ala Asp
                485                 490                 495

Ala Leu Leu Arg Asn Cys Gln
            500

<210> SEQ ID NO 33
<211> LENGTH: 281
<212> TYPE: PRT
<213> ORGANISM: Drosophila caribiana
<220> FEATURE:
<221> NAME/KEY: misc_feature
<222> LOCATION: (79)..(79)
<223> OTHER INFORMATION: Xaa can be any naturally occurring amino acid

<400> SEQUENCE: 33

Met Leu Asp Leu Pro Ala Glu Phe Leu Ala Cys Ser Gly Gly Lys Gly
1               5                   10                  15

Gly Gly Val Ile Gln Gly Thr Ala Ser Glu Ser Thr Leu Val Ala Leu
            20                  25                  30

Leu Gly Ala Lys Ala Lys Lys Leu Gln Glu Val Lys Ala Glu His Pro
        35                  40                  45
```

Glu Trp Asp Asp His Thr Ile Ile Gly Lys Leu Val Gly Tyr Thr Ser
    50                  55                  60

Ala Gln Ser His Ser Ser Val Glu Arg Ala Gly Leu Leu Gly Xaa Ile
65                  70                  75                  80

Lys Leu Arg Ser Val Pro Ala Asp Glu His Asn Arg Leu Arg Gly Asp
                85                  90                  95

Ala Leu Glu Lys Ala Ile Glu Lys Asp Leu Ala Glu Gly Leu Ile Pro
            100                 105                 110

Phe Tyr Ala Val Val Thr Leu Gly Thr Thr Asn Ser Cys Ala Phe Asp
        115                 120                 125

Arg Leu Asp Glu Cys Gly Pro Val Ala Asn Lys His Lys Val Trp Val
130                 135                 140

His Val Asp Ala Ala Tyr Ala Gly Ser Ala Phe Ile Cys Pro Glu Tyr
145                 150                 155                 160

Arg His His Met Lys Gly Ile Glu Thr Ala Asp Ser Phe Asn Phe Asn
                165                 170                 175

Pro His Lys Trp Met Leu Val Asn Phe Asp Cys Ser Ala Met Trp Leu
            180                 185                 190

Lys Asp Pro Ser Trp Val Val Asn Ala Phe Asn Val Asp Pro Leu Tyr
        195                 200                 205

Leu Lys His Asp Met Gln Gly Ser Ala Pro Asp Tyr Arg His Trp Gln
210                 215                 220

Ile Pro Leu Gly Arg Arg Phe Arg Ala Leu Lys Leu Trp Phe Val Leu
225                 230                 235                 240

Arg Leu Tyr Gly Val Glu Asn Leu Gln Ala His Ile Arg Arg His Cys
                245                 250                 255

Gly Phe Ala Gln Gln Phe Ala Asp Leu Cys Val Ala Asp Glu Arg Phe
            260                 265                 270

Glu Leu Ala Ala Glu Val Asn Met Gly
        275                 280

<210> SEQ ID NO 34
<211> LENGTH: 478
<212> TYPE: PRT
<213> ORGANISM: Maricaulis maris

<400> SEQUENCE: 34

Met His Gly Arg Cys Lys Lys Leu Arg Leu Pro Pro Gly Met Ile Met
1               5                   10                  15

Lys Leu Glu Glu Phe Gly Leu Trp Ser Arg Arg Ile Ala Asp Trp Ser
            20                  25                  30

Lys Thr Tyr Leu Glu Thr Leu Arg Glu Arg Pro Val Arg Pro Ala Thr
        35                  40                  45

Arg Pro Ala Asp Val Leu Asn Ala Leu Pro Val Thr Pro Pro Glu Asp
    50                  55                  60

Ala Thr Asp Met Ala Glu Ile Phe Ala Asp Phe Glu Arg Ile Val Pro
65                  70                  75                  80

Asp Ala Met Thr His Trp Gln His Pro Arg Phe Phe Ala Tyr Phe Pro
                85                  90                  95

Ala Asn Ala Ala Pro Ala Ser Ile Leu Ala Glu Gln Leu Val Ser Thr
            100                 105                 110

Met Ala Ala Gln Cys Met Leu Trp Gln Thr Ser Pro Ala Ala Thr Glu
        115                 120                 125

Met Glu Thr Arg Met Val Asp Trp Leu Arg Gln Ala Leu Gly Leu Pro

```
                    130                 135                 140
Asp Gly Trp Arg Gly Val Ile Gln Asp Ser Ala Ser Ala Thr Leu
145                 150                 155                 160

Ser Ala Val Met Thr Met Arg Glu Arg Ala Leu Asp Trp Arg Gly Ile
                165                 170                 175

Arg Ser Gly Leu Ala Gly Glu Lys Ala Pro Arg Ile Tyr Ala Ser Ala
            180                 185                 190

Gln Thr His Ser Ser Val Asp Lys Ala Cys Trp Val Ala Gly Ile Gly
        195                 200                 205

Gln Asp Asn Leu Val Lys Ile Ala Thr Thr Asp Asp Tyr Gly Met Asp
    210                 215                 220

Pro Asp Ala Leu Arg Ala Ala Ile Arg Ala Asp Arg Ala Ala Gly His
225                 230                 235                 240

Leu Pro Ala Gly Ile Val Ile Cys Val Gly Thr Ala Ile Gly Ala
                245                 250                 255

Ser Asp Pro Val Ala Ala Ile Ile Glu Val Ala Arg Ala Glu Gly Leu
            260                 265                 270

Tyr Thr His Ile Asp Ala Ala Trp Ala Gly Ser Ala Met Ile Cys Pro
        275                 280                 285

Glu Leu Arg His Ile Trp Glu Gly Ala Glu Gly Ala Asp Ser Ile Val
    290                 295                 300

Phe Asn Pro His Lys Trp Leu Gly Ala Gln Phe Asp Cys Ser Val Gln
305                 310                 315                 320

Phe Leu Arg Asp Pro Thr Asp Gln Leu Lys Ser Leu Thr Leu Arg Pro
                325                 330                 335

Asp Tyr Leu Glu Thr Pro Gly Met Asp Asp Ala Val Asn Tyr Ser Glu
            340                 345                 350

Trp Thr Ile Pro Leu Gly Arg Arg Phe Arg Ala Leu Lys Leu Trp Phe
        355                 360                 365

Leu Ile Arg Ala Tyr Gly Leu Glu Gly Leu Arg Thr Arg Ile Arg Asn
    370                 375                 380

His Ile Ala Trp Ser Asn Glu Ala Cys Glu Ala Ile Arg Asp Leu Pro
385                 390                 395                 400

Gly Leu Glu Ile Val Thr Glu Pro Arg Phe Ser Leu Phe Ser Phe Ala
                405                 410                 415

Cys Thr Ala Gly Asp Glu Ala Thr Ala Asp Leu Leu Glu Arg Ile Asn
            420                 425                 430

Ser Asp Gly Arg Thr Tyr Leu Thr Gln Thr Arg His Glu Gly Arg Tyr
        435                 440                 445

Val Ile Arg Leu Gln Val Gly Gln Phe Asp Cys Thr Arg Ala Asp Val
    450                 455                 460

Met Glu Ala Val Ala Val Ile Gly Glu Leu Arg Gly Glu Gly
465                 470                 475

<210> SEQ ID NO 35
<211> LENGTH: 523
<212> TYPE: PRT
<213> ORGANISM: Oryza sativa

<400> SEQUENCE: 35

Met Gly Ser Leu Asp Ala Asn Pro Ala Ala Tyr Ala Ala Phe Ala
1               5                   10                  15

Ala Asp Val Glu Pro Phe Arg Pro Leu Asp Ala Asp Val Arg Ser
            20                  25                  30
```

-continued

Tyr Leu His Lys Ala Val Asp Phe Val Tyr Asp Tyr Lys Ser Val
            35                  40                  45

Glu Ser Leu Pro Val Leu Pro Gly Val Glu Pro Gly Tyr Leu Leu Arg
 50                  55                  60

Leu Leu Gln Ser Ala Pro Pro Ser Ser Ser Ala Pro Phe Asp Ile Ala
 65                  70                  75                  80

Met Lys Glu Leu Arg Glu Ala Val Val Pro Gly Met Thr His Trp Ala
                85                  90                  95

Ser Pro Asn Phe Phe Ala Phe Phe Pro Ala Thr Asn Ser Ala Ala Ala
                    100                 105                 110

Ile Ala Gly Glu Leu Ile Ala Ser Ala Met Asn Thr Val Gly Phe Thr
                115                 120                 125

Trp Gln Ala Ala Pro Ala Ala Thr Glu Leu Glu Val Leu Ala Leu Asp
    130                 135                 140

Trp Leu Ala Gln Leu Leu Gly Leu Pro Ala Ser Phe Met Asn Arg Thr
145                 150                 155                 160

Val Ala Gly Gly Arg Gly Thr Gly Gly Val Ile Leu Gly Thr Thr
                165                 170                 175

Ser Glu Ala Met Leu Val Thr Leu Val Ala Ala Arg Asp Ala Ala Leu
                180                 185                 190

Arg Arg Ser Gly Ser Asn Gly Val Ala Gly Ile Thr Arg Leu Thr Val
    195                 200                 205

Tyr Ala Ala Asp Gln Thr His Ser Thr Phe Phe Lys Ala Cys Arg Leu
            210                 215                 220

Ala Gly Phe Asp Pro Ala Asn Ile Arg Ser Ile Pro Thr Gly Ala Glu
225                 230                 235                 240

Thr Asp Tyr Gly Leu Asp Pro Ala Arg Leu Leu Glu Ala Met Gln Ala
                245                 250                 255

Asp Ala Asp Ala Gly Leu Val Pro Thr Tyr Val Cys Ala Thr Val Gly
                260                 265                 270

Thr Thr Ser Ser Asn Ala Val Asp Pro Val Gly Ala Val Ala Asp Val
            275                 280                 285

Ala Ala Arg Phe Ala Ala Trp Val His Val Asp Ala Ala Tyr Ala Gly
    290                 295                 300

Ser Ala Cys Ile Cys Pro Glu Phe Arg His His Leu Asp Gly Val Glu
305                 310                 315                 320

Arg Val Asp Ser Ile Ser Met Ser Pro His Lys Trp Leu Met Thr Cys
                325                 330                 335

Leu Asp Cys Thr Cys Leu Tyr Val Arg Asp Thr His Arg Leu Thr Gly
                340                 345                 350

Ser Leu Glu Thr Asn Pro Glu Tyr Leu Lys Asn His Ala Ser Asp Ser
            355                 360                 365

Gly Glu Val Thr Asp Leu Lys Asp Met Gln Val Gly Val Gly Arg Arg
            370                 375                 380

Phe Arg Gly Leu Lys Leu Trp Met Val Met Arg Thr Tyr Gly Ala Gly
385                 390                 395                 400

Lys Leu Gln Glu His Ile Arg Ser Asp Val Ala Met Ala Lys Thr Phe
                405                 410                 415

Glu Asp Leu Val Arg Gly Asp Asp Arg Phe Glu Val Val Pro Arg
                420                 425                 430

Asn Phe Ala Leu Val Cys Phe Arg Ile Arg Pro Arg Lys Ser Gly Ala
            435                 440                 445

Ala Ile Ala Ala Gly Glu Ala Glu Ala Glu Lys Ala Asn Arg Glu Leu

```
                    450                 455                 460
Met Glu Arg Leu Asn Lys Thr Gly Lys Ala Tyr Val Ala His Thr Val
465                 470                 475                 480

Val Gly Gly Arg Phe Val Leu Arg Phe Ala Val Gly Ser Ser Leu Gln
                    485                 490                 495

Glu Glu Arg His Val Arg Ser Ala Trp Glu Leu Ile Lys Lys Thr Thr
                500                 505                 510

Thr Glu Ile Val Ala Asp Ala Gly Glu Asp Lys
            515                 520

<210> SEQ ID NO 36
<211> LENGTH: 470
<212> TYPE: PRT
<213> ORGANISM: Pseudomonas putida

<400> SEQUENCE: 36

Met Thr Pro Glu Gln Phe Arg Gln Tyr Gly His Gln Leu Ile Asp Leu
1               5                   10                  15

Ile Ala Asp Tyr Arg Gln Thr Val Gly Glu Arg Pro Val Met Ala Gln
                20                  25                  30

Val Glu Pro Gly Tyr Leu Lys Ala Ala Leu Pro Ala Gln Ala Pro Arg
            35                  40                  45

Gln Gly Glu Pro Phe Ala Ala Ile Leu Asp Asp Val Asn Gln Leu Val
        50                  55                  60

Met Pro Gly Leu Ser His Trp Gln His Pro Asp Phe Tyr Gly Tyr Phe
65              70                  75                  80

Pro Ser Asn Gly Thr Leu Ser Ser Val Leu Gly Asp Phe Leu Ser Thr
                85                  90                  95

Gly Leu Gly Val Leu Gly Leu Ser Trp Gln Ser Ser Pro Ala Leu Ser
            100                 105                 110

Glu Leu Glu Glu Thr Thr Leu Asp Trp Leu Arg Gln Leu Leu Gly Leu
        115                 120                 125

Ser Gly Gln Trp Ser Gly Val Ile Gln Asp Thr Ala Ser Thr Ser Thr
    130                 135                 140

Leu Val Ala Leu Ile Cys Ala Arg Glu Arg Ala Ser Asp Tyr Ala Leu
145                 150                 155                 160

Val Arg Gly Gly Leu Gln Ala Gln Ala Lys Pro Leu Ile Val Tyr Val
                165                 170                 175

Ser Ala His Ala His Ser Ser Val Asp Lys Ala Ala Leu Leu Ala Gly
            180                 185                 190

Phe Gly Arg Asp Asn Ile Arg Leu Ile Pro Thr Asp Glu Arg Tyr Ala
        195                 200                 205

Leu Arg Pro Glu Ala Leu Gln Val Ala Ile Glu Gln Asp Leu Ala Ala
    210                 215                 220

Gly Asn Gln Pro Cys Ala Val Val Ala Thr Thr Gly Thr Thr Ala Thr
225                 230                 235                 240

Thr Ala Leu Asp Pro Leu Arg Pro Ile Gly Glu Ile Ala Gln Ala His
                245                 250                 255

Gly Leu Trp Leu His Val Asp Ser Ala Met Ala Gly Ser Ala Met Ile
            260                 265                 270

Leu Pro Glu Cys Arg Trp Met Trp Asp Gly Ile Glu Leu Ala Asp Ser
        275                 280                 285

Leu Val Val Asn Ala His Lys Trp Leu Gly Val Ala Phe Asp Cys Ser
    290                 295                 300
```

-continued

```
Ile Tyr Tyr Val Arg Asp Pro Gln His Leu Ile Arg Val Met Ser Thr
305                 310                 315                 320

Asn Pro Ser Tyr Leu Gln Ser Ser Val Asp Gly Glu Val Lys Asn Leu
            325                 330                 335

Arg Asp Trp Gly Ile Pro Leu Gly Arg Arg Phe Arg Ala Leu Lys Leu
            340                 345                 350

Trp Phe Met Leu Arg Ser Glu Gly Val Glu Ala Leu Gln Ala Arg Leu
        355                 360                 365

Arg Arg Asp Leu Asp Asn Ala Gln Trp Leu Ala Gly Gln Ile Gly Ala
370                 375                 380

Ala Ala Glu Trp Glu Val Leu Ala Pro Val Gln Leu Gln Thr Leu Cys
385                 390                 395                 400

Ile Arg His Arg Pro Ala Gly Leu Glu Gly Glu Ala Leu Asp Ala His
                405                 410                 415

Thr Lys Gly Trp Ala Glu Arg Leu Asn Ala Ser Gly Asp Ala Tyr Val
            420                 425                 430

Thr Pro Ala Thr Leu Asp Gly Arg Trp Met Val Arg Val Ser Ile Gly
        435                 440                 445

Ala Leu Pro Thr Glu Arg Glu His Val Glu Gln Leu Trp Ala Arg Leu
450                 455                 460

Gln Glu Val Val Lys Gly
465                 470

<210> SEQ ID NO 37
<211> LENGTH: 500
<212> TYPE: PRT
<213> ORGANISM: Catharanthus roseus

<400> SEQUENCE: 37

Met Gly Ser Ile Asp Ser Thr Asn Val Ala Met Ser Asn Ser Pro Val
1               5                   10                  15

Gly Glu Phe Lys Pro Leu Glu Ala Glu Phe Arg Lys Gln Ala His
            20                  25                  30

Arg Met Val Asp Phe Ile Ala Asp Tyr Tyr Lys Asn Val Glu Thr Tyr
        35                  40                  45

Pro Val Leu Ser Glu Val Glu Pro Gly Tyr Leu Arg Lys Arg Ile Pro
    50                  55                  60

Glu Thr Ala Pro Tyr Leu Pro Glu Pro Leu Asp Asp Ile Met Lys Asp
65                  70                  75                  80

Ile Gln Lys Asp Ile Ile Pro Gly Met Thr Asn Trp Met Ser Pro Asn
            85                  90                  95

Phe Tyr Ala Phe Phe Pro Ala Thr Val Ser Ser Ala Ala Phe Leu Gly
            100                 105                 110

Glu Met Leu Ser Thr Ala Leu Asn Ser Val Gly Phe Thr Trp Val Ser
        115                 120                 125

Ser Pro Ala Ala Thr Glu Leu Glu Met Ile Val Met Asp Trp Leu Ala
    130                 135                 140

Gln Ile Leu Lys Leu Pro Lys Ser Phe Met Phe Ser Gly Thr Gly Gly
145                 150                 155                 160

Gly Val Ile Gln Asn Thr Thr Ser Glu Ser Ile Leu Cys Thr Ile Ile
            165                 170                 175

Ala Ala Arg Glu Arg Ala Leu Glu Lys Leu Gly Pro Asp Ser Ile
        180                 185                 190

Lys Leu Val Cys Tyr Gly Ser Asp Gln Thr His Thr Met Phe Pro Lys
    195                 200                 205
```

```
Thr Cys Lys Leu Ala Gly Ile Tyr Pro Asn Asn Ile Arg Leu Ile Pro
    210                 215                 220

Thr Thr Val Glu Thr Asp Phe Gly Ile Ser Pro Gln Val Leu Arg Lys
225                 230                 235                 240

Met Val Glu Asp Val Ala Ala Gly Tyr Val Pro Leu Phe Leu Cys
                245                 250                 255

Ala Thr Leu Gly Thr Thr Ser Thr Thr Ala Thr Asp Pro Val Asp Ser
                260                 265                 270

Leu Ser Glu Ile Ala Asn Glu Phe Gly Ile Trp Ile His Val Asp Ala
            275                 280                 285

Ala Tyr Ala Gly Ser Ala Cys Ile Cys Pro Glu Phe Arg His Tyr Leu
        290                 295                 300

Asp Gly Ile Glu Arg Val Asp Ser Leu Ser Leu Ser Pro His Lys Trp
305                 310                 315                 320

Leu Leu Ala Tyr Leu Asp Cys Thr Cys Leu Trp Val Lys Gln Pro His
                325                 330                 335

Leu Leu Leu Arg Ala Leu Thr Thr Asn Pro Glu Tyr Leu Lys Asn Lys
                340                 345                 350

Gln Ser Asp Leu Asp Lys Val Val Asp Phe Lys Asn Trp Gln Ile Ala
            355                 360                 365

Thr Gly Arg Lys Phe Arg Ser Leu Lys Leu Trp Leu Ile Leu Arg Ser
    370                 375                 380

Tyr Gly Val Val Asn Leu Gln Ser His Ile Arg Ser Asp Val Ala Met
385                 390                 395                 400

Gly Lys Met Phe Glu Glu Trp Val Arg Ser Asp Ser Arg Phe Glu Ile
                405                 410                 415

Val Val Pro Arg Asn Phe Ser Leu Val Cys Phe Arg Leu Lys Pro Asp
                420                 425                 430

Val Ser Ser Leu His Val Glu Glu Val Asn Lys Lys Leu Leu Asp Met
            435                 440                 445

Leu Asn Ser Thr Gly Arg Val Tyr Met Thr His Thr Ile Val Gly Gly
        450                 455                 460

Ile Tyr Met Leu Arg Leu Ala Val Gly Ser Ser Leu Thr Glu Glu His
465                 470                 475                 480

His Val Arg Arg Val Trp Asp Leu Ile Gln Lys Leu Thr Asp Asp Leu
                485                 490                 495

Leu Lys Glu Ala
            500

<210> SEQ ID NO 38
<211> LENGTH: 191
<212> TYPE: PRT
<213> ORGANISM: Chlamydomonas reinhardtii

<400> SEQUENCE: 38

Met Ala Glu Glu Ser Leu Asp Ala Ser Val Gln Pro Leu Gly Ser Thr
1               5                   10                  15

Val Phe Phe Gly Pro Val Gln Pro Glu Met Leu Asp Arg Ile His Glu
            20                  25                  30

Leu Glu Ala Ala Ser Tyr Pro Glu Asp Glu Ala Ala Thr Tyr Glu Lys
        35                  40                  45

Leu Lys Phe Arg Ile Glu Asn Ala Ser Asn Val Phe Leu Val Ala Leu
    50                  55                  60

Ser Ala Glu Gly Asp Gly Glu Pro Lys Val Val Gly Phe Val Cys Gly
```

```
            65                  70                  75                  80
Thr Gln Thr Arg Ala Ser Lys Leu Thr His Glu Ser Met Ser Thr His
                85                  90                  95

Asp Ala Asp Gly Ala Leu Leu Cys Ile His Ser Val Val Asp Ala
                100                 105                 110

Ala Leu Arg Arg Arg Gly Leu Ala Thr Arg Met Leu Arg Ala Tyr Thr
                115                 120                 125

Ala Phe Val Ala Ala Thr Ser Pro Gly Leu Thr Gly Ile Arg Leu Leu
            130                 135                 140

Thr Lys Gln Asn Leu Ile Pro Leu Tyr Glu Gly Ala Gly Phe Thr Leu
145                 150                 155                 160

Leu Gly Pro Ser Asp Val Glu His Gly Ala Asp Leu Trp Tyr Glu Cys
                165                 170                 175

Ala Met Glu Leu Glu Ala Glu Glu Ala Glu Ala Glu Ala
            180                 185                 190
```

<210> SEQ ID NO 39
<211> LENGTH: 207
<212> TYPE: PRT
<213> ORGANISM: Bos taurus

<400> SEQUENCE: 39

```
Met Ser Thr Pro Ser Ile His Cys Leu Lys Pro Ser Pro Leu His Leu
1               5                   10                  15

Pro Ser Gly Ile Pro Gly Ser Pro Gly Arg Gln Arg Arg His Thr Leu
                20                  25                  30

Pro Ala Asn Glu Phe Arg Cys Leu Thr Pro Glu Asp Ala Ala Gly Val
            35                  40                  45

Phe Glu Ile Glu Arg Glu Ala Phe Ile Ser Val Ser Gly Asn Cys Pro
        50                  55                  60

Leu Asn Leu Asp Glu Val Arg His Phe Leu Thr Leu Cys Pro Glu Leu
65                  70                  75                  80

Ser Leu Gly Trp Phe Val Glu Gly Arg Leu Val Ala Phe Ile Ile Gly
                85                  90                  95

Ser Leu Trp Asp Glu Glu Arg Leu Thr Gln Glu Ser Leu Thr Leu His
                100                 105                 110

Arg Pro Gly Gly Arg Thr Ala His Leu His Ala Leu Ala Val His His
                115                 120                 125

Ser Phe Arg Gln Gln Gly Lys Gly Ser Val Leu Leu Trp Arg Tyr Leu
            130                 135                 140

Gln His Ala Gly Gly Gln Pro Ala Val Arg Arg Ala Val Leu Met Cys
145                 150                 155                 160

Glu Asp Ala Leu Val Pro Phe Tyr Gln Arg Phe Gly Phe His Pro Ala
                165                 170                 175

Gly Pro Cys Ala Val Val Val Gly Ser Leu Thr Phe Thr Glu Met His
                180                 185                 190

Cys Ser Leu Arg Gly His Ala Ala Leu Arg Arg Asn Ser Asp Arg
                195                 200                 205
```

<210> SEQ ID NO 40
<211> LENGTH: 207
<212> TYPE: PRT
<213> ORGANISM: Bos taurus

<400> SEQUENCE: 40

Met Ser Thr Pro Ser Ile His Cys Leu Lys Pro Ser Pro Leu His Leu

```
              1               5              10              15
        Pro Ser Gly Ile Pro Gly Ser Pro Gly Arg Gln Arg Arg His Thr Leu
                         20                  25                  30

Pro Ala Asn Glu Phe Arg Cys Leu Thr Pro Glu Asp Ala Ala Gly Val
                         35                  40                  45

Phe Glu Ile Glu Arg Glu Pro Phe Ile Ser Val Ser Gly Asn Cys Pro
                         50                  55                  60

Leu Asn Leu Asp Glu Val Arg His Phe Leu Thr Leu Cys Pro Glu Leu
        65                   70                  75                  80

Ser Leu Gly Trp Phe Val Glu Gly Arg Leu Val Ala Phe Ile Ile Gly
                             85                  90                  95

Ser Leu Trp Asp Glu Glu Arg Leu Thr Gln Glu Ser Leu Thr Leu His
                            100                 105                 110

Arg Pro Gly Gly Arg Thr Ala His Leu His Ala Leu Ala Val His His
                            115                 120                 125

Ser Phe Arg Gln Gln Gly Lys Gly Ser Val Leu Leu Trp Arg Tyr Leu
                    130                 135                 140

Gln His Ala Gly Gly Gln Pro Ala Val Arg Arg Ala Val Leu Met Cys
        145                 150                 155                 160

Glu Asp Ala Leu Val Pro Phe Tyr Gln Arg Phe Gly Phe His Pro Ala
                            165                 170                 175

Gly Pro Cys Ala Val Val Gly Ser Leu Thr Phe Thr Glu Met His
                    180                 185                 190

Cys Ser Leu Arg Gly His Ala Ala Leu Arg Arg Asn Ser Asp Arg
                    195                 200                 205

<210> SEQ ID NO 41
<211> LENGTH: 205
<212> TYPE: PRT
<213> ORGANISM: Gallus gallus

<400> SEQUENCE: 41

Met Pro Val Leu Gly Ala Val Pro Phe Leu Lys Pro Thr Pro Leu Gln
        1               5                  10                  15

Gly Pro Arg Asn Ser Pro Gly Arg Gln Arg Arg His Thr Leu Pro Ala
                         20                  25                  30

Ser Glu Phe Arg Cys Leu Ser Pro Glu Asp Ala Val Ser Val Phe Glu
                         35                  40                  45

Ile Glu Arg Glu Ala Phe Ile Ser Val Ser Gly Asp Cys Pro Leu His
                         50                  55                  60

Leu Asp Glu Ile Arg His Phe Leu Thr Leu Cys Pro Glu Leu Ser Leu
        65                   70                  75                  80

Gly Trp Phe Glu Glu Gly Arg Leu Val Ala Phe Ile Ile Gly Ser Leu
                             85                  90                  95

Trp Asp Gln Asp Arg Leu Ser Gln Ala Ala Leu Thr Leu His Asn Pro
                            100                 105                 110

Arg Gly Thr Ala Val His Ile His Val Leu Ala Val His Arg Thr Phe
                            115                 120                 125

Arg Gln Gln Gly Lys Gly Ser Ile Leu Met Trp Arg Tyr Leu Gln Tyr
                    130                 135                 140

Leu Arg Cys Leu Pro Cys Ala Arg Arg Ala Val Leu Met Cys Glu Asp
        145                 150                 155                 160

Phe Leu Val Pro Phe Tyr Glu Lys Cys Gly Phe Val Ala Val Gly Pro
                            165                 170                 175
```

Cys Gln Val Thr Val Gly Thr Leu Ala Phe Thr Glu Met Gln His Glu
                180                 185                 190

Val Arg Gly His Ala Phe Met Arg Arg Asn Ser Gly Cys
            195                 200                 205

<210> SEQ ID NO 42
<211> LENGTH: 207
<212> TYPE: PRT
<213> ORGANISM: Homo sapiens

<400> SEQUENCE: 42

Met Ser Thr Gln Ser Thr His Pro Leu Lys Pro Glu Ala Pro Arg Leu
1               5                   10                  15

Pro Pro Gly Ile Pro Glu Ser Pro Ser Cys Gln Arg Arg His Thr Leu
            20                  25                  30

Pro Ala Ser Glu Phe Arg Cys Leu Thr Pro Glu Asp Ala Val Ser Ala
        35                  40                  45

Phe Glu Ile Glu Arg Glu Ala Phe Ile Ser Val Leu Gly Val Cys Pro
    50                  55                  60

Leu Tyr Leu Asp Glu Ile Arg His Phe Leu Thr Leu Cys Pro Glu Leu
65                  70                  75                  80

Ser Leu Gly Trp Phe Glu Glu Gly Cys Leu Val Ala Phe Ile Ile Gly
                85                  90                  95

Ser Leu Trp Asp Lys Glu Arg Leu Met Gln Glu Ser Leu Thr Leu His
            100                 105                 110

Arg Ser Gly Gly His Ile Ala His Leu His Val Leu Ala Val His Arg
        115                 120                 125

Ala Phe Arg Gln Gln Gly Arg Gly Pro Ile Leu Leu Trp Arg Tyr Leu
    130                 135                 140

His His Leu Gly Ser Gln Pro Ala Val Arg Arg Ala Ala Leu Met Cys
145                 150                 155                 160

Glu Asp Ala Leu Val Pro Phe Tyr Glu Arg Phe Ser Phe His Ala Val
                165                 170                 175

Gly Pro Cys Ala Ile Thr Val Gly Ser Leu Thr Phe Met Glu Leu His
            180                 185                 190

Cys Ser Leu Arg Gly His Pro Phe Leu Arg Arg Asn Ser Gly Cys
        195                 200                 205

<210> SEQ ID NO 43
<211> LENGTH: 205
<212> TYPE: PRT
<213> ORGANISM: Mus musculus

<400> SEQUENCE: 43

Met Leu Asn Ile Asn Ser Leu Lys Pro Glu Ala Leu His Leu Pro Leu
1               5                   10                  15

Gly Thr Ser Glu Phe Leu Gly Cys Gln Arg Arg His Thr Leu Pro Ala
            20                  25                  30

Ser Glu Phe Arg Cys Leu Thr Pro Glu Asp Ala Thr Ser Ala Phe Glu
        35                  40                  45

Ile Glu Arg Glu Ala Phe Ile Ser Val Ser Gly Thr Cys Pro Leu Tyr
    50                  55                  60

Leu Asp Glu Ile Arg His Phe Leu Thr Leu Cys Pro Glu Leu Ser Leu
65                  70                  75                  80

Gly Trp Phe Glu Glu Gly Cys Leu Val Ala Phe Ile Ile Gly Ser Leu
                85                  90                  95

```
Trp Asp Lys Glu Arg Leu Thr Gln Glu Ser Leu Thr Leu His Arg Pro
            100                 105                 110

Gly Gly Arg Thr Ala His Leu His Val Leu Ala Val His Arg Thr Phe
            115                 120                 125

Arg Gln Gln Gly Lys Gly Ser Val Leu Leu Trp Arg Tyr Leu His His
        130                 135                 140

Leu Gly Ser Gln Pro Ala Val Arg Arg Ala Val Leu Met Cys Glu Asp
145                 150                 155                 160

Ala Leu Val Pro Phe Tyr Glu Lys Phe Gly Phe Gln Ala Val Gly Pro
                    165                 170                 175

Cys Ala Ile Thr Val Gly Ser Leu Thr Phe Thr Glu Leu Gln Cys Ser
                180                 185                 190

Leu Arg Cys His Ala Phe Leu Arg Arg Asn Ser Gly Cys
            195                 200                 205

<210> SEQ ID NO 44
<211> LENGTH: 207
<212> TYPE: PRT
<213> ORGANISM: Oryctolagus cuniculus

<400> SEQUENCE: 44

Met Ser Thr Leu Ser Thr Gln Pro Leu Lys Pro Lys Ala Leu His Pro
1               5                   10                  15

Pro Pro Gly Ser Pro Glu Ser Pro Gly His Gln Arg Arg His Thr Leu
            20                  25                  30

Pro Ala Ser Glu Phe Arg Cys Leu Thr Pro Glu Asp Ala Ala Gly Val
        35                  40                  45

Phe Glu Ile Glu Arg Glu Ala Phe Met Ser Val Ser Gly Ser Cys Pro
50                  55                  60

Leu Tyr Leu Asp Glu Ile Arg His Phe Leu Thr Leu Cys Pro Glu Leu
65                  70                  75                  80

Ser Leu Gly Trp Phe Gln Glu Gly Arg Leu Val Ala Phe Ile Ile Gly
                85                  90                  95

Ser Leu Trp Asp Lys Glu Arg Leu Thr Gln Glu Ser Leu Thr Leu His
            100                 105                 110

Arg Pro Gly Gly Arg Val Ala His Leu His Val Leu Ala Val His Arg
        115                 120                 125

Ala Cys Arg Gln Gln Gly Lys Gly Ser Val Leu Leu Trp Arg Tyr Leu
    130                 135                 140

Gln His Leu Gly Gly Gln Arg Ala Val Arg Arg Ala Val Leu Met Cys
145                 150                 155                 160

Glu Asp Ala Leu Val Pro Phe Tyr Glu Arg Leu Gly Phe Arg Ala Val
                165                 170                 175

Gly Pro Cys Ala Val Thr Val Gly Ser Leu Ala Phe Thr Glu Leu Gln
                180                 185                 190

Cys Ser Val Arg Gly His Ala Cys Leu Arg Arg Lys Ser Gly Cys
            195                 200                 205

<210> SEQ ID NO 45
<211> LENGTH: 207
<212> TYPE: PRT
<213> ORGANISM: Ovis aries

<400> SEQUENCE: 45

Met Ser Thr Pro Ser Val His Cys Leu Lys Pro Ser Pro Leu His Leu
1               5                   10                  15
```

```
Pro Ser Gly Ile Pro Gly Ser Pro Gly Arg Gln Arg Arg His Thr Leu
                20                  25                  30

Pro Ala Asn Glu Phe Arg Cys Leu Thr Pro Glu Asp Ala Ala Gly Val
            35                  40                  45

Phe Glu Ile Glu Arg Glu Ala Phe Ile Ser Val Ser Gly Asn Cys Pro
        50                  55                  60

Leu Asn Leu Asp Glu Val Gln His Phe Leu Thr Leu Cys Pro Glu Leu
 65                  70                  75                  80

Ser Leu Gly Trp Phe Val Glu Gly Arg Leu Val Ala Phe Ile Ile Gly
                85                  90                  95

Ser Leu Trp Asp Glu Glu Arg Leu Thr Gln Glu Ser Leu Ala Leu His
               100                 105                 110

Arg Pro Arg Gly His Ser Ala His Leu His Ala Leu Ala Val His Arg
            115                 120                 125

Ser Phe Arg Gln Gln Gly Lys Gly Ser Val Leu Leu Trp Arg Tyr Leu
        130                 135                 140

His His Val Gly Ala Gln Pro Ala Val Arg Arg Ala Val Leu Met Cys
145                 150                 155                 160

Glu Asp Ala Leu Val Pro Phe Tyr Gln Arg Phe Gly Phe His Pro Ala
                165                 170                 175

Gly Pro Cys Ala Ile Val Val Gly Ser Leu Thr Phe Thr Glu Met His
            180                 185                 190

Cys Ser Leu Arg Gly His Ala Ala Leu Arg Arg Asn Ser Asp Arg
        195                 200                 205

<210> SEQ ID NO 46
<211> LENGTH: 364
<212> TYPE: PRT
<213> ORGANISM: Oryza sativa

<400> SEQUENCE: 46

Met Ala Gln Asn Val Gln Glu Asn Glu Gln Val Met Ser Thr Glu Asp
  1               5                  10                  15

Leu Leu Gln Ala Gln Ile Glu Leu Tyr His His Cys Leu Ala Phe Ile
                 20                  25                  30

Lys Ser Met Ala Leu Arg Ala Ala Thr Asp Leu Arg Ile Pro Asp Ala
             35                  40                  45

Ile His Cys Asn Gly Gly Ala Ala Thr Leu Thr Asp Leu Ala Ala His
         50                  55                  60

Val Gly Leu His Pro Thr Lys Leu Ser His Leu Arg Arg Leu Met Arg
 65                  70                  75                  80

Val Leu Thr Leu Ser Gly Ile Phe Thr Val His Asp Gly Asp Gly Glu
                 85                  90                  95

Ala Thr Tyr Thr Leu Thr Arg Val Ser Arg Leu Leu Leu Ser Asp Gly
            100                 105                 110

Val Glu Arg Thr His Gly Leu Ser Gln Met Val Arg Val Phe Val Asn
        115                 120                 125

Pro Val Ala Val Ala Ser Gln Phe Ser Leu His Glu Trp Phe Thr Val
    130                 135                 140

Glu Lys Ala Ala Ala Val Ser Leu Phe Glu Val Ala His Gly Cys Thr
145                 150                 155                 160

Arg Trp Glu Met Ile Ala Asn Asp Ser Lys Asp Gly Ser Met Phe Asn
                165                 170                 175

Ala Gly Met Val Glu Asp Ser Ser Val Ala Met Asp Ile Ile Leu Arg
            180                 185                 190
```

```
Lys Ser Ser Asn Val Phe Arg Gly Ile Asn Ser Leu Val Asp Val Gly
            195                 200                 205

Gly Gly Tyr Gly Ala Val Ala Ala Ala Val Val Arg Ala Phe Pro Asp
    210                 215                 220

Ile Lys Cys Thr Val Leu Asp Leu Pro His Ile Val Ala Lys Ala Pro
225                 230                 235                 240

Ser Asn Asn Asn Ile Gln Phe Val Gly Gly Asp Leu Phe Glu Phe Ile
                245                 250                 255

Pro Ala Ala Asp Val Val Leu Leu Lys Cys Ile Leu His Cys Trp Gln
                260                 265                 270

His Asp Asp Cys Val Lys Ile Met Arg Arg Cys Lys Glu Ala Ile Ser
            275                 280                 285

Ala Arg Asp Ala Gly Gly Lys Val Ile Leu Ile Glu Val Val Val Gly
        290                 295                 300

Ile Gly Ser Asn Glu Thr Val Pro Lys Glu Met Gln Leu Leu Phe Asp
305                 310                 315                 320

Val Phe Met Met Tyr Thr Asp Gly Ile Glu Arg Glu His Glu Trp
                325                 330                 335

Lys Lys Ile Phe Leu Glu Ala Gly Phe Ser Asp Tyr Lys Ile Ile Pro
                340                 345                 350

Val Leu Gly Val Arg Ser Ile Ile Glu Val Tyr Pro
            355                 360

<210> SEQ ID NO 47
<211> LENGTH: 345
<212> TYPE: PRT
<213> ORGANISM: Homo sapiens

<400> SEQUENCE: 47

Met Gly Ser Ser Glu Asp Gln Ala Tyr Arg Leu Leu Asn Asp Tyr Ala
1               5                   10                  15

Asn Gly Phe Met Val Ser Gln Val Leu Phe Ala Ala Cys Glu Leu Gly
                20                  25                  30

Val Phe Asp Leu Leu Ala Glu Ala Pro Gly Pro Leu Asp Val Ala Ala
            35                  40                  45

Val Ala Ala Gly Val Arg Ala Ser Ala His Gly Thr Glu Leu Leu Leu
    50                  55                  60

Asp Ile Cys Val Ser Leu Lys Leu Leu Lys Val Glu Thr Arg Gly Gly
65                  70                  75                  80

Lys Ala Phe Tyr Arg Asn Thr Glu Leu Ser Ser Asp Tyr Leu Thr Thr
                85                  90                  95

Val Ser Pro Thr Ser Gln Cys Ser Met Leu Lys Tyr Met Gly Arg Thr
            100                 105                 110

Ser Tyr Arg Cys Trp Gly His Leu Ala Asp Ala Val Arg Glu Gly Arg
        115                 120                 125

Asn Gln Tyr Leu Glu Thr Phe Gly Val Pro Ala Glu Glu Leu Phe Thr
    130                 135                 140

Ala Ile Tyr Arg Ser Glu Gly Glu Arg Leu Gln Phe Met Gln Ala Leu
145                 150                 155                 160

Gln Glu Val Trp Ser Val Asn Gly Arg Ser Val Leu Thr Ala Phe Asp
                165                 170                 175

Leu Ser Val Phe Pro Leu Met Cys Asp Leu Gly Gly Gly Ala Gly Ala
            180                 185                 190

Leu Ala Lys Glu Cys Met Ser Leu Tyr Pro Gly Cys Lys Ile Thr Val
```

```
            195                 200                 205
Phe Asp Ile Pro Glu Val Val Trp Thr Ala Lys Gln His Phe Ser Phe
210                 215                 220

Gln Glu Glu Gln Ile Asp Phe Gln Glu Gly Asp Phe Phe Lys Asp
225                 230                 235                 240

Pro Leu Pro Glu Ala Asp Leu Tyr Ile Leu Ala Arg Val Leu His Asp
                245                 250                 255

Trp Ala Asp Gly Lys Cys Ser His Leu Leu Glu Arg Ile Tyr His Thr
                260                 265                 270

Cys Lys Pro Gly Gly Gly Ile Leu Val Ile Glu Ser Leu Leu Asp Glu
                275                 280                 285

Asp Arg Arg Gly Pro Leu Leu Thr Gln Leu Tyr Ser Leu Asn Met Leu
                290                 295                 300

Val Gln Thr Glu Gly Gln Glu Arg Thr Pro Thr His Tyr His Met Leu
305                 310                 315                 320

Leu Ser Ser Ala Gly Phe Arg Asp Phe Gln Phe Lys Lys Thr Gly Ala
                325                 330                 335

Ile Tyr Asp Ala Ile Leu Ala Arg Lys
                340                 345

<210> SEQ ID NO 48
<211> LENGTH: 345
<212> TYPE: PRT
<213> ORGANISM: Bos taurus

<400> SEQUENCE: 48

Met Cys Ser Gln Glu Gly Glu Gly Tyr Ser Leu Leu Lys Glu Tyr Ala
1               5                   10                  15

Asn Gly Phe Met Val Ser Gln Val Leu Phe Ala Ala Cys Glu Leu Gly
                20                  25                  30

Val Phe Glu Leu Leu Ala Glu Ala Leu Glu Pro Leu Asp Ser Ala Ala
                35                  40                  45

Val Ser Ser His Leu Gly Ser Ser Pro Gln Gly Thr Glu Leu Leu Leu
                50                  55                  60

Asn Thr Cys Val Ser Leu Lys Leu Leu Gln Ala Asp Val Arg Gly Gly
65                  70                  75                  80

Lys Ala Val Tyr Ala Asn Thr Glu Leu Ala Ser Thr Tyr Leu Val Arg
                85                  90                  95

Gly Ser Pro Arg Ser Gln Arg Asp Met Leu Leu Tyr Ala Gly Arg Thr
                100                 105                 110

Ala Tyr Val Cys Trp Arg His Leu Ala Glu Ala Val Arg Glu Gly Arg
                115                 120                 125

Asn Gln Tyr Leu Lys Ala Phe Gly Ile Pro Ser Glu Glu Leu Phe Ser
130                 135                 140

Ala Ile Tyr Arg Ser Glu Asp Glu Arg Leu Gln Phe Met Gln Gly Leu
145                 150                 155                 160

Gln Asp Val Trp Arg Leu Glu Gly Ala Thr Val Leu Ala Ala Phe Asp
                165                 170                 175

Leu Ser Pro Phe Pro Leu Ile Cys Asp Leu Gly Gly Gly Ser Gly Ala
                180                 185                 190

Leu Ala Lys Ala Cys Val Ser Leu Tyr Pro Gly Cys Arg Ala Ile Val
                195                 200                 205

Phe Asp Ile Pro Gly Val Val Gln Ile Ala Lys Arg His Phe Ser Ala
210                 215                 220
```

```
Ser Glu Asp Glu Arg Ile Ser Phe His Glu Gly Asp Phe Phe Lys Asp
225                 230                 235                 240

Ala Leu Pro Glu Ala Asp Leu Tyr Ile Leu Ala Arg Val Leu His Asp
            245                 250                 255

Trp Thr Asp Ala Lys Cys Ser His Leu Leu Gln Arg Val Tyr Arg Ala
        260                 265                 270

Cys Arg Thr Gly Gly Ile Leu Val Ile Glu Ser Leu Leu Asp Thr
    275                 280                 285

Asp Gly Arg Gly Pro Leu Thr Thr Leu Leu Tyr Ser Leu Asn Met Leu
290                 295                 300

Val Gln Thr Glu Gly Arg Glu Arg Thr Pro Ala Glu Tyr Arg Ala Leu
305                 310                 315                 320

Leu Gly Pro Ala Gly Phe Arg Asp Val Arg Cys Arg Arg Thr Gly Gly
            325                 330                 335

Thr Tyr Asp Ala Val Leu Ala Arg Lys
        340                 345

<210> SEQ ID NO 49
<211> LENGTH: 432
<212> TYPE: PRT
<213> ORGANISM: Rattus norwegicus

<400> SEQUENCE: 49

Met Ala Pro Gly Arg Glu Gly Glu Leu Asp Arg Asp Phe Arg Val Leu
1               5                   10                  15

Met Ser Leu Ala His Gly Phe Met Val Ser Gln Val Leu Phe Ala Ala
            20                  25                  30

Leu Asp Leu Gly Ile Phe Asp Leu Ala Ala Gln Gly Pro Val Ala Ala
        35                  40                  45

Glu Ala Val Ala Gln Thr Gly Gly Trp Ser Pro Arg Gly Thr Gln Leu
    50                  55                  60

Leu Met Asp Ala Cys Thr Arg Leu Gly Leu Leu Arg Gly Ala Gly Asp
65                  70                  75                  80

Gly Ser Tyr Thr Asn Ser Ala Leu Ser Ser Thr Phe Leu Val Ser Gly
            85                  90                  95

Ser Pro Gln Ser Gln Arg Cys Met Leu Leu Tyr Leu Ala Gly Thr Thr
        100                 105                 110

Tyr Gly Cys Trp Ala His Leu Ala Ala Gly Val Arg Glu Gly Arg Asn
    115                 120                 125

Gln Tyr Ser Arg Ala Val Gly Ile Ser Ala Glu Asp Pro Phe Ser Ala
130                 135                 140

Ile Tyr Arg Ser Glu Pro Glu Arg Leu Leu Phe Met Arg Gly Leu Gln
145                 150                 155                 160

Glu Thr Trp Ser Leu Cys Gly Gly Arg Val Leu Thr Ala Phe Asp Leu
            165                 170                 175

Ser Arg Phe Arg Val Ile Cys Asp Leu Gly Gly Gly Ser Gly Ala Leu
        180                 185                 190

Ala Gln Glu Ala Ala Arg Leu Tyr Pro Gly Ser Ser Val Cys Val Phe
    195                 200                 205

Asp Leu Pro Asp Val Ile Ala Ala Arg Thr His Phe Leu Ser Pro
210                 215                 220

Gly Ala Arg Pro Ser Val Arg Phe Val Ala Gly Asp Phe Phe Arg Ser
225                 230                 235                 240

Arg Leu Pro Arg Ala Asp Leu Phe Ile Leu Ala Arg Val Leu His Asp
            245                 250                 255
```

Trp Ala Asp Gly Ala Cys Val Glu Leu Leu Gly Arg Leu His Arg Ala
            260                 265                 270

Cys Arg Pro Gly Gly Ala Leu Leu Leu Val Glu Ala Val Leu Ala Lys
        275                 280                 285

Gly Gly Ala Gly Pro Leu Arg Ser Leu Leu Ser Leu Asn Met Met
290                 295                 300

Leu Gln Ala Glu Gly Trp Glu Arg Gln Ala Ser Asp Tyr Arg Asn Leu
305                 310                 315                 320

Ala Thr Arg Ala Gly Phe Pro Arg Leu Gln Leu Arg Arg Pro Gly Gly
                325                 330                 335

Pro Tyr His Ala Met Leu Ala Arg Arg Gly Pro Arg Pro Gly Ile Ile
            340                 345                 350

Thr Gly Val Gly Ser Asn Thr Thr Gly Thr Gly Ser Phe Val Thr Gly
                355                 360                 365

Ile Arg Arg Asp Val Pro Gly Ala Arg Ser Asp Ala Ala Gly Thr Gly
370                 375                 380

Ser Gly Thr Gly Asn Thr Gly Ser Gly Ile Met Leu Gln Gly Glu Thr
385                 390                 395                 400

Leu Glu Ser Glu Val Ser Ala Pro Gln Ala Gly Ser Asp Val Gly Gly
                405                 410                 415

Ala Gly Asn Glu Pro Arg Ser Gly Thr Leu Lys Gln Gly Asp Trp Lys
                420                 425                 430

<210> SEQ ID NO 50
<211> LENGTH: 346
<212> TYPE: PRT
<213> ORGANISM: Gallus gallus

<400> SEQUENCE: 50

Met Asp Ser Thr Glu Asp Leu Asp Tyr Pro Gln Ile Ile Phe Gln Tyr
1               5                   10                  15

Ser Asn Gly Phe Leu Val Ser Lys Val Met Phe Thr Ala Cys Glu Leu
            20                  25                  30

Gly Val Phe Asp Leu Leu Leu Gln Ser Gly Arg Pro Leu Ser Leu Asp
        35                  40                  45

Val Ile Ala Ala Arg Leu Gly Thr Ser Ile Met Gly Met Glu Arg Leu
    50                  55                  60

Leu Asp Ala Cys Val Gly Leu Lys Leu Leu Ala Val Glu Leu Arg Arg
65                  70                  75                  80

Glu Gly Ala Phe Tyr Arg Asn Thr Glu Ile Ser Asn Ile Tyr Leu Thr
                85                  90                  95

Lys Ser Ser Pro Lys Ser Gln Tyr His Ile Met Met Tyr Tyr Ser Asn
            100                 105                 110

Thr Val Tyr Leu Cys Trp His Tyr Leu Thr Asp Ala Val Arg Glu Gly
        115                 120                 125

Arg Asn Gln Tyr Glu Arg Ala Phe Gly Ile Ser Ser Lys Asp Leu Phe
    130                 135                 140

Gly Ala Arg Tyr Arg Ser Glu Glu Met Leu Lys Phe Leu Ala Gly
145                 150                 155                 160

Gln Asn Ser Ile Trp Ser Ile Cys Gly Arg Asp Val Leu Thr Ala Phe
                165                 170                 175

Asp Leu Ser Pro Phe Thr Gln Ile Tyr Asp Leu Gly Gly Gly Gly
            180                 185                 190

Ala Leu Ala Gln Glu Cys Val Phe Leu Tyr Pro Asn Cys Thr Val Thr

```
            195                 200                 205
Ile Tyr Asp Leu Pro Lys Val Val Gln Val Ala Lys Glu Arg Leu Val
210                 215                 220

Pro Pro Glu Glu Arg Arg Ile Ala Phe His Glu Gly Asp Phe Phe Lys
225                 230                 235                 240

Asp Ser Ile Pro Glu Ala Asp Leu Tyr Ile Leu Ser Lys Ile Leu His
                    245                 250                 255

Asp Trp Asp Asp Lys Lys Cys Arg Gln Leu Leu Ala Glu Val Tyr Lys
                260                 265                 270

Ala Cys Arg Pro Gly Gly Val Leu Leu Val Glu Ser Leu Leu Ser
            275                 280                 285

Glu Asp Arg Ser Gly Pro Val Glu Thr Gln Leu Tyr Ser Leu Asn Met
290                 295                 300

Leu Val Gln Thr Glu Gly Lys Glu Arg Thr Ala Val Glu Tyr Ser Glu
305                 310                 315                 320

Leu Leu Gly Ala Ala Gly Phe Arg Glu Val Gln Val Arg Arg Thr Gly
                    325                 330                 335

Lys Leu Tyr Asp Ala Val Leu Gly Arg Lys
                340                 345

<210> SEQ ID NO 51
<211> LENGTH: 345
<212> TYPE: PRT
<213> ORGANISM: Macaca mulatta

<400> SEQUENCE: 51

Met Gly Ser Ser Gly Asp Asp Gly Tyr Arg Leu Leu Asn Glu Tyr Thr
1               5                   10                  15

Asn Gly Phe Met Val Ser Gln Val Leu Phe Ala Ala Cys Glu Leu Gly
                20                  25                  30

Val Phe Asp Leu Leu Ala Glu Ala Pro Gly Pro Leu Asp Val Ala Ala
            35                  40                  45

Val Ala Ala Gly Val Glu Ala Ser Ser His Gly Thr Glu Leu Leu Leu
50                  55                  60

Asp Thr Cys Val Ser Leu Lys Leu Leu Lys Val Glu Thr Arg Ala Gly
65                  70                  75                  80

Lys Ala Phe Tyr Gln Asn Thr Glu Leu Ser Ser Ala Tyr Leu Thr Arg
                85                  90                  95

Val Ser Pro Thr Ser Gln Cys Asn Leu Leu Lys Tyr Met Gly Arg Thr
            100                 105                 110

Ser Tyr Gly Cys Trp Gly His Leu Ala Asp Ala Val Arg Glu Gly Lys
        115                 120                 125

Asn Gln Tyr Leu Gln Thr Phe Gly Val Pro Ala Glu Asp Leu Phe Lys
130                 135                 140

Ala Ile Tyr Arg Ser Glu Gly Glu Arg Leu Gln Phe Met Gln Ala Leu
145                 150                 155                 160

Gln Glu Val Trp Ser Val Asn Gly Arg Ser Val Leu Thr Ala Phe Asp
                165                 170                 175

Leu Ser Gly Phe Pro Leu Met Cys Asp Leu Gly Gly Gly Pro Gly Ala
            180                 185                 190

Leu Ala Lys Glu Cys Leu Ser Leu Tyr Pro Gly Cys Lys Val Thr Val
        195                 200                 205

Phe Asp Val Pro Glu Val Val Arg Thr Ala Lys Gln His Phe Ser Phe
210                 215                 220
```

```
Pro Glu Glu Glu Glu Ile His Leu Gln Glu Gly Asp Phe Phe Lys Asp
225                 230                 235                 240

Pro Leu Pro Glu Ala Asp Leu Tyr Ile Leu Ala Arg Ile Leu His Asp
            245                 250                 255

Trp Ala Asp Gly Lys Cys Ser His Leu Leu Glu Arg Val Tyr His Thr
            260                 265                 270

Cys Lys Pro Gly Gly Ile Leu Val Ile Glu Ser Leu Leu Asp Glu
            275                 280                 285

Asp Arg Arg Gly Pro Leu Leu Thr Gln Leu Tyr Ser Leu Asn Met Leu
290                 295                 300

Val Gln Thr Glu Gly Gln Glu Arg Thr Pro Thr His Tyr His Met Leu
305                 310                 315                 320

Leu Ser Ser Ala Gly Phe Arg Asp Phe Gln Phe Lys Lys Thr Gly Ala
            325                 330                 335

Ile Tyr Asp Ala Ile Leu Val Arg Lys
            340                 345

<210> SEQ ID NO 52
<211> LENGTH: 298
<212> TYPE: PRT
<213> ORGANISM: Escherichia coli

<400> SEQUENCE: 52

Met Leu Glu Lys Ser Leu Ala Thr Leu Phe Ala Leu Leu Ile Leu Ala
1               5                   10                  15

Thr Leu Ile Asn Arg Phe Leu Leu Trp Arg Leu Pro Glu Arg Lys Gly
            20                  25                  30

Gly Glu Val Thr Leu Arg Ile Arg Thr Trp Trp Gly Ile Val Ile Cys
        35                  40                  45

Phe Ser Met Val Ile Ser Gly Pro Arg Trp Met Thr Leu Thr Phe Phe
50                  55                  60

Ala Leu Ile Ser Phe Leu Ala Leu Lys Glu Tyr Cys Thr Leu Ile Ser
65                  70                  75                  80

Val His Phe Pro Arg Trp Leu Tyr Trp Gly Ile Pro Leu Asn Tyr Leu
                85                  90                  95

Leu Ile Gly Phe Asn Cys Phe Glu Leu Phe Leu Leu Phe Ile Pro Leu
            100                 105                 110

Ala Gly Phe Leu Ile Leu Ala Thr Gly Gln Val Leu Val Gly Asp Pro
            115                 120                 125

Ser Gly Phe Leu His Thr Val Ser Ala Ile Phe Trp Gly Trp Ile Met
130                 135                 140

Thr Val Phe Ala Leu Ser His Ala Ala Trp Leu Leu Met Leu Pro Thr
145                 150                 155                 160

Thr Asn Ile Gln Gly Gly Ala Leu Leu Val Leu Phe Leu Leu Ala Leu
            165                 170                 175

Thr Glu Ser Asn Asp Ile Ala Gln Tyr Leu Trp Gly Lys Ser Cys Gly
            180                 185                 190

Arg Arg Lys Val Val Pro Lys Val Ser Pro Gly Lys Thr Leu Glu Gly
        195                 200                 205

Leu Met Gly Gly Val Ile Thr Ile Met Ile Ala Ser Leu Ile Ile Gly
        210                 215                 220

Pro Leu Leu Thr Pro Leu Asn Thr Leu Gln Ala Leu Leu Ala Gly Leu
225                 230                 235                 240

Leu Ile Gly Ile Ser Gly Phe Cys Gly Asp Val Val Met Ser Ala Ile
            245                 250                 255
```

```
Lys Arg Asp Ile Gly Val Lys Asp Ser Gly Lys Leu Leu Pro Gly His
            260                 265                 270

Gly Gly Leu Leu Asp Arg Ile Asp Ser Leu Ile Phe Thr Ala Pro Val
            275                 280                 285

Phe Phe Tyr Phe Ile Arg Tyr Cys Cys Tyr
            290                 295

<210> SEQ ID NO 53
<211> LENGTH: 71
<212> TYPE: DNA
<213> ORGANISM: Artificial
<220> FEATURE:
<223> OTHER INFORMATION: Ptrc promoter and 5' coding sequence

<400> SEQUENCE: 53
tgacaattaa tcatccggct cgtataatgt gtggaattgt gagcggataa caatttcaca      60
caggagtaaa a                                                          71

<210> SEQ ID NO 54
<211> LENGTH: 528
<212> TYPE: PRT
<213> ORGANISM: Homo sapiens

<400> SEQUENCE: 54

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Gly Ala Pro Gly Pro Ser Leu Thr Gly Ser Pro Trp Pro Gly
        35                  40                  45

Thr Ala Pro Ala Ala Ser Tyr Thr Pro Thr Pro Arg Ser Pro Arg
    50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Val Pro Ser Glu Pro Gly
                85                  90                  95

Asp Pro Leu Glu Ala Val Ala Phe Glu Glu Lys Glu Gly Lys Ala Val
            100                 105                 110

Leu Asn Leu Leu Phe Ser Pro Arg Ala Thr Lys Pro Ser Ala Leu Ser
        115                 120                 125

Arg Ala Val Lys Val Phe Glu Thr Phe Glu Ala Lys Ile His His Leu
    130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp Leu Asp His Pro Gly
    210                 215                 220

Phe Ser Asp Gln Val Tyr Arg Gln Arg Lys Leu Ile Ala Glu Ile
225                 230                 235                 240

Ala Phe Gln Tyr Arg His Gly Asp Pro Ile Pro Arg Val Glu Tyr Thr
                245                 250                 255
```

```
Ala Glu Glu Ile Ala Thr Trp Lys Glu Val Tyr Thr Leu Lys Gly
            260                 265                 270

Leu Tyr Ala Thr His Ala Cys Gly Glu His Leu Glu Ala Phe Ala Leu
        275                 280                 285

Leu Glu Arg Phe Ser Gly Tyr Arg Glu Asp Asn Ile Pro Gln Leu Glu
    290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
            340                 345                 350

His Ser Pro Glu Pro Asp Cys Cys His Glu Leu Leu Gly His Val Pro
        355                 360                 365

Met Leu Ala Asp Arg Thr Phe Ala Gln Phe Ser Gln Asp Ile Gly Leu
    370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
            420                 425                 430

Cys Leu Ser Glu Glu Pro Glu Ile Arg Ala Phe Asp Pro Glu Ala Ala
        435                 440                 445

Ala Val Gln Pro Tyr Gln Asp Gln Thr Tyr Gln Ser Val Tyr Phe Val
    450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
        515                 520                 525

<210> SEQ ID NO 55
<211> LENGTH: 498
<212> TYPE: PRT
<213> ORGANISM: Mus musculus

<400> SEQUENCE: 55

Met Pro Thr Pro Ser Ala Ser Ser Pro Gln Pro Lys Gly Phe Arg Arg
1               5                   10                  15

Ala Val Ser Glu Gln Asp Thr Lys Gln Ala Glu Ala Val Thr Ser Pro
            20                  25                  30

Arg Phe Ile Gly Arg Arg Gln Ser Leu Ile Glu Asp Ala Arg Lys Glu
        35                  40                  45

Arg Glu Ala Ala Ala Ala Ala Ala Ala Val Ala Ser Ala Glu
    50                  55                  60

Pro Gly Asn Pro Leu Glu Ala Val Val Phe Glu Arg Asp Gly Asn
65                  70                  75                  80

Ala Val Leu Asn Leu Leu Phe Ser Leu Arg Gly Thr Lys Pro Ser Ser
                85                  90                  95

Leu Ser Arg Ala Leu Lys Val Phe Glu Thr Phe Glu Ala Lys Ile His
```

```
                    100                 105                 110
His Leu Glu Thr Arg Pro Ala Gln Arg Pro Leu Ala Gly Ser Pro His
                115                 120                 125

Leu Glu Tyr Phe Val Arg Phe Glu Val Pro Ser Gly Asp Leu Ala Ala
130                 135                 140

Leu Leu Ser Ser Val Arg Arg Val Ser Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
                180                 185                 190

Pro Gly Phe Ser Asp Gln Ala Tyr Arg Gln Arg Lys Leu Ile Ala
                195                 200                 205

Glu Ile Ala Phe Gln Tyr Lys Gln Gly Glu Pro Ile Pro His Val Glu
                210                 215                 220

Tyr Thr Lys Glu Glu Ile Ala Thr Trp Lys Glu Val Tyr Ala Thr Leu
225                 230                 235                 240

Lys Gly Leu Tyr Ala Thr His Ala Cys Arg Glu His Leu Glu Ala Phe
                245                 250                 255

Gln Leu Leu Glu Arg Tyr Cys Gly Tyr Arg Glu Asp Ser Ile Pro Gln
                260                 265                 270

Leu Glu Asp Val Ser His Phe Leu Lys Glu Arg Thr Gly Phe Gln Leu
                275                 280                 285

Arg Pro Val Ala Gly Leu Leu Ser Ala Arg Asp Phe Leu Ala Ser Leu
290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
                340                 345                 350

Gly Leu Ala Ser Leu Gly Ala Ser Asp Glu Glu Ile Glu Lys Leu Ser
                355                 360                 365

Thr Val Tyr Trp Phe Thr Val Glu Phe Gly Leu Cys Lys Gln Asn Gly
                370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
                420                 425                 430

Phe Val Ser Glu Ser Phe Ser Asp Ala Lys Asp Lys Leu Arg Asn Tyr
                435                 440                 445

Ala Ser Arg Ile Gln Arg Pro Phe Ser Val Lys Phe Asp Pro Tyr Thr
                450                 455                 460

Leu Ala Ile Asp Val Leu Asp Ser Pro His Thr Ile Arg Arg Ser Leu
465                 470                 475                 480

Glu Gly Val Gln Asp Glu Leu His Thr Leu Thr Gln Ala Leu Ser Ala
                485                 490                 495

Ile Ser

<210> SEQ ID NO 56
<211> LENGTH: 491
```

```
<212> TYPE: PRT
<213> ORGANISM: Bos taurus

<400> SEQUENCE: 56
```

| | | | | | | | | | | | | | | |
|---|---|---|---|---|---|---|---|---|---|---|---|---|---|---|
| Met | Pro | Thr | Pro | Asn | Ala | Ala | Ser | Pro | Gln | Ala | Lys | Gly | Phe | Arg | Arg |
| 1 | | | | 5 | | | | | 10 | | | | | 15 | |

Ala Val Ser Glu Leu Asp Ala Lys Gln Ala Glu Ala Ile Met Ser Pro
            20                  25                  30

Arg Phe Val Gly Arg Arg Gln Ser Leu Ile Gln Asp Ala Arg Lys Glu
        35                  40                  45

Arg Glu Lys Ala Glu Ala Ala Ser Ser Glu Ser Ala Glu Ala
    50                  55                  60

Ala Ala Trp Leu Glu Arg Asp Gly Glu Ala Val Leu Thr Leu Leu Phe
65                  70                  75                  80

Ala Leu Pro Pro Thr Arg Pro Pro Ala Leu Thr Arg Ala Ile Lys Val
                85                  90                  95

Phe Glu Thr Phe Glu Ala His Leu His His Leu Glu Thr Arg Pro Ala
            100                 105                 110

Gln Pro Leu Arg Ala Gly Ser Pro Pro Leu Glu Cys Phe Val Arg Cys
        115                 120                 125

Glu Val Pro Gly Pro Val Val Pro Ala Leu Leu Ser Ala Leu Arg Arg
    130                 135                 140

Val Ala Glu Asp Val Arg Ala Ala Gly Glu Ser Lys Val Leu Trp Phe
145                 150                 155                 160

Pro Arg Lys Val Ser Glu Leu Asp Lys Cys His His Leu Val Thr Lys
                165                 170                 175

Phe Asp Pro Asp Leu Asp Leu Asp His Pro Gly Phe Ser Asp Gln Ala
            180                 185                 190

Tyr Arg Gln Arg Arg Lys Leu Ile Ala Glu Ile Ala Phe Gln Tyr Lys
        195                 200                 205

Gln Gly Asp Pro Ile Pro His Val Glu Tyr Thr Ala Glu Glu Thr Ala
    210                 215                 220

Thr Trp Lys Glu Val Tyr Ser Thr Leu Arg Gly Leu Tyr Pro Thr His
225                 230                 235                 240

Ala Cys Arg Glu His Leu Glu Ala Phe Glu Leu Leu Glu Arg Phe Cys
                245                 250                 255

Gly Tyr Arg Glu Asp Arg Ile Pro Gln Leu Glu Asp Val Ser Arg Phe
            260                 265                 270

Leu Lys Glu Arg Thr Gly Phe Gln Leu Arg Pro Ala Ala Gly Leu Leu
        275                 280                 285

Ser Ala Arg Asp Phe Leu Ala Ser Leu Ala Phe Arg Val Phe Gln Cys
    290                 295                 300

Thr Gln Tyr Ile Arg His Ala Ser Ser Pro Met His Ser Pro Glu Pro
305                 310                 315                 320

Glu Cys Cys His Glu Leu Leu Gly His Val Pro Met Leu Ala Asp Arg
                325                 330                 335

Thr Phe Ala Gln Phe Ser Gln Asp Ile Gly Leu Ala Ser Leu Gly Val
            340                 345                 350

Ser Asp Glu Glu Ile Glu Lys Leu Ser Thr Leu Tyr Trp Phe Thr Val
        355                 360                 365

Glu Phe Gly Leu Cys Lys Gln Asn Gly Glu Val Lys Ala Tyr Gly Ala
    370                 375                 380

Gly Leu Leu Ser Ser Tyr Gly Glu Leu Leu His Ser Leu Ser Glu Glu
385                 390                 395                 400

```
Pro Glu Ile Arg Ala Phe Asp Pro Asp Ala Ala Val Gln Pro Tyr
            405                 410                 415

Gln Asp Gln Thr Tyr Gln Pro Val Tyr Phe Val Ser Glu Ser Phe Ser
        420                 425                 430

Asp Ala Lys Asp Lys Leu Arg Ser Tyr Ala Ser Arg Ile Gln Arg Pro
        435                 440                 445

Phe Ser Val Lys Phe Asp Pro Tyr Thr Leu Ala Ile Asp Val Leu Asp
    450                 455                 460

Ser Pro His Ala Ile Arg His Ala Leu Asp Gly Val Gln Asp Glu Met
465                 470                 475                 480

Gln Ala Leu Ala His Ala Leu Asn Ala Ile Ser
                485                 490

<210> SEQ ID NO 57
<211> LENGTH: 491
<212> TYPE: PRT
<213> ORGANISM: Gallus gallus

<400> SEQUENCE: 57

Met Pro Thr Pro Asn Ile Ser Thr Ser Ala Ala Lys Gly Phe Arg Arg
1               5                   10                  15

Ala Val Ser Glu Leu Asp Ser Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Ala Ala Thr Asp Ala Ala Glu Ser Thr Glu Thr
    50                  55                  60

Ile Val Phe Glu Glu Lys Asp Gly Arg Ala Met Leu Asn Leu Phe Phe
65                  70                  75                  80

Met Leu Lys Gly Ala Lys Thr Ser Pro Leu Ser Arg Ala Leu Lys Val
                85                  90                  95

Phe Glu Thr Phe Glu Ala Lys Ile His His Leu Glu Thr Arg Leu Ser
            100                 105                 110

Arg Lys Pro Arg Glu Gly Thr Ala Glu Leu Glu Tyr Phe Val Arg Cys
        115                 120                 125

Glu Val His Ser Ser Asp Leu Asn Thr Phe Ile Ser Ser Ile Lys Arg
    130                 135                 140

Val Ala Glu Asp Val Arg Thr Thr Lys Glu Asp Lys Phe His Trp Phe
145                 150                 155                 160

Pro Arg Lys Ile Cys Glu Leu Asp Lys Cys His His Leu Val Thr Lys
                165                 170                 175

Phe Asp Pro Asp Leu Asp Leu Asp His Pro Gly Tyr Ser Asp Gln Val
            180                 185                 190

Tyr Arg Gln Arg Arg Lys Ser Ile Ala Glu Ile Ala Phe His Tyr Lys
        195                 200                 205

His Gly Asp Pro Ile Pro Arg Val Glu Tyr Thr Ala Glu Glu Thr Ala
    210                 215                 220

Thr Trp Lys Glu Val Tyr Ser Thr Leu Lys Ser Leu Tyr Pro Thr His
225                 230                 235                 240

Ala Cys Lys Glu Tyr Leu Glu Ala Phe Asn Leu Leu Glu Lys Phe Cys
                245                 250                 255

Gly Tyr Asn Glu Asn Asn Ile Pro Gln Leu Glu Glu Val Ser Arg Phe
            260                 265                 270

Leu Lys Glu Arg Thr Gly Phe Gln Leu Arg Pro Val Ala Gly Leu Leu
```

```
                    275                 280                 285
Ser Ala Arg Asp Phe Leu Ala Ser Leu Ala Phe Arg Val Phe Gln Cys
            290                 295                 300

Thr Gln Tyr Ile Arg His Ala Ser Ser Pro Met His Ser Pro Glu Pro
305                 310                 315                 320

Asp Cys Cys His Glu Leu Leu Gly His Val Pro Met Leu Ala Asp Lys
                325                 330                 335

Thr Phe Ala Gln Phe Ser Gln Asp Ile Gly Leu Ala Ser Leu Gly Ala
            340                 345                 350

Thr Asp Glu Glu Ile Glu Lys Leu Ala Thr Leu Tyr Trp Phe Thr Val
            355                 360                 365

Glu Phe Gly Leu Cys Arg Gln Asn Gly Ile Val Lys Ala Tyr Gly Ala
            370                 375                 380

Gly Leu Leu Ser Ser Tyr Gly Glu Leu Ile His Ser Leu Ser Asp Glu
385                 390                 395                 400

Pro Glu Val Arg Asp Phe Asp Pro Asp Ala Ala Val Gln Pro Tyr
                405                 410                 415

Gln Asp Gln Asn Tyr Gln Pro Val Tyr Phe Val Ser Glu Ser Phe Ser
            420                 425                 430

Asp Ala Lys Asn Lys Leu Arg Asn Tyr Ala Ala His Ile Lys Arg Pro
            435                 440                 445

Phe Ser Val Lys Tyr Glu Pro Tyr Thr His Ser Ile Glu Leu Leu Asp
            450                 455                 460

Ser Pro Gln Thr Ile Cys His Ser Leu Glu Ser Val Arg Asp Glu Leu
465                 470                 475                 480

His Ser Leu Ile Asn Ala Leu Asn Val Ile Ser
                485                 490

<210> SEQ ID NO 58
<211> LENGTH: 297
<212> TYPE: PRT
<213> ORGANISM: Chromobacterium violaceum

<400> SEQUENCE: 58

Met Asn Asp Arg Ala Asp Phe Val Val Pro Asp Ile Thr Thr Arg Lys
1               5                   10                  15

Asn Val Gly Leu Ser His Asp Ala Asn Asp Phe Thr Leu Pro Gln Pro
            20                  25                  30

Leu Asp Arg Tyr Ser Ala Glu Asp His Ala Thr Trp Ala Thr Leu Tyr
        35                  40                  45

Gln Arg Gln Cys Lys Leu Leu Pro Gly Arg Ala Cys Asp Glu Phe Met
    50                  55                  60

Glu Gly Leu Glu Arg Leu Glu Val Asp Ala Asp Arg Val Pro Asp Phe
65                  70                  75                  80

Asn Lys Leu Asn Gln Lys Leu Met Ala Ala Thr Gly Trp Lys Ile Val
                85                  90                  95

Ala Val Pro Gly Leu Ile Pro Asp Val Phe Glu His Leu Ala
            100                 105                 110

Asn Arg Arg Phe Pro Val Thr Trp Trp Leu Arg Glu Pro His Gln Leu
            115                 120                 125

Asp Tyr Leu Gln Glu Pro Asp Val Phe His Asp Leu Phe Gly His Val
        130                 135                 140

Pro Leu Leu Ile Asn Pro Val Phe Ala Asp Tyr Leu Glu Ala Tyr Gly
145                 150                 155                 160
```

```
Lys Gly Gly Val Lys Ala Lys Ala Leu Gly Ala Leu Pro Met Leu Ala
            165                 170                 175

Arg Leu Tyr Trp Tyr Thr Val Glu Phe Gly Leu Ile Asn Thr Pro Ala
        180                 185                 190

Gly Met Arg Ile Tyr Gly Ala Gly Ile Leu Ser Ser Lys Ser Glu Ser
        195                 200                 205

Ile Tyr Cys Leu Asp Ser Ala Ser Pro Asn Arg Val Gly Phe Asp Leu
        210                 215                 220

Met Arg Ile Met Asn Thr Arg Tyr Arg Ile Asp Thr Phe Gln Lys Thr
225                 230                 235                 240

Tyr Phe Val Ile Asp Ser Phe Lys Gln Leu Phe Asp Ala Thr Ala Pro
                245                 250                 255

Asp Phe Ala Pro Leu Tyr Leu Gln Leu Ala Asp Ala Gln Pro Trp Gly
            260                 265                 270

Ala Gly Asp Val Ala Pro Asp Leu Val Leu Asn Ala Gly Asp Arg
        275                 280                 285

Gln Gly Trp Ala Asp Thr Glu Asp Val
        290                 295

<210> SEQ ID NO 59
<211> LENGTH: 272
<212> TYPE: PRT
<213> ORGANISM: Xanthomonas campestris

<400> SEQUENCE: 59

Met Val Glu Gln Pro Trp Asp Gly Tyr Ser Ala Asp Asp His Ala Thr
1               5                   10                  15

Trp Gly Thr Leu Tyr Arg Arg Gln Arg Glu Leu Leu Val Gly Arg Ala
            20                  25                  30

Cys Glu Glu Phe Leu Gln Ala Gln Asp Ala Met Gly Met Gly Gln Thr
        35                  40                  45

His Ile Pro Arg Phe Asp Ala Leu Asn Arg Val Leu Gln Ala Ala Thr
    50                  55                  60

Gly Trp Thr Leu Val Gly Val Gln Gly Leu Leu Pro Glu Leu Asp Phe
65              70                  75                  80

Phe Asp His Leu Ala Asn Arg Arg Phe Pro Val Thr Trp Trp Ile Arg
                85                  90                  95

Arg Pro Asp Gln Ile Asp Tyr Ile Ala Glu Pro Asp Leu Phe His Asp
            100                 105                 110

Leu Phe Gly His Val Pro Leu Leu Met Asn Pro Leu Phe Ala Asp Phe
        115                 120                 125

Met Gln Ala Tyr Gly Arg Gly Val Lys Ala His Gly Ile Gly Pro
    130                 135                 140

Asp Ala Leu Gln Asn Leu Thr Arg Leu Tyr Trp Tyr Thr Val Glu Phe
145                 150                 155                 160

Gly Leu Ile Asp Thr Pro Gln Gly Leu Arg Ile Tyr Gly Ala Gly Ile
                165                 170                 175

Val Ser Ser Lys Gly Glu Ser Leu Tyr Ser Leu Glu Ser Pro Ala Pro
            180                 185                 190

Asn Arg Ile Gly Phe Asp Leu Gln Arg Ile Met Arg Thr Arg Tyr Arg
        195                 200                 205

Ile Asp Ser Phe Gln Lys Thr Tyr Phe Val Ile Asp Ser Phe Ala Gln
    210                 215                 220

Leu Met Glu Ala Thr Ala Pro Asp Phe Thr Pro Ile Tyr Ala Glu Leu
225                 230                 235                 240
```

```
Ala Gln Gln Pro Gln Val Pro Ala Gly Asp Val Leu Pro Gly Asp Arg
                245                 250                 255

Val Ile Gln Arg Gly Ser Gly Glu Gly Trp Ser Arg Asp Gly Asp Val
            260                 265                 270

<210> SEQ ID NO 60
<211> LENGTH: 262
<212> TYPE: PRT
<213> ORGANISM: Pseudomonas aeruginosa

<400> SEQUENCE: 60

Met Lys Thr Thr Gln Tyr Val Ala Arg Gln Pro Asp Asp Asn Gly Phe
1               5                   10                  15

Ile His Tyr Pro Glu Thr Glu His Gln Val Trp Asn Thr Leu Ile Thr
            20                  25                  30

Arg Gln Leu Lys Val Ile Glu Gly Arg Ala Cys Gln Glu Tyr Leu Asp
        35                  40                  45

Gly Ile Glu Gln Leu Gly Leu Pro His Glu Arg Ile Pro Gln Leu Asp
    50                  55                  60

Glu Ile Asn Arg Val Leu Gln Ala Thr Thr Gly Trp Arg Val Ala Arg
65                  70                  75                  80

Val Pro Ala Leu Ile Pro Phe Gln Thr Phe Phe Glu Leu Leu Ala Ser
                85                  90                  95

Gln Gln Phe Pro Val Ala Thr Phe Ile Arg Thr Pro Glu Glu Leu Asp
            100                 105                 110

Tyr Leu Gln Glu Pro Asp Ile Phe His Glu Ile Phe Gly His Cys Pro
        115                 120                 125

Leu Leu Thr Asn Pro Trp Phe Ala Glu Phe Thr His Thr Tyr Gly Lys
    130                 135                 140

Leu Gly Leu Lys Ala Ser Lys Glu Glu Arg Val Phe Leu Ala Arg Leu
145                 150                 155                 160

Tyr Trp Met Thr Ile Glu Phe Gly Leu Val Glu Thr Asp Gln Gly Lys
                165                 170                 175

Arg Ile Tyr Gly Gly Gly Ile Leu Ser Ser Pro Lys Glu Thr Val Tyr
            180                 185                 190

Ser Leu Ser Asp Glu Pro Leu His Gln Ala Phe Asn Pro Leu Glu Ala
        195                 200                 205

Met Arg Thr Pro Tyr Arg Ile Asp Ile Leu Gln Pro Leu Tyr Phe Val
    210                 215                 220

Leu Pro Asp Leu Lys Arg Leu Phe Gln Leu Ala Gln Glu Asp Ile Met
225                 230                 235                 240

Ala Leu Val His Glu Ala Met Arg Leu Gly Leu His Ala Pro Leu Phe
                245                 250                 255

Pro Pro Lys Gln Ala Ala
            260

<210> SEQ ID NO 61
<211> LENGTH: 262
<212> TYPE: PRT
<213> ORGANISM: Pseudomonas putida

<400> SEQUENCE: 61

Met Lys Gln Thr Gln Tyr Val Ala Arg Glu Pro Asp Ala His Gly Phe
1               5                   10                  15

Ile Asp Tyr Pro Gln Gln Glu His Ala Val Trp Asn Thr Leu Ile Thr
            20                  25                  30
```

-continued

```
Arg Gln Leu Lys Val Ile Glu Gly Arg Ala Cys Gln Glu Tyr Leu Asp
            35                  40                  45

Gly Ile Asp Gln Leu Lys Leu Pro His Asp Arg Ile Pro Gln Leu Gly
 50                  55                  60

Glu Val Asn Lys Val Leu Gly Ala Thr Thr Gly Trp Gln Val Ala Arg
 65                  70                  75                  80

Val Pro Ala Leu Ile Pro Phe Gln Thr Phe Phe Glu Leu Leu Ala Ser
                 85                  90                  95

Lys Arg Phe Pro Val Ala Thr Phe Ile Arg Thr Pro Glu Glu Leu Asp
            100                 105                 110

Tyr Leu Gln Glu Pro Asp Ile Phe His Glu Ile Phe Gly His Cys Pro
            115                 120                 125

Leu Leu Thr Asn Pro Trp Phe Ala Glu Phe Thr His Thr Tyr Gly Lys
        130                 135                 140

Leu Gly Leu Ala Ala Thr Lys Glu Gln Arg Val Tyr Leu Ala Arg Leu
145                 150                 155                 160

Tyr Trp Met Thr Ile Glu Phe Gly Leu Met Glu Thr Pro Gln Gly Arg
                165                 170                 175

Lys Ile Tyr Gly Gly Gly Ile Leu Ser Ser Pro Lys Glu Thr Val Tyr
            180                 185                 190

Ser Leu Ser Gly Glu Pro Glu His Gln Ala Phe Asp Pro Ile Glu Ala
            195                 200                 205

Met Arg Thr Pro Tyr Arg Ile Asp Ile Leu Gln Pro Leu Tyr Phe Val
        210                 215                 220

Leu Pro Asn Met Lys Arg Leu Phe Asp Leu Ala His Glu Asp Ile Met
225                 230                 235                 240

Gly Met Val His Lys Ala Met Gln Leu Gly Leu His Ala Pro Lys Phe
                245                 250                 255

Pro Pro Lys Val Ala Ala
            260

<210> SEQ ID NO 62
<211> LENGTH: 452
<212> TYPE: PRT
<213> ORGANISM: Homo sapiens

<400> SEQUENCE: 62

Met Ser Thr Ala Val Leu Glu Asn Pro Gly Leu Gly Arg Lys Leu Ser
 1               5                   10                  15

Asp Phe Gly Gln Glu Thr Ser Tyr Ile Glu Asp Asn Cys Asn Gln Asn
                20                  25                  30

Gly Ala Ile Ser Leu Ile Phe Ser Leu Lys Glu Glu Val Gly Ala Leu
            35                  40                  45

Ala Lys Val Leu Arg Leu Phe Glu Glu Asn Asp Val Asn Leu Thr His
 50                  55                  60

Ile Glu Ser Arg Pro Ser Arg Leu Lys Lys Asp Glu Tyr Glu Phe Phe
 65                  70                  75                  80

Thr His Leu Asp Lys Arg Ser Leu Pro Ala Leu Thr Asn Ile Ile Lys
                 85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
```

```
                130                 135                 140
Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Lys Lys Thr Trp Gly Thr Val Phe Lys
                180                 185                 190

Thr Leu Lys Ser Leu Tyr Lys Thr His Ala Cys Tyr Glu Tyr Asn His
                195                 200                 205

Ile Phe Pro Leu Leu Glu Lys Tyr Cys Gly Phe His Glu Asp Asn Ile
210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
                275                 280                 285

Gly His Val Pro Leu Phe Ser Asp Arg Ser Phe Ala Gln Phe Ser Gln
                290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
                340                 345                 350

Glu Leu Gln Tyr Cys Leu Ser Glu Lys Pro Lys Leu Leu Pro Leu Glu
                355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
                420                 425                 430

Leu Ala Asp Ser Ile Asn Ser Glu Ile Gly Ile Leu Cys Ser Ala Leu
                435                 440                 445

Gln Lys Ile Lys
450

<210> SEQ ID NO 63
<211> LENGTH: 453
<212> TYPE: PRT
<213> ORGANISM: Mus musculus

<400> SEQUENCE: 63

Met Ala Ala Val Val Leu Glu Asn Gly Val Leu Ser Arg Lys Leu Ser
1               5                   10                  15

Asp Phe Gly Gln Glu Thr Ser Tyr Ile Glu Asp Asn Ser Asn Gln Asn
                20                  25                  30

Gly Ala Val Ser Leu Ile Phe Ser Leu Lys Glu Glu Val Gly Ala Leu
                35                  40                  45
```

Ala Lys Val Leu Arg Leu Phe Glu Glu Asn Glu Ile Asn Leu Thr His
 50                      55                       60
Ile Glu Ser Arg Pro Ser Arg Leu Asn Lys Asp Glu Tyr Glu Phe Phe
 65                  70                  75                  80
Thr Tyr Leu Asp Lys Arg Ser Lys Pro Val Leu Gly Ser Ile Ile Lys
                 85                  90                  95
Ser Leu Arg Asn Asp Ile Gly Ala Thr Val His Glu Leu Ser Arg Asp
             100                 105                 110
Lys Glu Lys Asn Thr Val Pro Trp Phe Pro Arg Thr Ile Gln Glu Leu
         115                 120                 125
Asp Arg Phe Ala Asn Gln Ile Leu Ser Tyr Gly Ala Glu Leu Asp Ala
     130                 135                 140
Asp His Pro Gly Phe Lys Asp Pro Val Tyr Arg Ala Arg Arg Lys Gln
145                 150                 155                 160
Phe Ala Asp Ile Ala Tyr Asn Tyr Arg His Gly Gln Pro Ile Pro Arg
                 165                 170                 175
Val Glu Tyr Thr Glu Glu Glu Arg Lys Thr Trp Gly Thr Val Phe Arg
             180                 185                 190
Thr Leu Lys Ala Leu Tyr Lys Thr His Ala Cys Tyr Glu His Asn His
         195                 200                 205
Ile Phe Pro Leu Leu Glu Lys Tyr Cys Gly Phe Arg Glu Asp Asn Ile
     210                 215                 220
Pro Gln Leu Glu Asp Val Ser Gln Phe Leu Gln Thr Cys Thr Gly Phe
225                 230                 235                 240
Arg Leu Arg Pro Val Ala Gly Leu Leu Ser Ser Arg Asp Phe Leu Gly
                 245                 250                 255
Gly Leu Ala Phe Arg Val Phe His Cys Thr Gln Tyr Ile Arg His Gly
             260                 265                 270
Ser Lys Pro Met Tyr Thr Pro Glu Pro Asp Ile Cys His Glu Leu Leu
         275                 280                 285
Gly His Val Pro Leu Phe Ser Asp Arg Ser Phe Ala Gln Phe Ser Gln
     290                 295                 300
Glu Ile Gly Leu Ala Ser Leu Gly Ala Pro Asp Glu Tyr Ile Glu Lys
305                 310                 315                 320
Leu Ala Thr Ile Tyr Trp Phe Thr Val Glu Phe Gly Leu Cys Lys Glu
                 325                 330                 335
Gly Asp Ser Ile Lys Ala Tyr Gly Ala Gly Leu Leu Ser Ser Phe Gly
             340                 345                 350
Glu Leu Gln Tyr Cys Leu Ser Asp Lys Pro Lys Leu Leu Pro Leu Glu
         355                 360                 365
Leu Glu Lys Thr Ala Cys Gln Glu Tyr Thr Val Thr Glu Phe Gln Pro
     370                 375                 380
Leu Tyr Tyr Val Ala Glu Ser Phe Asn Asp Ala Lys Glu Lys Val Arg
385                 390                 395                 400
Thr Phe Ala Ala Thr Ile Pro Arg Pro Phe Ser Val Arg Tyr Asp Pro
                 405                 410                 415
Tyr Thr Gln Arg Val Glu Val Leu Asp Asn Thr Gln Gln Leu Lys Ile
             420                 425                 430
Leu Ala Asp Ser Ile Asn Ser Glu Val Gly Ile Leu Cys His Ala Leu
         435                 440                 445
Gln Lys Ile Lys Ser
450

```
<210> SEQ ID NO 64
<211> LENGTH: 279
<212> TYPE: PRT
<213> ORGANISM: Streptomyces coeruleorubidus

<400> SEQUENCE: 64

Met Gln Gly Pro His Ala Gln Met Thr Asp Ala Ala Tyr Glu Ile Arg
1               5                   10                  15

Arg Ser Glu Ile Ala Ala Leu Ser Thr Asp Leu Ala Pro Glu Asp Pro
                20                  25                  30

Ile Pro Val Val Glu Tyr Thr Glu Trp Glu His Glu Val Trp Arg Thr
            35                  40                  45

Val Cys Val Asp Leu Thr Ala Arg His Arg Thr Asp Ala Ala Ala Glu
        50                  55                  60

Tyr Leu Glu Ser Ala Glu Gln Leu Ala Val Pro Leu Asp His Val Pro
65                  70                  75                  80

Gln Leu Arg Asp Val Ser Gly Arg Leu Gly Ser Ile Ser Gly Phe Thr
                85                  90                  95

Phe Gln Ser Ala Pro Ala Leu Val Pro Leu Arg Glu Phe Cys Gly Gly
                100                 105                 110

Leu Ala Asn Ser Val Phe His Ser Thr Gln Tyr Leu Arg His Pro Arg
                115                 120                 125

Ser Pro Phe Tyr Thr Glu Asp Pro Asp Leu Leu His Asp Leu Val Gly
            130                 135                 140

His Gly Asn Val Leu Ala Ser Asp Arg Phe Ala Arg Leu Tyr Arg Leu
145                 150                 155                 160

Ala Gly Asn Ala Ala Ala Arg Val His Ser Thr Glu Ala Leu Gln Phe
                165                 170                 175

Ile Gly Lys Val Phe Trp Phe Thr Leu Glu Cys Gly Val Val Arg Glu
            180                 185                 190

Arg Gly Glu Arg Lys Ala Tyr Gly Ala Thr Leu Val Ser Ser Tyr Gly
            195                 200                 205

Glu Leu Asp His Phe Arg Ser Ala Asp Phe Arg Pro Leu Asp Ile Lys
    210                 215                 220

Ser Leu Ala Asp Val Glu Tyr Asp Ile Ser Thr Tyr Gln Pro Ile Leu
225                 230                 235                 240

Phe Glu Ala Asp Ser Met Asp Glu Val Glu Asp Thr Val Gly Ser Phe
                245                 250                 255

Trp Asp Thr Cys Asp Asp Asp Ser Ile Ala Ala Leu Leu Gly Gly Thr
                260                 265                 270

Ser Arg Ser Val Thr Pro His
            275
```